United States Patent
Kim et al.

(10) Patent No.: US 9,750,768 B2
(45) Date of Patent: Sep. 5, 2017

(54) METHODS FOR PURIFYING MIDBRAIN DOPAMINERGIC NEURAL PROGENITOR CELLS

(75) Inventors: Kwang-Soo Kim, Lexington, MA (US); Sangmi Chung, Lexington, MA (US)

(73) Assignee: THE MCLEAN HOSPITAL CORPORATION, Belmont, CA (US)

( * ) Notice: Subject to any disclaimer, the term of this patent is extended or adjusted under 35 U.S.C. 154(b) by 0 days.

(21) Appl. No.: 14/118,982

(22) PCT Filed: May 18, 2012

(86) PCT No.: PCT/US2012/038513
§ 371 (c)(1), (2), (4) Date: Feb. 13, 2014

(87) PCT Pub. No.: WO2012/162124
PCT Pub. Date: Nov. 29, 2012

(65) Prior Publication Data
US 2014/0199274 A1    Jul. 17, 2014

Related U.S. Application Data

(60) Provisional application No. 61/488,678, filed on May 20, 2011.

(51) Int. Cl.
| | | |
|---|---|---|
| *A61K 35/30* | (2015.01) | |
| *C12N 5/00* | (2006.01) | |
| *C07K 16/28* | (2006.01) | |
| *C12N 5/0797* | (2010.01) | |
| *C07K 16/40* | (2006.01) | |

(52) U.S. Cl.
CPC .......... *A61K 35/30* (2013.01); *C07K 16/2863* (2013.01); *C07K 16/40* (2013.01); *C12N 5/0623* (2013.01); *C12N 2500/25* (2013.01); *C12N 2501/115* (2013.01); *C12N 2501/15* (2013.01); *C12N 2501/235* (2013.01); *C12N 2501/60* (2013.01); *C12N 2506/02* (2013.01); *C12N 2506/45* (2013.01)

(58) Field of Classification Search
None
See application file for complete search history.

(56) References Cited

U.S. PATENT DOCUMENTS

2007/0128168 A1    6/2007    Jorgensen et al.

FOREIGN PATENT DOCUMENTS

| EP | 1666590 | 6/2006 |
|---|---|---|
| RU | 2407790 | 12/2010 |
| WO | 0183715 A2 | 11/2001 |
| WO | 2007/021004 A1 | 2/2007 |
| WO | 2007/119759 A1 | 10/2007 |
| WO | 2010096496 | 8/2010 |
| WO | 2011130675 | 10/2011 |

OTHER PUBLICATIONS

Smidt et al. Nature Reviews Neurosci., 8:21-32, 2007.*
Ono by et al., Development 134:3213-3225, 2007.*
Andersson et al., PLoS ONE, 3(10):e3517, Oct. 2008.*
Summerhurst et al. 3D representation of Wnt and Frizzled gene expression patterns in the mouse embryo at embryonic day 11.5 (Tsl9). Gene Expr Patterns 8, 331-348 (2008).*
Zeng et al., "Dopaminergic differentiation of human embryonic stem cells", Stem Cells 22, pp. 925-940 (2004).
Yan et al., "Directed differentiation of dopaminergic neuronal subtypes from human embryonic stem cells", Stem Cells, 23(6): pp. 781-790 (2005).
Gale et al., "Midbrain dopaminergic neuron fate specification: of mice and embryonic stem cells", Molecular Brain, 1(1):8 (2008).
Chung et al., "ES cell-derived renewable and functional midbrain dopaminergic progenitors", PNAS, 108(23), pp. 9703-9708 (2011).
Chung et al., "Genetic selection of sox1GFP-expressing neural precursors removes residual tumorigenic pluripotent stem cells and attenuates tumor formation after transplantation", J Neurochem 97, pp. 1467-1480 (2006a).
Bjorklund et al, Embryonic stem cells develop into functional dopaminergic neurons after transplantation in a Parkinson rat model, PNAS, pp. 2344-2349, (Feb. 19, 2002).
Chung et al., "Generic engineering of mouse embryonic stem cells by Nurr1 enhances differentiation and maturation into dopaminergic neurons", Eur J Neurosci, 16(1); pp. 1829-1839, (Nov. 2002).
Kawasaki et al., "Induction of Midbrain Dopaminergic Neurothechnique Neurons from ES Cells by Stromal Cell-Derived Inducing Activity", Neuron, vol. 28, pp. 31-40, (Oct. 2000).
Kim et al., "Dopamine neurons derived from embryonic stem cells function in an animal model of Parkinson's disease", Nature, vol. 418, pp. 50-56, (Jul. 4, 2002).
Lindvall and Kokaia, "Prospects of stem cell therapy for replacing dopamine neurons in Parkinson's disease", Elsevier, pp. 260-267, (2009).
Perrier et al., "Derivation of midbrain dopamine neurons from human embryonic stem cells", PNAS, vol. 101(34), pp. 12543-12548, (Aug. 24, 2004).
Roy et al., "Functional engraftment of human ES cell-derived dopaminergic neurons enriched by coculture with telomerase-immortalized midbrain astrocytes", Nature Medicine, vol. 2(11), pp. 1259-1268, (Nov. 2006).
Schulz et al., "Differentiation of Human Embryonic Stem Cells to Dopaminergic Neurons in Serum-Free Suspension Culture", Stem Cells 2004;22: pp. 1218-1238 (2004).

(Continued)

*Primary Examiner* — Kimberly A. Ballard
*Assistant Examiner* — Stacey Macfarlane
(74) *Attorney, Agent, or Firm* — Nixon Peabody LLP; David S. Resnick; Nicole D. Kling

(57) ABSTRACT

Provided are methods of isolating a novel cell population of midbrain dopaminergic neuronal progenitor cells derived from stem cells using a novel combination markers. The cell population may be used for cell therapies for the treatment of Parkinson's disease and as substrates in pharmacological assays.

10 Claims, 18 Drawing Sheets

(56) References Cited

OTHER PUBLICATIONS

Politis et al., "Serotonergic Neurons Mediate Dyskinesia Side Effects in Parkinson's Patients with Neural Transplants", Sci Transl Med 2, 38ra46 (2010).
Li et al., "Expression of Wnt5a and its receptor Fzd2 is changed in the spinal cord of adult amyotrophic lateral sclerosis transgenic mice", Int J Clin Exp Pathol. 6(7):1245-1260 (2013).
Ring et al., "β-Catenin-dependent pathway activation by both promiscuous "canonical" WNT3a-, and specific "noncanonical" WNT4- and WNT5a-FZD receptor combinations with strong differences in LRP5 and LRP6 Dependency", Cellular Signalling 26:260-267 (2014).
Sato et al., "Wnt5a regulates distinct signalling pathways by binding to Frizzled2", The EMBO Journal 29(1):41-54 (2010).
Ye et al., "Wnt5a uses CD146 as a receptor to regulate cell motility and convergent extension", Nature Communications 4:2803 (2013).
Fougerousse et al., "Human-mouse differences in the embryonic expression patterns of developmental control genese and disease genes", Human Molecular Genetics 9(2):165-173 (2000).
Ginis et al., "Differences between human and mouse embryonic stem cells", Developmental Biology 269(2):360-380 (2004).

\* cited by examiner

1A

1B

SEQ ID NO: 1
```
   1 tgctgccatg tgccgctgcc acgggtaccc agcctgtcgc taaactttcc gggcgccagc
  61 ccggctctga gtcgcgcttc tcagcggagt gacccaggga cggaggaccc aggctggctg
 121 gggactgtct gctcttctcg gcgggatccg tggaggtgag aaccttccct ttctccctgt
 181 tcttctcccg tttcctgtgc cctttccgg gaagctgagg gttctggtct ccgggcactg
 241 cctgaagggc ccagcttgga aagagagggt gggggagtcg gtagtttggt tacaggaggc
 301 ggagcgggga ggaaaggaaa ggggttaact taagagattt ggagacagct cgcggggacc
 361 gaactgttga cgcctctcca cagggagtg gttgcaatct ttcttctccc ccttcttttt
 421 taaagagtcc tttccctgga atccgagccc taaccgtctc tcccagccc tatccggcga
 481 ggagcggagc gctgccagcg gaggcagcgc cttcccgaag cagtttatct tggacggtt
 541 ttctttaaag gaaaaagcaa ccaacaggtt gccagccccg gcgccacaca cgagacgccg
 601 gagggagaag ccccggcccg gattcctctg cctgtgtgcg tccctcgcgg gctgctggag
 661 gcgaggggag ggaggggggcg atggctcggc ctgacccatc cgcgccgccc tcgctgttgc
 721 tgctgctcct agcgcagctg gtgggccggg cggccgccgc gtccaaggcc ccggtgtgcc
 781 aggaaatcac ggtgcccatg tgccgcggca tcggctacaa cctgacgcac atgcccaacc
 841 agttcaacca cgacacgcag gacgaggcgg gcctggaggt gcaccagttc tggccgctgg
 901 tggagatcca atgctcgccg gacctgcgct tcttcctatg ctctatgtac acgcccatct
 961 gtctgcccga ctaccacaag ccgctgccgc cctgccgctc ggtgtgcgag cgcgccaagg
1021 ccggctgctc gccgctgatg cgccagtacg gcttcgcctg gcccgagcgc atgagctgcg
1081 accgcctccc ggtgctgggc cgcgacgccg aggtcctctg catggattac aaccgcagcg
1141 aggccaccac ggcgccccc aggcctttcc cagccaagcc cacccttcca ggcccgccag
1201 gggcgccggc ctcgggggggc gaatgccccg ctgggggccc gttcgtgtgc aagtgtcgcg
1261 agcccttcgt gccccattctg aaggagtcac acccgctcta acaacaaggtg cggacgggcc
1321 aggtgcccaa ctgcgcggta ccctgctacc agccgtcctt cagtgccgac gagcgcacgt
1381 tcgccaccct ctggatagc ctgtggtcgg tgctgtgctt catctccacg tccaccacag
1441 tggccacctt cctcatcgac atggaacgct tccgctatcc tgagcgcccc atcatcttcc
1501 tgtcagcctg ctacctgtgc gtgtcgctgg gcttcctggt gcgtctggtc gtgggccatg
1561 ccagcgtggc ctgcagccgc gagcacaacc acatccacta cgagaccacg ggccctgcac
1621 tgtgcaccat cgtcttcctc ctggtctact tcttcggcat ggccagctcc atctggtggg
1681 tcatcctgtc gctcacctgg ttcctggccg ccggcatgaa gtggggcaac gaggccatcg
1741 cgggctacgc gcagtacttc cacctggctg cgtggctcat cccagcgtc aagtccatca
1801 cggcactggc gctgagctcc gtggacgggg accagtggcc cggcatctgc tacgtgggca
1861 accagaacct gaactcgctg cgcggcttcg tgctgggccc gctggtgctc taccctgctgg
1921 tgggcacgct cttcctgctg gcgggcttcg tgtcgctctt ccgcatccgc agcgtcatca
1981 agcagggcgg caccaagacg gacaagctgg agaagctcat gatccgcatc ggcatcttca
2041 cgctgctcta cacggtcccc gccagcattg tggtggcctg ctacctgtac gagcagcact
2101 accgcgagag ctgggaggcg gcgctcacct gcgctgccc gggccacgac accggccagc
2161 cgcgcgccaa gcccgagtac tgggtgctca tgctcaagta cttcatgtgc ctggtggtgg
2221 gcatcacgtc gggcgtctgg atctggtcgg gcaagacggt ggagtcgtgg cggcgtttca
2281 ccagccgctg ctgctgccgc ccgcggcgcg gccacaagag cgggggcgcc atggccgcag
```

Figure 5

2341 gggactaccc cgaggcgagc gccgcgctca caggcaggac cgggccgccg ggccccgccg
2401 ccacctacca caagcaggtg tccctgtcgc acgtgtagga ggctgccgcc gagggactcg
2461 gccggagagc tgaggggagg ggggcgtttt gtttggtagt tttgccaagg tcacttccgt
2521 ttaccttcat ggtgctgttg cccctcccg cggcgacttg gagagaggga agaggggcgt
2581 tttcgaggaa gaacctgtcc caggtcttct ccaaggggcc cagctcacgt gtattctatt
2641 ttgcgtttct tactgccttc tttatgggaa ccctcttttt aatttatatg tatttttctt
2701 aatttgtaac tttgttgcat tttggcaaca atttaccttt gctttggggg ctttacaatc
2761 ctaaggttgg cgttgtaatg aagttccact tggttcaggt ttcttgaac tgtgtggtct
2821 caattgggaa aatatatttc ctatacgtgt gtctttaaaa aaaaatgtga acagtgaacg
2881 tttcggttgc tgtgactggg aagttgttgg gtgtgctttt tcagccagct tctccttcca
2941 ctgcttaaag tgtccatgat tctttaaggt gagctgcagt ttatagcccc aggtcatacc
3001 taggagggga gcataatgag ctcagggcct ccccaaagtg acaaggttag ggagtgctta
3061 gcggttttgt gttcagcctt agctttgttt atagagggag gttcagtttc ttttctgtag
3121 tgcttgtaat aattctcact cctaacagca ccatcgttgt gtcttgaata agttagaggt
3181 agcattatag aggatctggc ataaatattt gcagtagtga gagcctaagc gatggtgatt
3241 ggtggagctt gaattttagg ctggtgagat ggcagctttg tgcctgagag gtagtgggtg
3301 gttcttaagc ttcagtgatc ccctttttt ttttttt ttttttttaa ggaacttgtg
3361 ttataatttt ggtaaaagta taaacccact ccctctggac aatacttagc gacagttgct
3421 aaagggggct ccttttaaa tgtaaggact gaaatggata tacttctaat aagtaaattt
3481 ccaacactta tttgctccac ccccctcccc ctccccccct ccccttttatc atgttaaaca
3541 gccttttgc ttttcttatt cctcctctcc tggagagctg tgattagaaa ccacacccac
3601 ccttgaatga agtgcttgaa ctgggggagg gaggctggct acctgtgaac aaacattggc
3661 ccaaataagg gaaataagt gttcctggac tttggactag tttatagcca gatattccaa
3721 gagcagcaag acgttgctct ctgccgtctc tgaaaacaaa agagatgcat aacatgcttg
3781 cacaacctt taaatatag atcagtatag tgctacctct atagttttct tcctcttctg
3841 agaaagcctg tatattgatg atcacacaca cacacacttt gcaattagag aatttggttt
3901 gctttactaa tctgtttaac tattccttca ttcattatga acgcttatat tgatgaacat
3961 acacacagag gtttctttgc tattagaaaa ttctgtttgc tttcctaatc tgtttaagca
4021 ttcattcatg aagagtgtgg ggccattact ggggaagggg ggtgacagtg cctcagccag
4081 caaaatacca atgaccagga ttggggacta aatttaggaa gctaaatgg ccagagcaat
4141 taacatttga gaaaatcctg tctaggaaaa caacttgagt gtaggcattt gtaattcact
4201 tataccaaag ttggaaaagt aaaatttaag cctaggacaa tttttacttc atggatgtta
4261 aatagacaaa tgcatagttc ccaggggaa tttaaacact ttactggtgg gaagaaacct
4321 agtattaaag ttgtaaggac tctcaaaaac ttcacattta ttaaaatgca ctgctcttac
4381 ccaatttatc ctctgaatta aaatttcagt ggattctaca aaacctgta caaatagcta
4441 cagaacttg tgcctatttt attcctctat ttattcttct aggaagaagc ctcttcctag
4501 aatcttgaaa tagatccctt gactgaatgc caattcctct cctgttttc aaatgagaga
4561 accttttctg atcaccttga ccttttccct cattcat gtcttccag aaagtagaca
4621 gactgctctg ctgccttcag tcattgtgcc tcattgggt tgtccctcct tctttgtgga

Figure 5 (cont)

```
4681 gaaatctgga aatgatgcac agtgtatcca aaagttgtgg gatgaagtgg atgaaagtga
4741 tttaattcat ttttagaatt ttttttgtt ttgttttagc aacatgctga acaactaatt
4801 tactttaaaa ataagccagt taaaacaaag gacgctaagc ccaagtgggg ggcaatatta
4861 gtcaggatct ttggggtcta attccagacc aactttcaga agcacttctt tgtctctgtt
4921 ctcacctctg ctgtccctct cttccctcat ccctaagag agacaaagat aaaagcccac
4981 ctgcatccct aagtcttact gagatcagcc accccagggg agagaaactg gatctactta
5041 cagccacccc ctgttccat ccatatagtt acttccccca atttgcatgt gattatggaa
5101 acaagtcatg ctcatgaaag caactgtaaa ataaaaggtt atggagtagt tcagcaactt
5161 cttcacagcc agctttgtgg agctggggag gacttagggc ccattggagt ctctatgtg
5221 tacagcttca gggctgtccc tttcagtttg attttaagca atgcctcact tcatagctta
5281 gggggtaagg attccattca ggtaggttgt ctaaaggaac taatgggacc tctcagtgaa
5341 ttagctgacc agattttagg aaatctttt aattctatg attttcttc tcacattttg
5401 aaatggtaaa attgactgga aataatttt cttggtgcct tattggtttt ccttgcaaac
5461 ctttctcata ttttctcatg accattgcca gtgaccaagg cccatgtgtg tgttgtgtgt
5521 aattgtgggc atgtacaagc ttaaataacg tgccgacagc actgtttcaa agttggtatt
5581 cattaggctg ttgcctcctg ggctggagct gcgctaatcc tgacaccggc tgccaggaga
5641 aaacctcatg gatcacacac caaaccttaa taacagcatc cgtgacctgc actctccagt
5701 acagaatggg aacccagag ctaggaaatg tagttgtata ttttaatgaa ctgctacccc
5761 agccaaagaa gcttctttca cttttgtgct ctacagaaag cccaaggggg gtaggaggga
5821 cagagctttg aataactgct ttctaacact aaatgtggcc aacaggacag agcacatcac
5881 acgtataggc aggtgtgagg gacagtggct aagaattgcc tgctccctct gcatgctctt
5941 tcttgtttcc aaagtccaat caagtgatcc tgggaaacaa atctgtctgg attgcggagg
6001 gtggttctga aagaactgcc aagacgttaa agaagggtga agagtaggca gaatataagt
6061 agctaacctg agtcaagact ctcaaaagct agcagcctga tgacaatagg attatttca
6121 gccaggatag tgtctgtctg tgagtgcatc attaagac agtatgactt catgttgtta
6181 caaactatgt atagtatgta tgttttgtgg gttgtatata tacataatat atattatata
6241 tatatatgag agatttggtg acttttgata cgggtttggt gcaggtgaat ttattactga
6301 gccaaatgag gcacataccg agtcagtagt tgaagtccag ggcattcgat actgtttatg
6361 attccatat atgtatagtg cctatcccat gctgtagtca ctgttatgtt aaatccagaa
6421 gttacactag agccagcgat actttatttg tagacaatca atttgaatcc atatgttatt
6481 actggcagat gatacatgat tacagttctg aatctgtaac acttacaaaa ggaaacccag
6541 agcagcttga tgagttttg ttctgcttc gttcctggga gtcagtagaa acagcagttg
6601 tatgtggtta tgttagtctc aagatactta atttgttgac cttacttcag aaaaattttg
6661 tatgtattat atttgtggga aggtaaaata atcatttgag atttttatca aaatatgaaga
6721 ttagttattt atgaaaaaca aagaaatgtc tatttttctt tgttcccaat taatgtagat
6781 aaattttaaa atgcattaaa gtaatggtaa agacaataaa aagatgctgt agaa
```

Figure 5 (cont)

SEQ ID NO: 2
```
   1 aaatcatccg tagtgcctcc ccggggggaca cgtagaggag agaaaagcga ccaagataaa
  61 agtggacaga agaataagcg agactttta tccatgaaac agtctcctgc cctcgctccg
 121 gaagagcgct gccgcagagc cgggtcccca aagccggtct tgagagctga tgacaataac
 181 atgggcaatg gctgctctca gaagctggcg actgctaacc tcctccggtt cctattgctg
 241 gtcctgattc catgtatctg tgctctcgtt ctcttgctgg tgatcctgct ttcctatgtt
 301 ggaacattac aaaaggtcta ttttaaatca aatgggagtg aacctttggt cactgatggt
 361 gaaatccaag gtccgatgt tattcttaca aatacaattt ataaccagag cactgtggtg
 421 tctactgcac atcccgacca acacgttcca gcctggacta cggatgcttc tctcccaggg
 481 gaccaaagtc acaggaatac aagtgcctgt atgaacatca cccacagcca gtgtcagatg
 541 ctgccctacc acgccacgct gacacctctc ctctcagttg tcagaaacat ggaaatggaa
 601 aagttcctca agttttcac atatctccat cgcctcagtt gctatcaaca tatcatgctg
 661 tttggctgta ccctcgcctt ccctgagtgc atcatgatg gcgatgacag tcatggactc
 721 ctgccctgta ggtccttctg tgaggctgca aagaaggct gtgaatcagt cctggggatg
 781 gtgaattact cctggccgga tttcctcaga tgctcccagt ttagaaacca aactgaaagc
 841 agcaatgtca gcagaatttg cttctcacct cagcaggaaa acggaaagca attgctctgt
 901 ggaaggggtg agaactttct gtgtgccagt ggaatctgca tccccgggaa actgcaatgt
 961 aatggctaca cgactgtga cgactggagt gacgaggctc attgcaactg cagcgagaat
1021 ctgtttcact gtcacacagg caagtgcctt aattacagcc ttgtgtgtga tggatatgat
1081 gactgtgggg atttgagtga tgagcaaaac tgtgattgca atcccacaac agagcatcgc
1141 tgcggggacg ggcgctgcat cgccatggag tgggtgtgtg atggtgacca cgactgtgtg
1201 gataagtctg acgaggtcaa ctgctcctgt cacagccagg gtctggtgga atgcagaaat
1261 ggacaatgta tcccagcac gtttcaatgt gatggtgacg aggactgcaa ggatgggagt
1321 gatgaggaga actgcagcgt cattcagact tcatgtcaag aaggagacca aagatgcctc
1381 tacaatccct gccttgattc atgtggtggt agctctctct gtgacccgaa caacagtctg
1441 aataactgta gtcaatgtga accaattaca ttggaactct gcatgaattt gccctacaac
1501 agtacaagtt atccaaatta ttttggccac aggactcaaa aggaagcatc catcagctgg
1561 gagtcttctc tttcccctgc acttgttcaa accaactgtt ataaatacct catgttcttt
1621 tcttgcacca ttttggtacc aaaatgtgat gtgaatacag gcgagcatat ccctccttgc
1681 agggcattgt gtgaacactc taaagaacgc tgtgagtctg ttcttgggat tgtgggccta
1741 cagtggcctg aagacacaga ttgcagtcaa tttccagagg aaaattcaga caatcaaacc
1801 tgcctgatgc ctgatgaata tgtggaagaa tgctcaccta gtcatttcaa gtgccgctca
1861 ggacagtgtg ttctggcttc cagaagatgt gatggccagg ccgactgtga cgatgacagt
1921 gatgaggaaa actgtggttg taagagaga gatctttggg aatgtccatc caataaacaa
1981 tgtttgaagc acacagtgat ctgcgatggg ttcccagact gcctgatta catggacgag
2041 aaaaactgct cattttgcca agatgatgag ctggaatgtg caaaccatgc gtgtgtgtca
2101 cgtgacctgt ggtgtgatgg tgaagccgac tgctcagaca gttcagatga atgggactgt
2161 gtgaccctct ctataaatgt gaactcctct tccttctga tggttcacag agctgccaca
2221 gaacaccatg tgtgtcaga tggctggcag gagatattga gtcagctggc tgcaagcag
2281 atggggttttag gagaaccatc tgtgaccaaa ttgatacagg aacaggagaa agagccgcgg
2341 tggctgacat tacactccaa ctgggagagc ctcaatggga ccactttaca tgaacttcta
2401 gtaaatgggc agtcttgtga gagcagaagt aaaatttctc ttctgtgtac taaacaagac
```

Figure 6

```
2461 tgtgggcgcc gccctgctgc ccgaatgaac aaaaggatcc ttggaggtcg gacgagtcgc
2521 cctggaaggt ggccatggca gtgttctctg cagagtgaac ccagtggaca tatctgtggc
2581 tgtgtcctca ttgccaagaa gtgggttctg acagttgccc actgcttcga ggggagagag
2641 aatgctgcag tttgaaaagt ggtgcttggc atcaacaatc tagaccatcc atcagtgttc
2701 atgcagacac gctttgtgaa gaccatcatc ctgcatcccc gctacagtcg agcagtggtg
2761 gactatgaca tcagcatcgt tgagctgagt gaagacatca gtgagactgg ctacgtccgg
2821 cctgtctgct tgcccaaccc ggagcagtgg ctagagcctg acacgtactg ctatatcaca
2881 ggctggggcc acatgggcaa taaaatgcca tttaagctgc aagagggaga ggtccgcatt
2941 atttctctgg aacattgtca gtcctacttt gacatgaaga ccatcaccac tcggatgata
3001 tgtgctggct atgagtctgg cacagttgat tcatgcatgg gtgacagcgg tgggcctctt
3061 gtttgtgaga agcctggagg acggtggaca ttatttggat taacttcatg gggctccgtc
3121 tgcttttcca aagtcctggg gcctggcgtt tatagtaatg tgtcatattt cgtcgaatgg
3181 attaaaagac agatttacat ccagaccttt ctcctaaact aattataagg atgatcagag
3241 actttgcca gctacactaa aagaaaatgg cctcttgac tgtgaagagc tgcctgcaga
3301 gagctgtaca gaagcacttt tcatggacag aaatgctcaa tcgtgcactg caaatttgca
3361 tgtttgtttt ggactaattt tttcaattt atttttcac cttcattttt ctcttattc
3421 aagtcaatg aaagacttta caaaagcaaa caaagcagac tttgtcctt tgccaggcct
3481 aaccatgact gcagcacaaa attatcgact ctggcgagat ttaaaatcag gtgctacagt
3541 aacaggttat ggaatggtct cttttatcct atcacaaaaa aagacataga tatttaggct
3601 gattaattat ctctaccagt ttttgttct caagctcagt gcatagtggt aaatttcagt
3661 gttaacattg gagacttgct tttcttttc ttttttata cccacaatt cttttttatt
3721 acacttcgaa tttaggggta cacgagcaca acgtgcaggt tagttacata tgtatacatg
3781 tgccatgttg gtgtgctgaa cccagtaact cgtcatttga tttattaaaa gccaagataa
3841 tttacatgtt taaagtattt actattaccc cctctaaatg tttgcataat tctgagaact
3901 gataaaagac agcaataaaa gaccagtgtc atccatttag gtagcaagac atattgaatg
3961 caaagttctt tagatatcaa tattaacact tgacattatt ggacccccca ttctggatgt
4021 atatcaagat cataaatttta tagaagagtc tctatagaac tgtcctcata gctgggtttg
4081 ttcaggatat atgagttggc tgattgagac tgcaacaact acatctatat ttatgggcaa
4141 tattttgttt tacttatgtg gcaaagaact ggatattaaa ctttgcaaaa gagaatttag
4201 atgagagatg caatttttta aaaagaaaat taatttgcat ccctcgttta attaaattta
4261 tttttcagtt ttcttgcgtt catccatacc aacaaagtca taaagagcat attttagagc
4321 acagtaagac tttgcatgga gtaaaacatt ttgtaatttt cctcaaaaga tgtttaatat
4381 ctggtttctt ctcattggta attaaaattt tagaaatgat ttttagctct aggccacttt
4441 acgcaactca atttctgaag caattagtgg taaaaagtat ttttccccac taaaaaactt
4501 taaaacacaa atcttcatat atacttaatt taattagtca ggcatccatt ttgccttta
4561 aacaactagg attccctact aacctccacc agcaacctgg actgcctcag cattccaaat
4621 agatactacc tgcaattta tacatgtatt tttgtatctt ttctgtgtgt aaacatagtt
4681 gaaattcaaa aagtgtagc aatttctata ctattcatct cctgtccttc agtttgtata
4741 aacctaagga gagtgtgaaa tccagcaact gaattgtggt cacgattgta tgaaagttca
4801 agaacatatg tcagttttgt tacagttgta gctacatact caatgtatca actttttagcc
4861 tgctcaactt aggctcagtg aaatatatat attatactta ttttaaataa ttcttaatac
4921 aaataaaatg gtaatggtct aa
```

Figure 6 (cont)

SEQ ID NO: 3
```
   1 gagagcggga ccggcctcag ctccaacaca gcctccactg tgattaaaaa taaaaattgc
  61 tagagcagcc ctcactcgcc acatctactt tgtatgtatt gcagaggggc ccacgcgtgt
 121 ttagaactct agccgccttc ctcattttcg ttctttaaaa aaaattttt ttggtgtgt
 181 ttgacttttc atggaagggt gaagactgca aggtttctaa ctcaatactc ttgatttctt
 241 ttaggatagc tggctatttg gaatttaaag gatatttgac ttttctaac ctcccatgag
 301 gctgtaaggt aagtgtccgt ctgtcttgtc tatatccata tctacgtgtc cccgtgtctg
 361 tcggccatca ccccagtacc tccaatagac cgaccgatgc ccctctgcga acgtggagtt
 421 ctgtaggcgg atgtattttt tctcttacaa attttgaggt gtaataacga tcgttgcaaa
 481 aagaaaaatg tgatctagag atgagagcgg tagtgggaga gaggcagaga gcgtgctcct
 541 ggggtcgtc gcttctgcaa aacgtcgtcg aaacgctgcg aatgtaatct ggggtgtttt
 601 ggaaggtttt gtttgtggtt ttgttttat gtcaacgccg ttctgggctt ctcccgcgat
 661 ctttgcgttt tggccccccag atttggttgg ggtcgtttgg atggatccca gggaccttt
 721 tagagtccga gacaaaaaga tgcagatgta actagatgga tgattgaaaa caacaataat
 781 aaaaagccag gcgcctcctt gggcccgcgc gccggaagct cggttcgctt gcgggtcggc
 841 ctgggccggg ggccgccgct cgagccctg tcggccctg ttgaacgtga gcggaaaccg
 901 gagcggataa ccgaggaggc tgggagcgct ggcttctcgt ccgccccggc gctcactgct
 961 cgctctcttt ggcctcctct ccctcagcct agcacagctc ggttgtctgt ttctcccaaa
1021 agcttccaga tctccttttt gttttaaat atccaccacc cccaaaatc caaaccaccc
1081 tgggttgtaa ttacgcagcc tcccaacccc cggtgtcgt ggtccccgac cctggtcacc
1141 aggccgagcg aacgtgaaga gtgttttttc aacatgactt tgccgggtcg cggcccgccc
1201 cacgtagccc tccgcgcgca cctggggcgg gcagaagtgg cagctagtgg ccctgctcc
1261 gcccaaggcc gcggccgggc cagggaccgg aatcctcccg ctgggaccgc ggcccctcag
1321 ctgttctctg gcggggagag gcagggctcg cccgcgcgct cgcgcacccc cttcccaggc
1381 tccaggacaa tgaggtgtcg tggctcgggg ccgggcgggg gccgagggt tcgccgaggc
1441 ccagcctgtg ccatggatcg gcccagtaag aaccatccga aggtccctgc cagcgccggg
1501 cgcgggcgac gggtcgctct gcaaactccc aagaagtctt cgcgttgttg cgtcaagtg
1561 actcttgaaa tcgatgcccg attcggggac atatttttgg aaacccaagt ccctgtcag
1621 gattccaccg agttggcttt tgcttccttc acagatagaa ctggtgcgcg gggagcgaag
1681 gccgagcggc gccgaccctg cggtggtgga ttgcttgggg aggggacggg gaagtcgctc
1741 ctagaaattc tccctccat cctagagctt cggggtcagg attctcctg ctcagctcgg
1801 gacttttac aggcaccaaa agttattagc aacagagggg agtaggagag ggaactcctc
1861 cccccagagt aaggtagaca cccagacctc agcgctaaca ccggggcttt ctcccaacga
1921 taattaatag tcaaggccaa ccctttggc acgtttcttc ctccctccct cgcgggtggc
1981 agagttattt gattccccga ggccagaaac tttcactcga gttcgccgga gagaggccag
2041 cgccggccgt tttccgcggt gcccacacgt ctcctttttc ttcttccct cctcttcgtc
2101 gtcttcccag ccgcaggcca gtcgccagtc cgcgtagttt tgtttccttt ccatcatgca
2161 gaaaattaat cagcccggac gagaagcaga gaggagcatg gcggcctgta attaagggac
2221 gtgtgccct cggattatct cgttagttta tcaagaaaac atttattata attaattctc
2281 ggacgaggta attattgttg agcgaggaca cagcaactgg tagatgggct tcttggaaga
2341 aaaaaaaaac aaggcgtggg ggagggagaa gcgacagatt gcacgaattg accgttagat
2401 ataaggctgc gcggggggcg cgggcagtgg agcgggacct cgggcgccag gcctgcgggg
```

Figure 7

2461 ctgcggggct gcggggctgc ggggctgcgg ggctgccggg caggaacgcg ggacccaggc
2521 actcgcgccc ggaggtgcgg tcgccgaccg gctgccggaa ctcgccgcgc gaccgcggtc
2581 agcttctagg tatgagttct ccagaggcca cctcgtgagc agtcatagtg aggcgtggat
2641 ttttcaaaag ttatttcttt tccccgttct ggaccctgct tcgagaggaa aagagctttg
2701 aaagttagat tgaagggccc atgccttcta tgcagagtgc atacctaggc cggttgtgga
2761 gagaatctct tagttttggg ttttggtttt cctcttttcc ttttaaaggt ggatccagga
2821 gcaaaagtga aaatagtcta ttttgagaat tttagccatt ttgcaatggt aagggcaaag
2881 gagcccctgg aaggatctcg gccctggtgc tttctgtgtg ttactggctt tttatgttgg
2941 aatgtgctac tttattgtat gatgtgtcag gcatttctaa ttgggtgaga gctctacatg
3001 taagaacatt tccatatttc tcaagggtac atctgatatg attttacgat tctctatagc
3061 actgtagttc agaattttgc aaggtagtac gattaaacaa aaaatctcca atctccagtt
3121 tagaggctgt ttaaacacat atacaactgt attttaaagc tgtcgcatat gtgtttaaac
3181 agcctctaag ctggagattt ttgtttattt tcgcagcctc caaagaacag cattttgaaa
3241 agaaaagaca atacaaaaac ataaagtctg tattgtaggg gcaactaaat tagttgtact
3301 gaggataata caaactcctc caagaaagac atttataaaa ttatattaag ttagatctta
3361 gggtagaaaa gcatgacttt tgtgctctga atttaaatca gaaagaagtt gcagttacta
3421 agtttcattt atggactttt gtgccttgct gtcttaagca acgtaaatat gaaaacccgg
3481 agtcctttaa agtcagtgag accttatct tgtatccgcc attttgaagc aatctctcat
3541 ggtgtcaaag tttcaaagta gagatcctg catataagtg ccacatttta ggaaaataaa
3601 ggccagactt gcaaactgcc agtctatatt aacatctact ttgaatctct ttgctggggt
3661 ggaggcgggg agctcagctg aagaaagtaa ataacttttc tttttcttcc tttcttttcc
3721 cccttgagct cttttctta taggatgta ggaaacttga aaggtaggga gaaattctac
3781 tagtttcaca actttgggtg tttgtgtatc tacttcttc aaaactaaaa tgtgcaaaag
3841 gcagttagag ttaacaggaa actctgctgc agctgccgag gacccaaatg tctgaaaatt
3901 tgcctcccgc aggatctgca gcctccacac atcaaaatca acatggaagc agcttgcact
3961 acaaatgtgg ggtcccgtca ttatctgatt ggtgggatc taacttact tcacaatttc
4021 tggcaagccc tgtgccaatc ttgaagactt ttttggaata tgcttaaata tttgatgggt
4081 gtctattaaa agttaaatac ttgtttgttt agctttcgtt ccttagacac atataatcaa
4141 gattctccaa aaccctaata aatctgttac ttacctcgaa atctaattac ccagactact
4201 aattaggtga aaatgattac cggaaatgac ttcaaatgtg gaataatagt ggttgagcgg
4261 ttttttccaag tttgtggttt agtgagttgg tatttagat gttaaacgca ctgacatttt
4321 aggttcgcag cagttgaaag tggtaaaaag ctaagataat taaaatctct gccatggaaa
4381 ggcaacagtc tggggagagg tagatttctt gaattgtttc tttgtttctc accaatgggc
4441 tttgttatca gcattattta tttagccaaa gagttctttg tctctgcaaa tggccccaat
4501 caagttttgt ttgagacaat tagctagtgc cagccaatga gtcctatgca aatgtaggga
4561 taggaatgca atgtgtgcat ttgaaggcac gggttttgt tcttggggaa ggcagattgt
4621 aattgctttc ttcgggtact tttttttttt tttaagttt agggtggggg tggggaagac
4681 aggtttatct ggtctccttc catccctct agttccagag cagctggggg tggggtggg
4741 gatgggggtg ggggagtgt ctgcaagtcc tttaaaagcc tctgcctcgc ctagtccgtg
4801 ctcttttaa gttagtgctg gaacgtggaa gagctgctgc ctccgaagca gtaaaccagc
4861 ccctctgttt gtttgtttgc ttgcccctta gttccactgc tccaaaccca cccaccaagg

Figure 7 (cont)

```
4921 actctgaacc tgtccacccc gggcgcatca agatcttcca gctgggtacc cccgatttgg
4981 gccgactttg cacctccaaa caaccttagc atgatgtctt atcttaagca accgccttac
5041 gcagtcaatg ggctgagtct gaccacttcg ggtatggact tgctgcaccc ctccgtgggc
5101 tacccgggta agtgagccct gctgcactcc cgcaccccta ttccccatgc ccaccctccg
5161 gggatgcaac accctgttcc catggaacac gggggttggc agtcacactg tccccaccca
5221 gcttcaggct tggtctcctc taggtttgcc ttctgaggaa gcagtcccag ggcatttact
5281 gaccaagcag agaacagggg ttgggaaaag tgagtaggtg ggtctgcaac cgttacaatc
5341 acatcactt attcttaatt cgagtaaata aggattggca tcagagtggg atgaggaagg
5401 ttactgtcct tgtcatttgg gcaaaagacc cctacccata tctcaatgac caattcctca
5461 gaagtgtcct cttggagaag ctgagttttc cctccgtaag tccttagcac tctcgggctt
5521 cgcagttgtt ccctccatgc ccaggccttc ccctatgacc tccagagcct gctttaatcc
5581 caagaggcgt gacttcctcc aaatgcgggt gcttccttt ccaatcagat atgttaaaa
5641 atcctcccag gagtatgaac tatgtcccca ttttaaagat ggaggaacaa aggcccatgg
5701 tgtgctaaaa accatgggaa caggatccag atttccccca tcaattcgag ctgccagtct
5761 gtcctcggag atcctttgac ttcttggaat agccttttg tgttgtggtt tggggttga
5821 tcttggagaa cttttttgtg tgtcttttaa aaaatgtttc atttgttaac tttccaagtg
5881 atgctctgat tggagcaatc tcaacaccaa gaagagtagg gaaagaagca gcgtgtgtcc
5941 tgggtccccg gggagcaagg ctggggagac ggtggggaga gcattggtag gctcccggct
6001 gaagggctgt gaggaacggg ggactgctgc ggggtggagg gcagggcgt cggagaaccc
6061 gcggaaacgc ctatgactga gaaactgctc ccccacccta aagggccctg ggcttctgt
6121 cccgcagcca ccccccggaa acagcgccgg gagaggacga cgttcactcg ggcgcagcta
6181 gatgtgctgg aagcactgtt tgccaagacc cggtacccag acatcttcat gcgagaggag
6241 gtggcactga aaatcaactt gcccgagtcg agggtgcagg tagggcagat gcaggcagaa
6301 ccatccttcc tgatcatgcc accctcccg agtatgggac tgtggagagc cccaggtctt
6361 tcagaggact gaaggaaggc ttgaaattct ccttcactca ctaaggggcc aggaaactat
6421 tctccttctg ccctttttg cctgcccgtc accacttaat cccgtaagca agggtcttca
6481 aggcccgggt tgctggtgga gagagaccca tccttgagca ggtttcaaga gtagtcacgt
6541 ggtgttgtaa cccttcccctt cctctgtata gaaatcctct cctattctca tggactgta
6601 cgtgtgaaag cagcttagct cttggacagt ccaagtattt ttacagatga aaaatagag
6661 taaatgactt gctcaaggtc ataactaagt ttggtggcag agtcagggta tagacgcagc
6721 tggtgctttt accaaataaa tcaacacaaa aagaatgtat tttccttgac ttcttaggga
6781 ttgaagagaa ttttctagtt ctgagccatt taacagataa aatatctaca taatgtctct
6841 agtgacaccc ctcttgtttt agttccccta aacttgacct taaactggag agggaaggtc
6901 aactccagct tgcctgtga gtgagccctg tacagaattc tctgcaaagt gtttagcaca
6961 taaaccacat acacacctgg gcctctcctt cggctagaat atgtttatga aagcgacaga
7021 catcagtgtc agctgcaaat tgggaaaggg gcttttcaa agtaggttag aggaagtttt
7081 agcacttgca aggcttgaac caaagtcctc actaggagaa aacaaatggc tccaaatggt
7141 tggtggtctt gagcttggcc ttggtggcct cactttacc acagttacgg cacccataca
7201 gagagctcat tcaaaagttc agctaaggat ttgtcctcca gaaaatgcca gtagttcctc
7261 ttctaagccc cctcgtacac caatcatagc tccttcattg cagaacatga acagggctgg
7321 taaagagaat tgtcaagatt gcagcagggg gttgaagtgg taagtcagta aacacagcac
```

```
7381 aggagactga gtctatgtgc tgagtggcac tactctaaca acacagactc gagtcccaga
7441 gactagcagg tctgtgctcc agctcaaagc agagtgcatg taagtcactc cttttaccac
7501 aaagaagctt ttagcaaata gtggctttca gacctcttc ttcaacaaga tcatgtcttc
7561 ccctggagc tttgttctgt gagtcttct aagagagaca gaagggtgat ggaaccaacc
7621 aacctctata ttagcagttg cttcctggaa gatgaactgt aaatgaattt aggctgttcc
7681 tgttagcctg taacaacaga attgctttct ctcacttctc atgtatttcc ctccaaaaga
7741 cagagataca ttctattcct ctgtgagagt gttccaaaat atagctgggt ctatgtgtat
7801 gtgtgtgtta gaggcgaaat aagataggaa agtgatgtgg agagttttta gctatatgat
7861 ttgggggatt atcttaaatg ttattctggg caagaaataa gacagtgtca agtgttttta
7921 gacagagcct ccccaacttt cttacaagtc caggagttta tatgagagta ccacataata
7981 ggtcttcagt ggcaggggaa attgtgtgtt tagctgatct gcccatgtag gatagattta
8041 taatacggga gccattcttg tccttaagga actatcaaaa ccgagttaaa gaattttctt
8101 tcccttccaa ggtatggttt aagaatcgaa gagctaagtg ccgccaacaa cagcaacaac
8161 agcagaatgg aggtcaaaac aaagtgagac ctgccaaaaa gaagacatct ccagctcggg
8221 aagtgagttc agagagtgga acaagtggcc aattcactcc cccctctagc acctcagtcc
8281 cgaccattgc cagcagcagt gctcctgtgt ctatctggag cccagcttcc atctccccac
8341 tgtcagatcc cttgtccacc tcctcttcct gcatgcagag gtcctatccc atgacctata
8401 ctcaggcttc aggttatagt caaggatatg ctggctcaac ttcctacttt gggggcatgg
8461 actgtggatc atatttgacc cctatgcatc accagcttcc cggaccaggg gccacactca
8521 gtcccatggg taccaatgca gtcaccagcc atctcaatca gtccccagct tctctttcca
8581 cccagggata tggagcttca agcttgggtt ttaactcaac cactgattgc ttggattata
8641 aggaccaaac tgcctcctgg aagcttaact tcaatgctga ctgcttggat tataaagatc
8701 agacatcctc gtggaaattc caggttttgt gaagacctgt agaacctctt tttgtgggtg
8761 attttttaaat atactgggct ggacattcca gttttagcca ggcattggtt aaaagagtta
8821 gatgggatga tgctcagact catctgatca aagttccgag aggcatagaa ggaaaaacga
8881 agggccttag aggggcctac aaaccagcaa catgaaatgg acaaaccaat ctgcttaaga
8941 tcctgtcata gttttagatc attggttatc ctgattgca aagtgatcaa aagcattcta
9001 gccatgtgca accaaacacc accaaaaata aaatcaaaca aaactaagtt gtgaaggaag
9061 ggagggaagg tcatagcctt cttaagcaga ggtgttccat tgttttagcc aatccttggt
9121 tgaatcttag gaatgaacag tgtctcaagc tcattcacgt ttcatgacca actggtagtt
9181 ggcactgaaa aaacttttca gggctgtgtg aattgtgtga ctgattgtcc tagatgcact
9241 actttattta aaaataatg ttcataagga gtcaatatgt agtttaagag acaatcagtg
9301 tgtgtcttat aaatggtaca tctgtggttt ttaatctgtg ctagacttca aaactgtgat
9361 ctcctgttat tgtatgcaac cttgaactcc acctctgcag gggttcttct gtgattaaat
9421 aggttataat tataagcaaa attcagagca actgagtact gatctaaaaa gattaccttt
9481 ggctggaggt gagctgcact gaaacttac gacaaaatgt ctctggacaa agagagtcag
9541 agaagagaag caaaaggaca ctaattcatc tgtaatttac tgttggtaag cctagcagta
9601 aagagacatt ggtcaattgc tctgaccctg atgaattatt aaactgagat cattgtcgtt
9661 tatgcttgca gatgttaaat ggaaaagtta tatatgcata aaccttttct tcctggattt
9721 ggcagatatg tataattata ttaaaatggt tctagcacaa
```

Figure 7 (cont.)

SEQUENCE LISTING

<160> NUMBER OF SEQ ID NOS: 3

<210> SEQ ID NO 1
<211> LENGTH: 6834
<212> TYPE: DNA
<213> ORGANISM: Homo sapiens

<400> SEQUENCE: 1

| | | | | | | |
|---|---|---|---|---|---|---|
| tgctgccatg | tgccgctgcc | acgggtaccc | agcctgtcgc | taaactttcc | gggcgccagc | 60 |
| ccggctctga | gtcgcgcttc | tcagcggagt | gacccaggga | cggaggaccc | aggctggctg | 120 |
| gggactgtct | gctcttctcg | gcgggatccg | tggaggtgag | aaccttccct | ttctccctgt | 180 |
| tcttctcccg | tttcctgtgc | ccttttccgg | gaagctgagg | gttctggtct | ccggcactg | 240 |
| cctgaagggc | ccagcttgga | aagagagggt | ggggagtcg | gtagtttggt | tacaggaggc | 300 |
| ggagcgggga | ggaaaggaaa | ggggttaact | taagagattt | ggagacagct | cgcggggacc | 360 |
| gaactgttga | cgcctctcca | acagggagtg | gttgcaatct | ttcttctccc | ccttcttttt | 420 |
| taaagagtcc | tttccctgga | atccgagccc | taaccgtctc | tccccagccc | tatccggcga | 480 |
| ggagcggagc | gctgccagcg | gaggcagcgc | cttcccgaag | cagtttatct | ttggacggtt | 540 |
| ttctttaaag | gaaaaagcaa | ccaacaggtt | gccagccccg | gcgccacaca | cgagacgccg | 600 |
| gagggagaag | ccccggcccg | gattcctctg | cctgtgtgcg | tccctcgcgg | gctgctggag | 660 |
| gcgaggggag | ggaggggggcg | atggctcggc | ctgacccatc | cgcgccgccc | tcgctgttgc | 720 |
| tgctgctcct | agcgcagctg | gtgggccggg | cggccgccgc | gtccaaggcc | ccggtgtgcc | 780 |
| aggaaatcac | ggtgcccatg | tgccgcggca | tcggctacaa | cctgacgcac | atgcccaacc | 840 |
| agttcaacca | cgacacgcag | gacgaggcgg | gcctggaggt | gcaccagttc | tggccgctgg | 900 |
| tggagatcca | atgctcgccg | gacctgcgct | tcttcctatg | ctctatgtac | acgcccatct | 960 |
| gtctgcccga | ctaccacaag | ccgctgccgc | cctgccgctc | ggtgtgcgag | cgcgccaagg | 1020 |
| ccggctgctc | gccgctgatg | cgccagtacg | gcttcgcctg | gcccgagcgc | atgagctgcg | 1080 |
| accgcctccc | ggtgctgggc | cgcgacgccg | aggtcctctg | catggattac | aaccgcagcg | 1140 |
| aggccaccac | ggcgcccccc | aggcctttcc | cagccaagcc | cacccttcca | ggcccgccag | 1200 |
| gggcgccggc | ctcgggggc | gaatgccccg | ctggggccc | gttcgtgtgc | aagtgtcgcg | 1260 |
| agcccttcgt | gcccattctg | aaggagtcac | accgctcta | caacaaggtg | cggacgggcc | 1320 |
| aggtgcccaa | ctgcgcggta | ccctgctacc | agccgtcctt | cagtgccgac | gagcgcacgt | 1380 |
| tcgccacctt | ctggatagc | ctgtggtcgg | tgctgtgctt | catctccacg | tccaccacag | 1440 |
| tggccacctt | cctcatcgac | atggaacgct | tccgctatcc | tgagcgcccc | atcatcttcc | 1500 |
| tgtcagcctg | ctacctgtgc | gtgtcgctgg | gcttcctggt | gcgtctggtc | gtgggccatg | 1560 |
| ccagcgtggc | ctgcagccgc | gagcacaacc | acatccacta | cgagaccacg | ggccctgcac | 1620 |
| tgtgcaccat | cgtcttcctc | ctggtctact | tcttcggcat | ggccagctcc | atctggtggg | 1680 |
| tcatcctgtc | gctcacctgg | ttcctggccg | ccggcatgaa | gtgggcaac | gaggccatcg | 1740 |
| cgggctacgc | gcagtacttc | cacctggctg | cgtggctcat | ccccagcgtc | aagtccatca | 1800 |
| cggcactggc | gctgagctcc | gtggacgggg | acccagtggc | cggcatctgc | tacgtgggca | 1860 |
| accagaacct | gaactcgctg | cgcggcttcg | tgctgggccc | gctggtgctc | tacctgctgg | 1920 |
| tgggcacgct | cttcctgctg | gcgggcttcg | tgtcgctctt | ccgcatccgc | agcgtcatca | 1980 |
| agcagggcgg | caccaagacg | gacaagctgg | agaagctcat | gatccgcatc | ggcatcttca | 2040 |
| cgctgctcta | cacggtcccc | gccagcattg | tggtggcctg | ctacctgtac | gagcagcact | 2100 |

```
accgcgagag ctgggaggcg gcgctcacct gcgcctgccc gggccacgac accggccagc    2160
cgcgcgccaa gcccgagtac tgggtgctca tgctcaagta cttcatgtgc ctggtggtgg    2220
gcatcacgtc gggcgtctgg atctggtcgg gcaagacggt ggagtcgtgg cggcgtttca    2280
ccagccgctg ctgctgccgc ccgcggccgcg gccacaagag cggggggcgcc atggccgcag    2340 gggactaccc cgaggcgagc gccgcgctca caggcaggac cgggccgccg ggccccgccg    2400
ccacctacca caagcaggtg tccctgtcgc acgtgtagga ggctgccgcc gagggactcg    2460
gccggagagc tgaggggagg ggggcgtttt gtttggtagt tttgccaagg tcacttccgt    2520
ttaccttcat ggtgctgttg ccccctcccg cggcgacttg gagagaggga agaggggcgt    2580
tttcgaggaa gaacctgtcc caggtcttct ccaaggggcc cagctcacgt gtattctatt    2640 ttgcgttttct tactgccttc tttatgggaa ccctcttttt aatttatatg tattttctt     2700 aatttgtaac tttgttgcat tttggcaaca atttaccttt gctttggggg ctttacaatc    2760
ctaaggttgg cgttgtaatg aagttccact tggttcaggt ttctttgaac tgtgtggtct    2820
caattgggaa aatatatttc ctatacgtgt gtctttaaaa aaaaatgtga acagtgaacg    2880
tttcggttgc tgtgactggg aagttgttgg gtgtgcttttt tcagccagct tctccttcca    2940
ctgcttaaag tgtccatgat tctttaaggt gagctgcagt ttatagcccc aggtcatacc    3000
taggagggga gcataatgag ctcagggcct ccccaaagtg acaaggttag ggagtgctta    3060
gcggttttgt gttcagcctt agctttgttt atagagggag gttcagtttc ttttctgtag    3120
tgcttgtaat aattctcact cctaacagca ccatcgttgt gtcttgaata agttagaggt    3180
agcattatag aggatctggc ataaatattt gcagtagtga gagcctaagc gatggtgatt    3240
ggtggagctt gaattttagg ctggtgagat ggcagctttg tgcctgagag gtagtgggtg    3300
gttcttaagc ttcagtgatc ccctttttttt tttttttttt tttttttttaa ggaacttgtg   3360 ttataatttt ggtaaaagta taaacccact ccctctggac aatacttagc gacagttgct    3420 aaaggggggct ccttttttaaa tgtaaggact gaaatggata tacttctaat aagtaaattt    3480
ccaacactta tttgctccac cccctccccc ctcccccctc cccctttatc atgttaaaca    3540
gcctttttgc ttttcttatt cctcctctcc tggagagctg tgattagaaa ccacacccac    3600
ccttgaatga agtgcttgaa ctgggggagg gaggctggct acctgtgaac aaacattggc    3660
ccaaataagg gaaataagt gttcctggac tttggactag tttatagcca gatattccaa    3720
gagcagcaag acgttgctct ctgccgtctc tgaaaacaaa agagatgcat aacatgcttg    3780 cacaacctttt taaaatatag atcagtatag tgctacctct atagtttttct tcctcttctg    3840 agaaagcctg tatattgatg atcacacaca cacacacttt gcaattagag aatttggttt    3900
gctttactaa tctgtttaac tattccttca ttcattatga acgcttatat tgatgaacat    3960
acacacagag gtttctttgc tattagaaaa ttctgtttgc tttcctaatc tgtttaagca    4020
ttcattcatg aagagtgtgg ggccattact ggggaagggg ggtgacagtg cctcagccag    4080
caaaatacca atgaccagga ttggggacta aatttaggaa gctaaaatgg ccagagcaat    4140
taacatttga gaaaatcctg tctaggaaaa caacttgagt gtaggcattt gtaattcact    4200
tataccaaag ttggaaaagt aaaatttaag cctaggacaa ttttttacttc atggatgtta    4260 aatagacaaa tgcatagttc caggggggaa tttaaacact ttactggtgg gaagaaacct    4320
agtattaaag ttgtaaggac tctcaaaaac ttcacattta ttaaaatgca ctgctcttac    4380
ccaatttatc ctctgaatta aaatttcagt ggattctaca aaacctcgta caaatagcta    4440
```

```
cagaactttg tgcctatttt attcctctat ttattcttct aggaagaagc ctcttcctag    4500
aatcttgaaa tagatccctt gactgaatgc caattcctct cctgttttc aaatgagaga    4560 accttttctg atcaccttga ccttttccct catttcatat gtcttcccag aaagtagaca    4620
gactgctctg ctgccttcag tcattgtgcc tcatttgggt tgtccctcct tctttgtgga    4680
gaaatctgga aatgatgcac agtgtatcca aaagttgtgg gatgaagtgg atgaaagtga    4740
tttaattcat ttttagaatt ttttttttgtt ttgttttagc aacatgctga acaactaatt    4800
tactttaaaa ataagccagt taaaacaaag gacgctaagc ccaagtgggg ggcaatatta    4860
gtcaggatct ttggggtcta attccagacc aactttcaga agcacttctt tgtctctgtt    4920
ctcacctctg ctgtccctct cttccctcat cccctaagag agacaaagat aaaagcccac    4980
ctgcatccct aagtcttact gagatcagcc accccagggg agagaaactg gatctactta    5040
cagccacccc ctgtttccat ccatatagtt acttccccca atttgcatgt gattatggaa    5100
acaagtcatg ctcatgaaag caactgtaaa ataaaaggtt atggagtagt tcagcaactt    5160
cttcacagcc agctttgtgg agctggggag gacttagggc ccattggagt ctcttatgtg    5220
tacagcttca gggctgtccc tttcagtttg attttaagca atgcctcact tcatagctta    5280
gggggtaagg attccattca ggtaggttgt ctaaggaaac taatgggacc tctcagtgaa    5340
ttagctgacc agattttagg aaatctttt aatttctatg attttccttc tcacattttg    5400
aaatggtaaa attgactgga ataattttt cttggtgcct tattggtttt ccttgcaaac    5460
ctttctcata ttttctcatg accattgcca gtgaccaagg cccatgtgtg tgttgtgtgt    5520
aattgtgggc atgtacaagc ttaaataacg tgccgacagc actgtttcaa agttggtatt    5580
cattaggctg ttgcctcctg ggctggagct gcgctaatcc tgacaccggc tgccaggaga    5640
aaacctcatg gatcacacac caaaccttaa taacagcatc cgtgacctgc actctccagt    5700
acagaatggg aaccccagag ctaggaaatg tagttgtata ttttaatgaa ctgctacccc    5760
agccaaagaa gcttctttca cttttgtgct ctacagaaag cccaaggggg gtaggaggga    5820
cagagctttg aataactgct ttctaacact aaatgtggcc aacaggacag agcacatcac    5880
acgtataggc aggtgtgagg gacagtggct aagaattgcc tgctccctct gcatgctctt    5940 tcttgttcc aaagtccaat caagtgatcc tgggaaacaa atctgtctgg attgcggagg    6000
gtggttctga aagaactgcc aagacgttaa agaagggtga agagtaggca gaatataagt    6060
agctaacctg agtcaagact ctcaaaagct agcagcctga tgacaatagg atttatttca    6120
gccaggatag tgtctgtctg tgagtgcatc attttaagac agtatgactt catgttgtta    6180
caaactatgt atagtatgta tgttttgtgg gttgtatata tacataatat atattatata    6240
tatatatgag agatttggtg acttttgata cgggtttggt gcaggtgaat ttattactga    6300
gccaaatgag gcacataccg agtcagtagt tgaagtccag ggcattcgat actgtttatg    6360
atttccatat atgtatagtg cctatcccat gctgtagtca ctgttatgtt aaatccagaa    6420
gttacactag agccagcgat actttatttg tagacaatca atttgaatcc atatgttatt    6480
actggcagat gatacatgat tacagttctg aatctgtaac acttacaaaa ggaaacccag    6540
agcagcttga tgagttttg tttctgcttc gttcctggga gtcagtagaa acagcagttg    6600
tatgtggtta tgttagtctc aagatactta atttgttgac cttacttcag aaaaattttg    6660
tatgtattat atttgtggga aggtaaaata atcatttgag atttttatca aatatgaaga    6720
ttagttattt atgaaaaaca aagaaatgtc tattttcctt tgttcccaat taatgtgat    6780 aaatttaaa atgcattaaa gtaatggtaa agacaataaa aagatgctgt agaa          6834
```

<210> SEQ ID NO 2
<211> LENGTH: 4942
<212> TYPE: DNA
<213> ORGANISM: Homo sapiens

<400> SEQUENCE: 2

```
aaatcatccg tagtgcctcc ccgggggaca cgtagaggag agaaaagcga ccaagataaa      60
agtggacaga agaataagcg agactttta tccatgaaac agtctcctgc cctcgctccg      120
gaagagcgct gccgcagagc cgggtcccca agccggtct tgagagctga tgacaataac      180
atgggcaatg gctgctctca gaagctggcg actgctaacc tcctccggtt cctattgctg      240
gtcctgattc catgtatctg tgctctcgtt ctcttgctgg tgatcctgct ttcctatgtt      300
ggaacattac aaaaggtcta ttttaaatca aatgggagtg aacctttggt cactgatggt      360
gaaatccaag ggtccgatgt tattcttaca aatacaattt ataaccagag cactgtggtg      420
tctactgcac atcccgacca acacgttcca gcctggacta cggatgcttc tctcccaggg      480
gaccaaagtc acaggaatac aagtgcctgt atgaacatca cccacagcca gtgtcagatg      540
ctgccctacc acgccacgct gacacctctc ctctcagttg tcagaaacat ggaaatggaa      600
aagttcctca gttttcac atatctccat cgcctcagtt gctatcaaca tatcatgctg      660
tttggctgta ccctcgcctt ccctgagtgc atcattgatg gcgatgacag tcatggactc      720
ctgccctgta ggtccttctg tgaggctgca aaagaaggct gtgaatcagt cctggggatg      780
gtgaattact cctggccgga tttcctcaga tgctcccagt ttagaaacca aactgaaagc      840
agcaatgtca gcagaatttg cttctcacct cagcaggaaa acggaaagca attgctctgt      900
ggaaggggtg agaactttct gtgtgccagt ggaatctgca tccccgggaa actgcaatgt      960
aatggctaca cgactgtga cgactggagt gacgaggctc attgcaactg cagcgagaat      1020
ctgtttcact gtcacacagg caagtgcctt aattacagcc ttgtgtgtga tggatatgat     1080
gactgtgggg atttgagtga tgagcaaaac tgtgattgca atcccacaac agagcatcgc     1140
tgcgggacg ggcgctgcat cgccatggag tgggtgtgtg atggtgacca cgactgtgtg     1200
gataagtctg acgaggtcaa ctgctcctgt cacagccagg gtctggtgga atgcagaaat     1260
ggacaatgta tccccagcac gtttcaatgt gatggtgacg aggactgcaa ggatgggagt     1320
gatgaggaga actgcagcgt cattcagact tcatgtcaag aaggagacca agatgcctc     1380
tacaatccct gccttgattc atgtggtggt agctctctct gtgacccgaa caacagtctg     1440
aataactgta gtcaatgtga accaattaca ttggaactct gcatgaattt gcctacaac     1500
agtacaagtt atccaaatta ttttggccac aggactcaaa aggaagcatc catcagctgg     1560
gagtcttctc ttttcctgc acttgttcaa accaactgtt ataataccct catgttcttt     1620
tcttgcacca tttggtacc aaaatgtgat gtgaatacag gcgagcatat ccctccttgc     1680
agggcattgt gtaacactc taagaacgc tgtgagtctg ttcttgggat tgtgggccta     1740
cagtggcctg aagacacaga ttgcagtcaa tttccagagg aaaattcaga caatcaaacc     1800
tgcctgatgc ctgatgaata tgtggaagaa tgctcaccta gtcatttcaa gtgccgctca     1860
ggacagtgtg ttctggcttc cagaagatgt gatggccagg ccgactgtga cgatgacagt     1920
gatgaggaaa actgtggttg taaagagaga gatctttggg aatgtccatc caataaacaa     1980
tgtttgaagc acacagtgat ctgcgatggg ttcccagact gccctgatta catggacgag     2040
aaaaactgct cattttgcca agatgatgag ctggaatgtg caaccatgc gtgtgtgtca     2100
```

-continued

```
cgtgacctgt ggtgtgatgg tgaagccgac tgctcagaca gttcagatga atgggactgt    2160
gtgaccctct ctataaatgt gaactcctct tcctttctga tggttcacag agctgccaca    2220
gaacaccatg tgtgtgcaga tggctggcag agatattga gtcagctggc ctgcaagcag     2280
atgggtttag gagaaccatc tgtgaccaaa ttgatacagg aacaggagaa agagccgcgg    2340
tggctgacat tacactccaa ctgggagagc ctcaatggga ccactttaca tgaacttcta    2400
gtaaatgggc agtcttgtga gagcagaagt aaaatttctc ttctgtgtac taaacaagac    2460
tgtgggcgcc gccctgctgc ccgaatgaac aaaaggatcc ttggaggtcg acgagtcgc    2520
cctggaaggt ggccatggca gtgttctctg cagagtgaac ccagtggaca tatctgtggc    2580
tgtgtcctca ttgccaagaa gtgggttctg acagttgccc actgcttcga ggggagagag    2640
aatgctgcag tttggaaagt ggtgcttggc atcaacaatc tagaccatcc atcagtgttc    2700
atgcagacac gctttgtgaa gaccatcatc ctgcatcccc gctacagtcg agcagtggtg    2760
gactatgaca tcagcatcgt tgagctgagt gaagacatca gtgagactgg ctacgtccgg    2820
cctgtctgct tgcccaaccc ggagcagtgg ctagagcctg acacgtactg ctatatcaca    2880
ggctggggcc acatgggcaa taaaatgcca tttaagctgc aagagggaga ggtccgcatt    2940
atttctctgg aacattgtca gtcctacttt gacatgaaga ccatcaccac tcggatgata    3000
tgtgctggct atgagtctgg cacagttgat tcatgcatgg gtgacagcgg tgggcctctt    3060
gtttgtgaga agcctggagg acggtggaca ttatttggat taacttcatg gggctccgtc    3120
tgcttttcca aagtcctggg gcctggcgtt tatagtaatg tgtcatattt cgtcgaatgg    3180
attaaaagac agatttacat ccagaccttt ctcctaaact aattataagg atgatcagag    3240
acttttgcca gctacactaa agaaaatgg ccttcttgac tgtgaagagc tgcctgcaga    3300
gagctgtaca gaagcacttt tcatggacag aaatgctcaa tcgtgcactg caaatttgca    3360
tgtttgtttt ggactaattt ttttcaattt attttttcac cttcattttt ctcttatttc    3420
aagttcaatg aaagacttta caaaagcaaa caaagcagac tttgtccttt tgccaggcct    3480
aaccatgact gcagcacaaa attatcgact ctggcgagat ttaaaatcag gtgctacagt    3540
aacaggttat ggaatggtct ctttatcct atcacaaaaa aagacataga tatttaggct    3600
gattaattat ctctaccagt ttttgtttct caagctcagt gcatagtggt aaatttcagt    3660
gttaacattg gagacttgct tttctttttc ttttttttata ccccacaatt cttttttatt   3720
acacttcgaa tttagggta cacgagcaca acgtgcaggt tagttacata tgtatacatg    3780
tgccatgttg gtgtgctgaa cccagtaact cgtcatttga tttattaaaa gccaagataa    3840
tttacatgtt taaagtattt actattaccc ccttctaatg tttgcataat tctgagaact    3900
gataaaagac agcaataaaa gaccagtgtc atccatttag gtagcaagac atattgaatg    3960
caaagttctt tagatatcaa tattaacact tgacattatt ggaccccca ttctggatgt    4020
atatcaagat cataatttta tagaagagtc tctatagaac tgtcctcata gctgggtttg    4080
ttcaggatat atgagttggc tgattgagac tgcaacaact acatctatat ttatgggcaa    4140
tattttgttt tacttatgtg gcaaagaact ggatattaaa ctttgcaaaa gagaatttag    4200
atgagagatg caatttttta aaagaaaat taatttgcat ccctcgttta attaaattta    4260
tttttcagtt ttcttgcgtt catccatacc aacaaagtca taaagagcat attttagagc    4320
acagtaagac tttgcatgga gtaaaacatt ttgtaatttt cctcaaaaga tgttttaatat   4380
ctggtttctt ctcattggta attaaaattt tagaaatgat ttttagctct aggccacttt    4440
acgcaactca atttctgaag caattagtgg taaaaagtat ttttccccac taaaaaactt    4500
```

-continued

```
taaaacacaa atcttcatat atacttaatt taattagtca ggcatccatt ttgccttttta   4560 aacaactagg attccctact aacctccacc agcaacctgg actgcctcag cattccaaat   4620
agatactacc tgcaatttta tacatgtatt tttgtatctt ttctgtgtgt aaacatagtt   4680
gaaattcaaa aagttgtagc aatttctata ctattcatct cctgtccttc agtttgtata   4740
aacctaagga gagtgtgaaa tccagcaact gaattgtggt cacgattgta tgaaagttca   4800
agaacatatg tcagttttgt tacagttgta gctacatact caatgtatca acttttagcc   4860
tgctcaactt aggctcagtg aaatatatat attatactta ttttaaataa ttcttaatac   4920
aaataaaatg gtaatggtct aa                                           4942

<210> SEQ ID NO 3
<211> LENGTH: 9760
<212> TYPE: DNA
<213> ORGANISM: Homo sapiens

<400> SEQUENCE: 3
gagagcggga ccggcctcag ctccaacaca gcctccactg tgattaaaaa taaaaattgc     60
tagagcagcc ctcactcgcc acatctactt tgtatgtatt gcagaggggc ccacgcgtgt    120
ttagaactct agccgccttc ctcattttcg ttctttaaaa aaaatttttt ttggttgtgt    180 ttgactttc atggaagggt gaagactgca aggtttctaa ctcaatactc ttgatttctt    240
ttaggatagc tggctatttg gaatttaaag gatatttgac tttttctaac ctcccatgag    300
gctgtaaggt aagtgtccgt ctgtcttgtc tatatccata tctacgtgtc cccgtgtctg    360
tcggccatca ccccagtacc tccaatagac cgaccgatgc ccctctgcga acgtggagtt    420
ctgtaggcgg atgtattttt tctcttacaa attttgaggt gtaataacga tcgttgcaaa    480
aagaaaaatg tgatctagag atgagagcgg tagtgggaga gaggcagaga gcgtgctcct    540
gggggtcgtc gcttctgcaa aacgtcgtcg aaacgctgcg aatgtaatct ggggtgtttt    600
ggaaggtttt gtttgtggtt ttgttttat gtcaacgccg ttctgggctt ctcccgcgat    660
ctttgcgttt tggcccccag atttggttgg ggtcgtttgg atggatccca gggaccttt    720 tagagtccga gacaaaaaga tgcagatgta actagatgga tggattgaaa caacaataat    780
aaaaagccag gcgcctcctt gggcccgcgc gccggaagct cggttcgctt gcgggtcggc    840
ctgggccggg ggccgccgct cgagcccctg tcggcccctg ttgaacgtga gcggaaaccg    900
gagcggataa ccgaggaggc tgggagcgct ggcttctcgt ccgccccggc gctcactgct    960
cgctctcttt ggcctcctct ccctcagcct agcacagctc ggttgtctgt ttctcccaaa   1020
agcttccaga tctccttttt gtttttaaat atccaccacc ccccaaaatc caaaccaccc   1080
tgggttgtaa ttacgcagcc tcccaacccc cggttgtcgt ggtccccgac cctggtcacc   1140
aggccgagcg aacgtgaaga gtgttttttc aacatgactt tgccgggtcg cggcccgccc   1200
cacgtagccc tccgcgcgca cctggggcgg gcagaagtgg cagctagtgg cccctgctcc   1260
gcccaaggcc gcggccgggc cagggaccgg aatcctcccg ctgggaccgc ggcccctcag   1320
ctgttctctg gcggggagag gcagggctcg cccgcgcgct cgcgcacccc cttcccaggc   1380
tccaggacaa tgaggtgtcg tggctcgggg ccgggcgggg gccgagggggt tcgccgaggc   1440 ccagcctgtg ccatggatcg gcccagtaag aaccatccga aggtccctgc cagcgccggg   1500
cgcgggcgac gggtcgctct gcaaactccc aagaagtctt cgcgttgttg cgttcaagtg   1560
actcttgaaa tcgatgcccg atttcgggac atatttttgg aaacccaagt cccctgtcag   1620
```

```
gattccaccg agttggcttt tgcttccttc acagatagaa ctggtgcgcg gggagcgaag    1680
gccgagcggc gccgaccctg cggtggtgga ttgcttgggg aggggacggg gaagtcgctc    1740
ctagaaattc tcccctccat cctagagctt cggggtcagg atttctcctg ctcagctcgg    1800 gacttttac aggcaccaaa agttattagc aacagagggg agtaggagag ggaactcctc    1860
cccccagagt aaggtagaca cccagacctc agcgctaaca ccggggcttt ctcccaacga    1920
taattaatag tcaaggccaa ccctttggc acgtttcttc ctccctccct cgcgggtggc    1980
agagttattt gattccccga ggccagaaac tttcactcga gttcgccgga gagaggccag    2040
cgccggccgt tttccgcggt gcccacacgt ctccttttc tttctttcct cctcttcgtc    2100
gtcttcccag ccgcaggcca gtcgccagtc cgcgtagttt tgtttccttt ccatcatgca    2160
gaaaattaat cagcccggac gagaagcaga gaggagcatg gcggcctgta attaagggac    2220
gtgtgcccct cggattatct cgttagttta tcaagaaaac atttattata attaattctc    2280
ggacgaggta attattgttg agcgaggaca cagcaactgg tagatgggct tcttggaaga    2340 aaaaaaaac aaggcgtggg ggaggagaa gcgacagatt gcacgaattg accgttagat    2400
ataaggctgc gcggggggcg cgggcagtgg agcgggacct cgggcgccag gcctgcgggg    2460
ctgcggggct gcgggctgc ggggctgcg ggctgccggg caggaacgcg ggacccaggc    2520
actcgcgccc ggaggtgcgg tcgccgaccg gctgccggaa ctcgccgcgc gaccgcggtc    2580
agcttctagg tatgagttct ccagaggcca cctcgtgagc agtcatagtg aggcgtggat    2640
ttttcaaaag ttatttcttt tccccgttct ggaccctgct tcgagaggaa aagagctttg    2700
aaagttagat tgaagggccc atgccttcta tgcagagtgc atacctaggc cggttgtgga    2760
gagaatctct tagttttggg ttttggtttt cctcttttcc ttttaaaggt ggatccagga    2820
gcaaaagtga aaatagtcta ttttgagaat tttagccatt ttgcaatggt aagggcaaag    2880
gagcccctgg aaggatctcg gccctggtgc tttctgtgtg ttactggctt tttatgttgg    2940
aatgtgctac tttattgtat gatgtgtcag gcatttctaa ttgggtgaga gctctacatg    3000
taagaacatt tccatatttc tcaagggtac atctgatatg attttacgat tctctatagc    3060
actgtagttc agaattttgc aaggtagtac gattaaacaa aaaatctcca atctccagtt    3120
tagaggctgt ttaaacacat atacaactgt attttaaagc tgtcgcatat gtgtttaaac    3180
agcctctaag ctggagattt tgtttatttt tcgcagcctc caaagaacag catttttgaaa    3240 agaaaagaca atacaaaaac ataaagtctg tattgtaggg gcaactaaat tagttgtact    3300
gaggataata caaactcctc caagaaagac atttataaaa ttatattaag ttagatctta    3360
gggtagaaaa gcatgacttt tgtgctctga atttaaatca gaaagaagtt gcagttacta    3420
agtttcattt atggacttt tgtgccttgct gtcttaagca acgtaaatat gaaacccgg    3480 agtcctttaa agtcagtgag acctttatct tgtatccgcc attttgaagc aatctctcat    3540
ggtgtcaaag tttcaaagta gagatccttg catataagtg ccacattta ggaaaataaa    3600 ggccagactt gcaaactgcc agtctatatt aacatctact ttgaatctct ttgctggggt    3660
ggaggcgggg agctcagctg aagaaagtaa ataacttttc tttttcttcc tttctttcc    3720 cccttgagct cttttttctta taggattgta ggaaacttga aagtaggga gaattctac    3780 tagtttcaca acttttgggtg tttgtgtatc tactttcttc aaaactaaaa tgtgcaaaag    3840
gcagttagag ttaacaggaa actctgctgc agctgccgag gacccaaatg tctgaaaatt    3900 tgcctccgc aggatctgca gcctccacac atcaaaatca acatggaagc agcttgcact    3960
acaaatgtgg ggtcccgtca ttatctgatt ggtgggattc taactttact tcacaatttc    4020
```

```
tggcaagccc tgtgccaatc ttgaagactt ttttggaata tgcttaaata tttgatgggt    4080
gtctattaaa agttaaatac ttgtttgttt agctttcgtt ccttagacac atataatcaa    4140
gattctccaa aaccctaata aatctgttac ttacctcgaa atctaattac ccagactact    4200
aattaggtga aaatgattac cggaaatgac ttcaaatgtg gaataatagt ggttgagcgg    4260
tttttccaag tttgtggttt agtgagttgg tattttagat gttaaacgca ctgacatttt    4320
aggttcgcag cagttgaaag tggtaaaaag ctaagataat taaaatctct gccatggaaa    4380
ggcaacagtc tggggagagg tagatttctt gaattgtttc tttgtttctc accaatgggc    4440
tttgttatca gcattattta tttagccaaa gagttctttg tctctgcaaa tggccccaat    4500
caagttttgt ttgagacaat tagctagtgc cagccaatga gtcctatgca aatgtaggga    4560
taggaatgca atgtgtgcat ttgaaggcac gggttttgt tcttggggaa ggcagattgt     4620
aattgctttc ttcgggtact tttttttttt ttttaagttt agggtggggg tggggaagac    4680
aggtttatct ggtctccttc catccctct agttccagag cagctggggg tggggtgggg     4740
gatgggggtg gggggagtgt ctgcaagtcc tttaaaagcc tctgcctcgc ctagtccgtg    4800 ctcttttttaa gttagtgctg gaacgtggaa gagctgctgc ctccgaagca gtaaaccagc   4860
ccctctgttt gtttgtttgc tttgcccttag ttccactgc tccaaaccca cccaccaagg    4920
actctgaacc tgtccacccc gggcgcatca agatcttcca gctgggtacc cccgatttgg   4980
gccgactttg cacctccaaa caaccttagc atgatgtctt atcttaagca accgccttac    5040
gcagtcaatg ggctgagtct gaccacttcg ggtatggact tgctgcaccc ctccgtgggc    5100
tacccgggta agtgagccct gctgcactcc cgcacccctc ttccccatgc ccaccctccg    5160
gggatgcaac accctgttcc catggaacac ggggttggc agtcacactg tccccaccca    5220
gcttcaggct tggtctcctc taggtttgcc ttctgaggaa gcagtcccag ggcatttact    5280
gaccaagcag agaacagggg ttgggaaaag tgagtaggtg ggtctgcaac cgttacaatc    5340
acatcacttt attcttaatt cgagtaaata aggattggca tcagagtggg atgaggaagg    5400
ttactgtcct tgtcatttgg gcaaaagacc cctacccata tctcaatgac caattcctca    5460
gaagtgtcct cttggagaag ctgagttttc cctccgtaag tccttagcac tctcgggctt    5520
cgcagttgtt ccctccatgc ccaggccttc ccctatgacc tccagagcct gctttaatcc    5580
caagaggcgt gacttcctcc aaatgcgggt gctttccttt ccaatcagat atgtttaaaa    5640
atcctcccag gagtatgaac tatgtcccca ttttaaagat ggaggaacaa aggcccatgg    5700
tgtgctaaaa accatgggaa caggatccag atttccccca tcaattcgag ctgccagtct    5760
gtcctcggag atcctttgac ttcttggaat agccttttg tgttgtggtt tgggggttga     5820
tcttggagaa cttttttgtg tgtctttaa aaaatgtttc atttgttaac tttccaagtg     5880
atgctctgat tggagcaatc tcaacaccaa gaagagtagg gaaagaagca gcgtgtgtcc    5940
tgggtccccg gggagcaagg ctggggagac ggtggggaga gcattggtag gctcccggct    6000
gaagggctgt gaggaacggg ggactgctgc ggggtggagg gcagggcgt cggagaaccc     6060 gcggaaacgc ctatgactga gaaactgctc ccccacccta aagggccctg ggcttcttgt    6120
cccgcagcca ccccccggaa acagcgccgg gagaggacga cgttcactcg ggcgcagcta    6180
gatgtgctgg aagcactgtt tgccaagacc cggtacccag acatcttcat gcgagaggag    6240
gtggcactga aaatcaactt gcccgagtcg agggtgcagg tagggcagat gcaggcagaa    6300
ccatccttcc tgatcatgcc acccttcccg agtatgggac tgtggagagc cccaggtctt    6360
```

```
tcagaggact gaaggaaggc ttgaaattct ccttcactca ctaagggcc aggaaactat    6420
tctccttctg cccttttttg cctgcccgtc accacttaat cccgtaagca agggtcttca    6480
aggcccgggt tgctggtgga gagagaccca tccttgagca ggtttcaaga gtagtcacgt    6540
ggtgttgtaa cccttccctt cctctgtata gaaatcctct cctattctca tggacttgta    6600
cgtgtgaaag cagcttagct cttggacagt ccaagtattt ttacagatga aaaatagag    6660
taaatgactt gctcaaggtc ataactaagt ttggtggcag agtcagggta tagacgcagc    6720
tggtgctttt accaaataaa tcaacacaaa aagaatgtat tttccttgac ttcttaggga    6780
ttgaagagaa ttttctagtt ctgagccatt aacagataa aatatctaca taatgtctct    6840
agtgacaccc ctcttgtttt agttcccta aacttgacct taaactggag agggaaggtc    6900
aactccagct tgccttgtga gtgagccctg tacagaattc tctgcaaagt gtttagcaca    6960
taaaccacat acacacctgg gcctctcctt cggctagaat atgtttatga aagcgacaga    7020
catcagtgtc agctgcaaat tgggaaaggg gcttttcaa agtaggttag aggaagtttt    7080
agcacttgca aggcttgaac caaagtcctc actaggagaa acaaatggc tccaaatggt    7140
tggtggtctt gagcttggcc ttggtggcct cacttttacc acagttacgg caccccatac    7200
gagagctcat tcaaaagttc agctaaggat ttgtcctcca gaaaatgcca gtagttcctc    7260
ttctaagccc cctcgtacac caatcatagc tccttcattg cagaacatga acagggctgg    7320
taaagagaat tgtcaagatt gcagcagggg gttgaagtgg taagtcagta aacacagcac    7380
aggagactga gtctatgtgc tgagtggcac tactctaaca acacagactc gagtcccaga    7440
gactagcagg tctgtgctcc agctcaaagc agagtgcatg taagtcactc cttttaccac    7500
aaagaagctt ttagcaaata gtggctttca gacctctttc ttcaacaaga tcatgtcttc    7560
cccttggagc tttgttctgt gagtctttct aagagagaca gaagggtgat ggaaccaacc    7620
aacctctata ttagcagttg cttcctggaa gatgaactgt aaatgaattt aggctgttcc    7680
tgttagcctg taacaacaga attgctttct ctcacttctc atgtatttcc ctccaaaaga    7740
cagagataca ttctattcct ctgtgagagt gttccaaaat atagctgggt ctatgtgtat    7800
gtgtgtgtta gaggcgaaat aagataggaa agtgatgtgg agagttttta gctatatgat    7860
ttgggggatt atcttaaatg ttattctggg caagaaataa gacagtgtca agtgttttta    7920
gacagagcct ccccaacttt cttacaagtc caggagttta tatgagagta ccacataata    7980
ggtcttcagt ggcaggggaa attgtgtgtt tagctgatct gcccatgtag gatagattta    8040
taatacggga gccattcttg tccttaagga actatcaaaa ccgagttaaa gaattttctt    8100
tcccttccaa ggtatggttt aagaatcgaa gagctaagtg ccgccaacaa cagcaacaac    8160
agcagaatgg aggtcaaaac aaagtgagac ctgccaaaaa gaagacatct ccagctcggg    8220
aagtgagttc agagagtgga acaagtggcc aattcactcc cccctctagc acctcagtcc    8280
cgaccattgc cagcagcagt gctcctgtgt ctatctggag cccagcttcc atctccccac    8340
tgtcagatcc cttgtccacc tcctcttcct gcatgcagag gtcctatccc atgacctata    8400
ctcaggcttc aggttatagt caaggatatg ctggctcaac ttcctacttt gggggcatgg    8460
actgtggatc atatttgacc cctatgcatc accagcttcc cggaccaggg gccacactca    8520
gtcccatggg taccaatgca gtcaccagcc atctcaatca gtccccagct tctctttcca    8580
cccagggata tggagcttca agcttgggtt ttaactcaac cactgattgc ttggattata    8640
aggaccaaac tgcctcctgg aagcttaact tcaatgctga ctgcttggat tataaagatc    8700
agacatcctc gtggaaattc caggttttgt gaagacctgt agaacctctt tttgtgggtg    8760
```

```
atttttaaat atactgggct ggacattcca gttttagcca ggcattggtt aaaagagtta      8820
gatgggatga tgctcagact catctgatca aagttccgag aggcatagaa ggaaaaacga      8880
agggccttag aggggcctac aaaccagcaa catgaaatgg acaaaccaat ctgcttaaga      8940
tcctgtcata gttttagatc attggttatc ctgatttgca aagtgatcaa aagcattcta      9000
gccatgtgca accaaacacc accaaaaata aaatcaaaca aaactaagtt gtgaaggaag      9060
ggagggaagg tcatagcctt cttaagcaga ggtgttccat tgttttagcc aatccttggt      9120
tgaatcttag gaatgaacag tgtctcaagc tcattcacgt ttcatgacca actggtagtt      9180
ggcactgaaa aaacttttca gggctgtgtg aattgtgtga ctgattgtcc tagatgcact      9240
actttattta aaaaataatg ttcataagga gtcaatatgt agtttaagag acaatcagtg      9300
tgtgtcttat aaatggtaca tctgtggttt ttaatctgtg ctagacttca aaactgtgat      9360
ctcctgttat tgtatgcaac cttgaactcc acctctgcag gggttcttct gtgattaaat      9420
aggttataat tataagcaaa attcagagca actgagtact gatctaaaaa gattaccttt      9480
ggctggaggt gagctgcact gaaactttac gacaaaatgt ctctggacaa agagagtcag      9540
agaagagaag caaaaggaca ctaattcatc tgtaatttac tgttggtaag cctagcagta      9600
aagagacatt ggtcaattgc tctgaccctg atgaattatt aaactgagat cattgtcgtt      9660
tatgcttgca gatgttaaat ggaaaagtta tatatgcata aaccttttct tcctggattt      9720
ggcagatatg tataattata ttaaaatggt tctagcacaa                            9760
```

METHODS FOR PURIFYING MIDBRAIN DOPAMINERGIC NEURAL PROGENITOR CELLS

CROSS REFERENCE TO RELATED APPLICATIONS

This application is a 35 U.S.C. §371 National Phase Entry Application of International Application No. PCT/US2012/038513 filed May 18, 2012, which designates the U.S., and which claims benefit under 35 U.S.C. §119(e) of the U.S. Provisional Application No. 61/488,678 filed May 20, 2011, the contents of each of which are incorporated herein by reference in their entireties.

GOVERNMENT SUPPORT

This invention was made with government support under Grant No. NS070577, MH048866, and MH087903 awarded by the National Institute of Neurological Disorders and Stroke and the National Institute of Mental Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 28, 2013, is named 063476-074032_SL.txt and is 28,585 bytes in size.

TECHNOLOGICAL FIELD

The technology described herein relates to the field of neural progenitor cells. Specifically, the technology described herein provides methods and compositions related to purified populations of neural progenitor cells with dopaminergic differentiation potential.

BACKGROUND

The following description is provided to assist the understanding of the reader. None of the information provided or references cited is admitted to be prior art to the present invention.

Since dopamine (DA) was identified as a brain neurotransmitter 50 years ago (Carlsson et al., 1957), numerous scientists demonstrated its critical role in normal as well as in diseased brains. The majority of DA neurons reside in the ventral mesencephanlon, forming midbrain DA (mDA) neurons. They critically control voluntary movement, reward, and mood-related behaviors, and their degeneration/dysfunction is associated with major brain disorders such as Parkinson's disease (PD) and schizophrenia. Thus, purification and characterization of expandable mDA progenitor cells is crucial for the design of effective therapeutic approaches for these diseases as well as to provide an in-depth understanding of mDA neuron development and biology. Recent developments in pluripotent stem cell technology such as embryonic stem cells (ESC) and induced pluripotent stem cells (iPSC) promise an unlimited quantity of differentiated cells for such purposes, only if there is a reliable method by which specific progenies can be isolated/purified from heterogeneous population of differentiated cells.

Despite many studies from different labs, no single marker that can purify mDA neural progenitor cells (NP cells) has yet been found. However, based on the knowledge gained from developmental studies of mDA neurons in this and other laboratories, mDA NPs can be identified and purified. Dysfunction of mDA neurons has been implicated in various brain diseases such as neurodegenerative and psychiatric disorders. In particular, the selective degeneration of mDA neurons causes PD, one of the most frequent neurodegenerative disorders. PD is often diagnosed when more than 70-80% of DA nerve terminals in the striatum have been degenerated (Agid, 1991). Thus, the need for reconstructive therapies to treat PD led to the development of fetal cell transplantation therapies (Lindvall and Bjorklund, 2004).

Whereas fetal DA cell transplantation showed the proof-of-principle of cell-based therapy of PD, its use is limited by the lack of standardized fetal cells and ethical controversies. Alternatively, mDA neurons can be derived from ESCs as an unlimited cell source (Bjorklund et al., 2002; Chung et al., 2002; Kawasaki et al., 2000; Kim et al., 2002; Perrier et al., 2004; Roy et al., 2006), but ES-derived progenies are heterogeneous, thus rendering control of their function after transplantation difficult, which is one of the major obstacles for clinical application of ESCs. ESC-derived cells often contain more immature cells and even residual pluripotent cells that can form tumors (Chung et al., 2006a; Roy et al., 2006; Schulz et al., 2004; Zeng et al., 2004). In addition, the lack of a standardized cell source and unfavorable cell composition (e.g. too many serotonergic neurons) can result in complications such as graft-induced dyskinesia after transplantation (Lindvall and Kokaia, 2009; Politis et al., 2010).

Thus, purification of desired cell types from differentiated ESC prior to transplantation is critical for the safety and efficient function of the grafts. Furthermore, isolation of functionally verified mDA cells from ESC-derived progenies can provide valuable resources to study the biology of mDA NP cells and mDA neurons, which is crucial to further understanding of the etiology of PD and the design of effective therapeutic approaches. What is more, it will also serve as a bioassay and drug screening tools, thus facilitating a pharmacological intervention for the treatment of PD. Recently developed iPSC technology (Takahashi and Yamanaka, 2006) offers the possibility to generate disease- or patient-specific stem cells, which could provide a way to model a disease in a dish or to avoid immune rejection caused by non-autologous cell therapy. However, to realize the full translational potential of these pluripotent cells (e.g., ESCs and iPSCs), it is critical to develop reliable and optimal methods to identify and purify specific cell populations. Furthermore, given the extreme vulnerability and poor survival of terminally differentiated neurons in vitro and in vivo, it is important to identify and isolate specific neural progenitor cells that are expandable and able to better survive.

SUMMARY

The present methods and composition are based on the discovery, isolation, and characterization of specific neural progenitor cell populations that are derived in vitro from pluripotent cells, including human embryonic stem cells (hESCs), and methods for making and use the same. Specifically identified are populations of midbrain dopaminergic neural progenitor cells that express Corin and Frizzled-5 (Fzd5).

In one aspect, the present technology includes a method for purifying midbrain dopaminergic neural progenitor cells including (a) providing a neural progenitor cell population that includes midbrain dopaminergic (mDA) neural progenitor cells in cell culture medium, and (b) isolating neural progenitor cells that express Corin and one or more additional markers selected from the group consisting of Otx2 and Frizzled-5 (Fzd5) from the cell population of step (a). The neural progenitor cells that express Corin and the one or more additional cell markers are identified as mDA neural progenitor cells.

In some embodiments, isolating mDA neural progenitor cells comprises flow cytometry. In some embodiments, the neural progenitor cell population is produced by a method including (i) providing a cell population comprising pluripotent cells in cell culture medium; and (ii) differentiating at least some of the pluripotent cells into neural progenitor cells.

In some embodiments, the neural progenitor cell population is produced by a method including (i) culturing a population of pluripotent cells in the presence of leukocyte inhibitory factor (LIF) and serum, (ii) culturing the cells produced in step (i) in the absence of LIF, (iii) culturing the cells produced in step (ii) in the absence of serum, and in the presence of insulin, transferrin, selenium, and fibronectin; and (iv) isolating nestin-positive cells produced in step (iii) and culturing the nestin-positive cells in the presence of laminin. The cells of step (iv) are cultured in the presence of one or more growth factors selected from fibroblast growth factor 8 (FGF8) and basic fibroblast growth factor (bFGF), to produce a population of neural progenitor cells.

In some embodiments, the neural progenitor cell population is produced by a method including (i) culturing a population of pluripotent cells in the presence of one or more growth factors selected from basic fibroblast growth factor (bFGF) and fibroblast growth factor 8 (FGF8), (ii) culturing the cells produced in step (i) in the presence of sonic hedgehog (SHH) protein and in the absence of serum, and (iii) culturing the cells obtained in step (ii) in the presence of bFGF to produce a population of neural progenitor cells.

In some embodiments, the neural progenitor cell population is produced by a method including (i) culturing a population of pluripotent cells in the presence of one or more growth factors selected from fibroblast growth factor 8 (FGF8), epidermal growth factor (EGF), and basic fibroblast growth factor (bFGF), (ii) culturing the cells produced in step (i) in the absence of bFGF, and (iii) culturing the cells produced in step (ii) in the presence of bFGF to produce a population of neural progenitor cells.

In some embodiments, the neural progenitor cell population is a substantially homogenous cell population of Nestin-positive cells. In some embodiments, the mDA neural progenitor cells are further differentiated into a cell population of neuronal differentiated (ND) cells by culturing the mDA neural progenitor cells in the absence of growth factors selected from the group consisting of fibroblast growth factor 8 (FGF8) and basic fibroblast growth factor (bFGF). In some embodiments, epidermal growth factor (EGF) is removed from the culture medium to produce a population of ND cells.

In some embodiments, the isolated mDA neural progenitor cells further express one or more of the markers selected from the group consisting of: FoxA2, Otx2, Lmx1a, Lmx1b, Glast, Vimentin, Nestin, GFAP, and beta-tubulin. In some embodiments, the isolated mDA neural progenitor cells further express Otx2.

In some embodiments of the methods, the ND cells express (a) one or more markers selected from the group consisting of tyrosine hydroxylase, dopamine active transporter, and dopamine decarboxylase, and (b) one or more markers selected from the group consisting of Pitx3, Lmx1a, Lmx1b, FoxA2, En-1, and Nurr1. In some embodiments of the methods, the neural progenitor cells are differentiated by inducing expression of proteins Lmx1a, FoxA2, and Otx2. In some embodiments of the methods, the neural progenitor cells are differentiated by inducing expression of proteins Corin and Fzd5

In some embodiments, the neural progenitor cells isolated in step (b) express one or more of Otx2 protein and Fzd5 protein, wherein the protein is associated with a tag that allows the detection of protein expression. In some embodiments, the tag is fluorescent. In some embodiments, the tag is green fluorescent protein (GFP).

Another aspect of the present technology provides a cell population that includes a substantially homogenous population of midbrain dopaminergic (mDA) neural progenitor cells, wherein the mDA neural progenitor cells express Corin and one or more additional markers selected from the group consisting of Otx2 and Frizzled-5 (Fzd5). In some embodiments, the mDA neural progenitor cells further express one or more of the markers selected from the group consisting of: FoxA2, Otx2, Lmx1a, Lmx1b, Glast, Vimentin, Nestin, GFAP, and beta-tubulin. In some embodiments, the mDA neural progenitor cells further express Otx2. In some embodiments, the mDA neural progenitor cells have a radial glia-like morphology. In some embodiments, the percentage of cells in the cell population that express Corin and one or more additional markers selected from the group consisting of Otx2 and Fzd5 is about 50%; is about 60%; is about 70%, is about 80%, is about 90%.

Another aspect of the present technology provides a therapeutic composition including a cell population that includes a substantially homogenous population of midbrain dopaminergic (mDA) neural progenitor cells, wherein the mDA neural progenitor cells express Corin and one or more additional markers selected from the group consisting of Otx2 and Frizzled-5 (Fzd5). In some embodiments, the cell population of the therapeutic composition is suspended in a physiologically compatible solution. In some embodiments, the cell population of the therapeutic composition is encapsulated.

Another aspect of the present technology provides a method for treating a neurodegenerative disease in a patient, including administering to the brain of the patient a substantially homogenous population of cells, wherein the cells of the population are characterized as expressing the markers Corin and one or more additional markers selected from the group consisting of Otx2 and Frizzled-5 (Fzd5). In some embodiments, the population of cells comprises midbrain dopaminergic (mDA) neural progenitor cells. In some embodiments, the cells further express one or more of the markers selected from the group consisting of: FoxA2, Otx2, Lmx1a, Lmx1b, Glast, Vimentin, Nestin, GFAP, and beta-tubulin. In some embodiments, the cells further express Otx2. In some embodiments, the morphology of the cells is a radial glia-like morphology.

In some embodiments, the cells are administered to the caudate of the patient. In some embodiments, the cells are administered to the substantia nigra of the patient. In some embodiments, the cells are administered to the A9 region of the substantia nigra of the patient.

In some embodiments, a neural progenitor cell population is produced by a method including (i) culturing a population of pluripotent cells in the presence of TGF-β inhibitor and Noggin protein; (ii) culturing the cells produced in step (i) in the absence of TGF-β inhibitor; (iii) culturing the cells produced in step (ii) in the presence of basic fibroblast growth factor (bFGF) to produce a population of neural progenitor cells.

In another aspect, the technology described herein provides an antibody that specifically recognizes an extracellular epitope of the Frizzled-5 receptor and binds to neural progenitor cells. In certain embodiments, the antibody does not bind to embryonic stem cells. In some embodiments, the antibody is derived from a mouse or a rabbit. In some embodiments, the antibody is suitable for use in flow cytometry.

The term "Frizzled-5" or "Fzd5" refers to a 7 transmembrane domain protein that is believed to be the receptor for the Wnt5A ligand and is expressed in mesencephalic rostral floor plate cells (Summerhurst et al., 2008). The genomic nucleotide sequence of Fzd5 is listed in SEQ ID NO: 1 (FIG. 5).

The term "Corin" refers to a cell surface protease that is a marker for rostral and caudal mesencephalic floor plate cells during neuronal development (Ono et al., 2007). The human mRNA nucleotide sequence of Corin is listed in SEQ ID NO: 2 (FIG. 6).

The term "Otx2" (orthodenticle homeobox 2) refers to a transcription factor that is specifically expressed in the neural progenitor domain of forebrain and midbrain. Ectopic expression of Otx2 in caudal floor plate cells can induce a mesencephalic floor plate phenotype (Ono et al., 2007). The genomic nucleotide sequence of human Otx2 is listed in SEQ ID NO: 3 (FIG. 7).

The term "embryonic stem cells" (ESC) refers to cells derived from the inner cell mass of blastocysts, blastomeres, or morulae that have been serially passaged as cell lines while maintaining an undifferentiated state (e.g. express TERT, OCT4, and/or TRA antigens). The ES cells may be derived from fertilization of an egg cell with sperm or DNA, nuclear transfer, parthenogenesis, or by means to generate hES cells with hemizygosity or homozygosity in the MHC region.

As used herein, "pluripotent cells" refers to cells capable of differentiating into cell types from any of the three germ lines and also capable of in vitro self-replication, under appropriate conditions, for virtually an indefinite period of time, wherein the daughter cells retain the undifferentiated (pluripotent) characteristics of the parent cells. Pluripotent cells include ESCs but are not necessarily totipotent like ESCs. Other examples of pluripotent cells include induced pluripotent cells (see, for example, Takahashi et al., Cell, 126: 663-676, 2006; Cell, 131: 861-872, 2007; and Nakagawa et al., Nat. Biotechnol. 26: 101-106, 2008), pluripotent cells derived by nuclear transfer, and pluripotent cells isolated from umbilical cord blood or adult blood.

The term "induced pluripotent stem cell" (iPS cell) refers to pluripotent cells derived from mesenchymal cells (e.g., fibroblasts and liver cells) through the overexpression of one or more transcription factors. In one specific embodiment, iPS cells are derived from fibroblasts by the overexpression of Oct4, Sox2, c-Myc and Klf4 according to the methods described in Takahashi et al. (Cell, 126: 663-676, 2006), for example. Other methods for producing iPS cells are described, for example, in Takahashi et al. (Cell, 131: 861-872, 2007) and Nakagawa et al. (Nat. Biotechnol. 26: 101-106, 2008). The iPS cells of the technology described herein are also capable of cell division.

As used herein, "neural progenitor cells" refers to a subset of pluripotent cells which have partially differentiated along a neural progenitor cell pathway and express some neural markers including, for example, nestin. Neural progenitor cells may differentiate into neurons or glial cells (e.g., astrocytes and oligodendrocytes). Thus, "neural progenitor cells derived from iPS cells" refers to cells that are pluripotent but have partially differentiated along a neural progenitor cell pathway (i.e., express some neural progenitor cell markers), and themselves are the result of in vitro or in vivo differentiation iPS cells.

As used herein, "midbrain dopaminergic neural progenitor cells" or "mDA neural progenitor cells" refers to a subpopulation of neural progenitor cells that when isolated, can form a substantially homogenous cell population of midbrain dopaminergic neurons.

As used herein "a substantially homogenous cell population" refers to a population or sample of cells which contain a majority (i.e., at least 50%) of cells having the trait(s) of interest. In preferred embodiments, substantially homogenous populations contain at least 60%, at least 70%, at least 80%, at least 90% or more of the cells having the trait(s) of interest.

As used herein "physiologically compatible solution" refers to a solution that at least partially mimics the liquid environment that would normally surround a given cell type when it is in the body. Such a solution can prevent cells from being damaged when removed from the body or from a culture environment. A physiologically compatible solution can mimic salt composition and concentration as well as proteins such as growth factors. Physiologically compatible solutions include, for example, cell culture medium (e.g., Eagle's minimal essential media), phosphate buffered saline, Hanks balanced salt solution, or artificial cerebrospinal fluid (aCSF).

As used herein, proteins "associated with a tag" means that the protein is covalently attached to the tag, for example, green fluorescent protein (GFP) is fused to the protein, or that the protein is covalently attached to the protein. The association can also be non-covalent, as seen for example in receptor/ligand interactions.

By a "vector" is meant a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

Non-viral vector may include plasmid that comprises a heterologous polynucleotide capable of being delivered to a target cell, either in vitro, in vivo or ex-vivo. The heterologous polynucleotide can comprise a sequence of interest and can be operably linked to one or more regulatory element and may control the transcription of the nucleic acid sequence of interest. As used herein, a vector need not be capable of replication in the ultimate target cell or subject. The term vector may include expression vector and cloning vector.

Suitable expression vectors are well-known in the art, and include vectors capable of expressing a polynucleotide operatively linked to a regulatory element, such as a promoter region and/or an enhancer that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

BRIEF DESCRIPTION OF THE DRAWINGS

FIG. 2B also shows photomicrographs of Corin$^+$Fzd$^+$ neural progenitor cells stained with Otx2, FoxA2, Lmx1b, Corin, GLAST, Nestin, β-tubulin, tyrosine hydroxylase, and Pitx3.

FIG. 5 is the human genomic sequence of Frizzled-5 (SEQ ID NO: 1). Sequence is at GenBank Acc. No. NC_000002.11 from nt 208627310 to nt 208634143.

FIG. 6 is the human mRNA sequence of Corin (SEQ ID NO: 2). Sequence is at GenBank Acc. No. NM_006587.2.

FIG. 7 is the human genomic sequence of OTX2 (SEQ ID NO: 3). Sequence is at GenBank Acc. No. NG_008204.1.

FIG. 8A depicts the head down time for the pole test. FIG. 8B depicts the total time for the pole test. FIG. 8C depicts the times for the beam test.

DETAILED DESCRIPTION

Figure 1A:
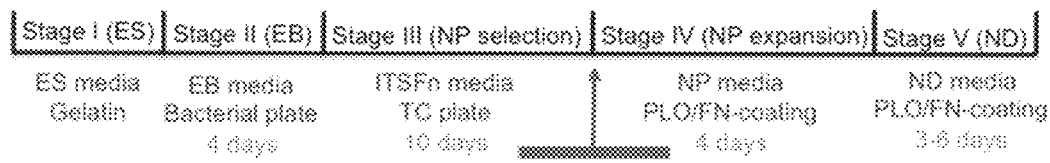
FIG. 1A shows a schematic of the culture stages for differentiating mouse ES cells into ND cells, as described in Example 1.

The technology described herein provides novel populations of midbrain dopaminergic neural progenitor cells and methods for producing the same from human embryonic stem cells, induced pluripotent stem cells, or other types of pluripotent cells. The inventive cell populations have a unique cell surface marker profile that corresponds to a defined stage of cellular differentiation.

In Vitro Differentiation of Human Embryonic Stem Cells

Mature mDA neurons have been purified from genetically marked neurons (Hedlund et al., 2008), but they could not survive well in transplanted host brains due to their vulnerability. Purified ES-derived NPs have also been purified using the general NP marker Sox1 (Chung et al., 2006a). However, the proportion of mDA cells was low, probably due to the nature of mDA NP as glial like floor plate cells rather than general NPs (Ono et al., 2007). This illustrates the need to purify relevant NP population based on developmental studies.

It was recently reported that mDA NPs can be efficiently enriched using the floor plate cell surface marker, Corin (Chung et al., 2009; Ono et al., 2007), thus opening a new possibility to purify less vulnerable and potentially expandable mDA NPs population. Nevertheless, Corin is not sufficient for purification of mDA NPs, since it is also expressed in caudal floor plate cells as well as heart and skin cells. One approach to purifying mDA NPs is to use the combination of two specific markers, Corin and Otx2. Using this approach, specific and efficient purification of mDA NPs can be achieved, which was not previously possible. Double selection of rostral floor plate cells using Corin and Otx2 efficiently removes dyskinesia-inducing serotonergic neurons (Chung et al., 2011a), which are induced by similar sets of signals as mDA neurons (e.g. SHH and FGF8) in vivo and in vitro (Lee et al., 2000; Ye et al., 1998).

Both EB-based and stromal co-culture ESC differentiation have been fully established. Resulting ESCs have also been extensively studied both in vitro and in vivo after transplantation. When undifferentiated ESCs were grafted into the striatum of 6-OHDA lesioned rats, they differentiated into DA neurons and ameliorated behavioral symptoms (Björklund et al., 2002). In addition, ESCs have been genetically engineered by overexpressing the key transcription factors Nurr1 or Pitx3, which facilitated the differentiation of ESCs to mDA neurons (Chung et al., 2002) or A9-like DA neurons (Chung et al., 2005), respectively. More recently two major pathways of mDA development have been identified, and genetic modification using direct targets of these pathways (FoxA2, Lmx1a and Otx2) has been observed to synergistically induce mDA differentiation of ESCs (Chung et al., 2009). ESC-derived NPs have been systematically characterized and showed that ESC-derived NPs generate DA neurons efficiently after prolonged expansion, whereas embryonic brain (VM)-derived NPs lose the potential to generate DA neurons even after short-term expansion (Chung et al., 2006b). Also after transplantation, these ESC-derived NPs efficiently generated DA grafts, demonstrating that expansion of ESC-derived NPs can serve as a powerful and efficient procedure to prepare an unlimited cell source from ESCs for therapeutic purposes. To reduce/avoid tumor formation after transplantation, ESC-derived NPs have been isolated using sox1GFP knock-in ESCs (Chung et al., 2006a). Purification of NPs by FACS resulted in enrichment of the neural population while eliminating tumor formation in the grafts.

Several lines of human embryonic stem cells (hES) (H1, H9 and HSF-6) can be successfully differentiated into DA neurons using the previously described procedure in Park et al. (2005) with modification. This modified procedure uses an MS5 feeder layer and SHH as an inducing signal. hES-derived NPs can also be successfully frozen and thawed without losing proliferative and differentiation potential, as in the case with mES-derived NPs. The efficiency of generating mDA NPs (Corin$^+$Otx2$^+$), using other published protocols was more extensively compared, in order to optimize mDA NP generation before purification of these cells.

For purification of human mDA NPs, one approach is purification of the NP cells that coexpress Corin and Fzd5. Fzd5 is expressed in forebrain and midbrain in developing embryo, as well as in eye and liver. Fzd5 antibody stains human liver-derived HepG2 cells, and does not stain control ES cells. Fzd5 is a marker that has never been used for cell sorting, but is a good complementary marker, since its expression is limited to forebrain and midbrain in the developing CNS. This approach removes any caudal floor plate phenotype as well as non-neural Corin$^+$ cells such as heart and skin. The Fzd5/Corin marker combination has several advantages. For example, mDA NPs are purified with a high degree of specificity and efficiency; purification of a less vulnerable and expandable mDA NP population is achieved; eliminating the genetic modification step removes the risk of insertional mutagenesis while increasing the efficiency and ease of generating the cells of interest, and these purified mDA NPs represent expandable "rostral floor plate cells", efficiently eliminating serotonergic cells that can cause graft-induced dyskinesia.

To test the anti-corin antibody later used in flow cytometry, retrovirus that expresses human Corin-myc recombinant protein was generated, and cells were infected with this retrovirus. Anti-Corin antibody staining was well overlapping with myc staining, showing specificity of anti-Corin antibody in recognizing human Corin protein. In addition, a minor population of Corin$^+$Fzd5$^+$ cells was detected after in vitro differentiation of hES cells.

Isolating Corin/Fzd5-Expressing Neural Progenitor Cells

Recent studies have shown that floor plate cells are the NPs that generate mDA neurons (Kittappa et al., 2007; Ono et al., 2007). mDA NPs have been enriched by using the floor plate cell surface marker Corin (Chung et al., 2009; Ono et al., 2007). However, Corin is also expressed in the caudal floor plate, heart and skin, raising the need to further purify Corin$^+$ cells using a second independent marker. Recently, it has been shown that forebrain-midbrain transcription factor Otx2 can rostralize caudal floor plate, generating ectopic mDA neurons (Ono et al., 2007). mDA NPs can be isolated by purifying these "rostral floor plate cells" from in vitro differentiated ESCs. Such mDA NPs have been purified using Corin and Otx2 with high efficiency and specificity. However, for clinical application, it is more desirable to use two independent cell surface markers rather than genetic modification.

Frizzled-5 (Fzd5), the receptor for Wnt5a, shows rostral expression pattern in the forebrain and the ventricular zone of the midbrain in the developing CNS (Summerhurst et al., 2008). Moreover, Wnt5a has been shown to be an important regulator of mDA differentiation (Andersson et al., 2008; Parish et al., 2008). The expression of Corin and Fzd5 overlaps only in the mDA domains during embryonic development, together marking the rostral floor plate. Thus, double selection of "rostral floor plate cells" using two independent cell surface markers (e.g. Corin and Fzd5) efficiently purifies mDA NPs from in vitro differentiated mouse and human ESCs and iPSCs.

Purified mDA NPs can be expanded in vitro without losing their proliferative and developmental potentials. These mDA NPs represent ideal and unlimited cell sources for transplantation therapy of PD. The heterogeneous nature of embryonic stem cell-derived progenies resulted in tumor formation or grafts with unwanted cell types after transplantation in some cases (Zeng et al., 2004; Schulz et al., 2004; Roy et al., 2006). Thus, to control the cell types that are transplanted into the brain, it is imperative to purify only desired cell populations that can generate mDA neurons prior to transplantation. Previous studies have purified NPs from in vitro differentiated mouse ES cells, efficiently preventing tumor formation after transplantation. Although sox1$^-$GFP$^+$ grafts contains some TH$^+$ cells, the overall efficiency of TH$^+$ cell generation from sox1$^-$GFP$^+$ cells was not high, demonstrating that these cells are not the right type of NP cells. It is therefore desirable to purify NPs that have the potential to generate mDA neurons.

Purified mDA NPs rather than postmitotic mDA neurons are more desirable, since the former are more amenable to manipulation such as passaging, FACS (fluorescent-activated cell sorting), cryopreservation and transplantation. Furthermore, mDA NPs, unlike mature mDA neurons, could potentially provide an expandable cell source for generating unlimited amounts of mDA neurons.

mDA NPs have been shown to be midbrain floor plate cells (Ono et al., 2007; Kittappa et al., 2007), which can be marked by floor plate marker Corin (Ono et al., 2007). However, corin is also expressed in caudal floor plate as well as heart and skin. Thus, corin antibody alone identifies both mDA NPs and non-mDA NP cells, necessitating another independent marker for purification of mDA NPs. Fzd5 is such a marker that can be used for purification of mDA NPs. Fzd5 is expressed in developing ventricular layer of midbrain as well as forebrain and eye (Summerhurst et al., 2008) and is thought to be the receptor for Wnt5a, which is an important regulator of mDA differentiation (Castelo-Branco et al., 2003). Thus, cells that express both Corin and Fzd5 are mDA NPs from the midbrain floor plate.

Figure 4:
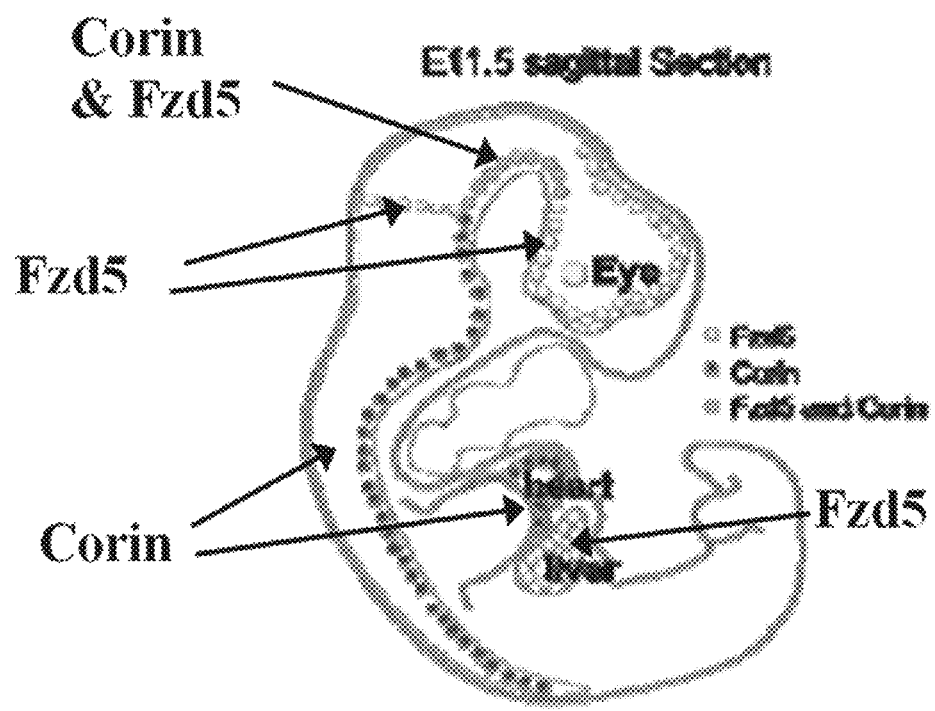
FIG. 4 is a schematic of a sagital section from a 11.5 day mouse embryo that details the expression locations of Corin and Fzd5.

Rostral floor plate cells, representing authentic mDA NPs, can be isolated by double cell surface marker selection in the mouse ESC system. However, a cell surface marker that can be used in combination with the floor plate marker Corin is desirable to purify mDA NPs without genetic modification. Receptor molecules were initially screened, since it is known that several signaling molecules are playing important roles in specification/proliferation of mDA NPs such as SHH, Wnt1, FGF8 and Wnt5a. Among the receptors of these molecules, Fzd5, a receptor for Wnt5a (Andersson et al., 2008; Castelo-Branco et al., 2006; Castelo-Branco et al., 2003; Parish et al., 2008; Sanchez-Pernaute et al., 2008; Schulte et al., 2005) shows a rostral expression pattern in the forebrain and midbrain during embryonic CNS development especially in the midbrain ventricular region as well as in liver (Summerhurst et al., 2008). Its expression pattern overlaps with Corin only in the mDA NP domain during development (FIG. 4). This observation along with the importance of Wnt5a signaling in mDA neurogenesis suggested Fzd5 was a good candidate for double marker selection of mDA NPs.

Cell Transplantation Therapies

Cell transplantation therapies typically involve the intraparenchymal (e.g., intracerebral) grafting of the replacement cell populations into the lesioned region of the nervous system, or at a site adjacent to the site of injury. Most commonly, the therapeutic cells are delivered to a specific site by stereotaxic injection. Conventional techniques for grafting are described, for example, in Bjorklund et al. (Neural Grafting in the Mammalian CNS, eds. Elsevier, pp 169-178, 1985), Leksell et al. (Acta Neurochir., 52:1-7, 1980) and Leksell et al. (J. Neurosurg., 66:626-629, 1987). Identification and localization of the injection target regions will generally be done using a non-invasive brain imaging technique (e.g., MRI) prior to implantation (see, for example, Leksell et al., J. Neurol. Neurosurg. Psychiatry, 48:14-18, 1985).

Briefly, administration of cells into selected regions of a patient's brain may be made by drilling a hole and piercing the dura to permit the needle of a microsyringe to be inserted. Alternatively, the cells can be injected into the brain ventricles or intrathecally into a spinal cord region. The cell preparation as described herein permits grafting of the cells to any predetermined site in the brain or spinal cord. It also is possible to effect multiple grafting concurrently, at several sites, using the same cell suspension, as well as mixtures of cells.

Following in vitro cell culture and isolation as described herein, the cells are prepared for implantation. The cells are suspended in a physiologically compatible carrier, such as cell culture medium (e.g., Eagle's minimal essential media), phosphate buffered saline, Hanks balanced salt solution, or artificial cerebrospinal fluid (aCSF). Cell density is generally about $10^4$ to about $10^7$ cells/µl, and preferably about 25,000 to about 100,000 cells/µl. The volume of cell suspension to be implanted will vary depending on the site of implantation, treatment goal, and cell density in the solution. For example, for treatments in which cells are implanted into the brain parenchyma (e.g., in the treatment of Parkinson's Disease), about 5-60 µl of cell suspension will be administered in each injection. Several injections may be used in each host, particularly if the lesioned brain region is large. Alternatively, administration via intraventricular injection, for example, will accommodate relatively larger volumes and larger cell numbers (see, for example, Madrazo et al., New Engl. J. Med., 316:831-834, 1987; Penn et al., Neurosurgery, 22:999-1004, 1988).

In some embodiments, the cells are encapsulated within permeable membranes prior to implantation. Encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. Several methods of cell encapsulation are well known in the art, such as described in European Patent Publication No. 301, 777, or U.S. Pat. Nos. 4,353,888, 4,744,933, 4,749,620, 4,814,274, 5,084,350, and 5,089,272.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquified using sodium citrate. This creates a single membrane around the cells that is highly permeable to relatively large molecules (MW ~200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off ~40-80 kDa).

Flow Cytometry and Fluorescence-Activated Cell Sorting (FACS)

Flow cytometry is a well-known technique for analyzing and sorting cells (or other small particles) suspended in a fluid stream. This technique allows simultaneous analysis of the physical and/or chemical characteristics of single cells flowing through an optical, electronic, or magnetic detection apparatus. As applied to FACS, the flow cytometer consists of a flow cell which carries the cells in a fluid stream in single file through a light source with excites the fluorescently labeled detection marker (for example, antibody) and measures the fluorescent character of the cell. The fluid stream is then ejected through a nozzle and a charging ring, under pressure, which breaks the fluid into droplets. The flow cell device and fluid stream is calibrated such that there is a relatively large distance between individual cells, resulting in a low probability that any droplet contains more than a single cell. The charging ring charges the droplets based on the fluorescence characteristic of the cell which is contained therein. The charged droplets are then deflected by an electrostatically-charged deflection system which diverts the droplets into various containers based upon their charge (related to the fluorescence intensity of the cell).

Flow cytometry is a particularly useful technique for sorting and characterizing cells having a basic ovoid morphology, with blood cells being the prototypical candidates. Neuronal cells begin to adopt a stellate or dendritic morphology at early stages of differentiation. Detachment of neuronal cells from the solid culture substrate, followed by pruning of the dendritic processes during flow cytometry places a great deal of stress on the cells, making them less reliable in later scientific procedures. As described herein, the basic flow cytometry methodology may be modified to specifically accommodate neuronal cell types in a manner that reduces the stresses placed on the cells, rendering them more amenable for later culture and clinical use.

Two important parameters that may be varied during in the flow cytometry process are the nozzle diameter and the fluid ejection pressure. The stress placed on the neuronal cells may be reduced by increasing nozzle diameter and/or reducing the ejection pressure. These parameters must be optimized for each particular stellate (e.g., neuronal) cell type used in order that the accuracy of the cell sorting method is maintained. For example, an unduly large reduction in fluid/ejection pressure may result in a plurality of cells being trapped in each ejected fluid droplet. This will result in a systematic over-estimation of the labeled cellular marker. If the pressure is sufficiently low, it will also improperly result in a bimodal (or higher order) sorting distribution, wherein the particles tend to sort on the number of cells captured in each particle rather than the signal obtained from each cell (i.e., two cells will have about twice the signal intensity of one cell). Likewise, the nozzle diameter suitable for use with each cell type and at each fluid pressure must also be optimized. Large nozzle diameters are beneficial for large and stellate cells like neurons and neuronal stem cells. However, large nozzle diameters, combined with low fluid pressures result droplets that are unduly large or, in extreme cases, not formed. Large droplets therefore also increase the likelihood of capturing more than one cell in each fluid droplet.

Gene Delivery and Modification of ES Cells

Nucleic acid sequences encoding a gene or gene fragment, such as Corin, Fzd5 or Otx2, can be combined with nucleic acid sequence for a tag to form a tagged fusion protein. Non limiting examples of nucleic acid sequence includes His-tag (a stretch of poly histidines), FLAG-tag, and Green Fluorescent Protein (GFP). His-tag and FLAG-tag can be used to in many different methods, such as purification of protein or detection of protein while it is inside a cell. The tags can also serve as an important site for antibody recognition.

Embryonic stem cells that express a tagged protein, such as Otx2GFP, can be created using vectors, either alone or in combination with "knock-in" homologous recombination techniques. Vectors can also be used with zinc finger nuclease technology to remove a gene or gene fragment and then insert another gene or gene fragment in its place. Zinc finger nuclease technology is described in Hockemeyer et al. (2009). Briefly, a zinc finger domain protein specific for a given sequence is fused with a nuclease, such that when the zinc finger nuclease is expressed in a cells, the zinc finger nuclease removes a specific gene or nucleic acid region from the cell's nucleic acid.

A variety of viral vectors can be used to transfect cells with tagged proteins. Adenoviruses, adeno-associated virus, retroviruses (including lentivirus), and herepmay all be used as vectors to stably express a tagged protein in a cell. Herpes simplex virus (HSV) replicates in epithelial cells, but is able to stay in a latent state in non-dividing cells such as the midbrain dopaminergic neurons. The gene of interest may be inserted into the LAT region of HSV, which is expressed during latency. Other viruses that have been shown to be useful in exogenous gene expression include parainfluenza viruses, poxviruses, and alphaviruses, including Semliki forest virus, Sinbis virus, and Venezuelan equine encephalitis virus (Kennedy, Brain. 120: 1245-1259, 1997).

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle. See Wolff, et al., Human Mol. Genet., 1:363-369, 1992; Wolff, et al., Science, 247, 1465-1468, 1990. DNA-mediated gene transfer has also been characterized in liver, heart, lung, brain and endothelial cells. See Zhu, et al., Science, 261: 209-211, 1993; Nabel, et al., Science, 244:1342-1344, 1989. DNA for gene transfer also may be used in association with various cationic lipids, polycations and other conjugating substances. See Przybylska et al., J. Gene Med., 6: 85-92, 2004; Svahn, et al., J. Gene Med., 6: S36-S44, 2004.

Once appropriate expression non-viral vectors containing a gene, fragment, fusion, or mutant are constructed, they can be introduced into an appropriate host cell by transformation techniques, such as, but not limited to, calcium phosphate transfection, DEAE-dextran transfection, electroporation, microinjection, protoplast fusion, or liposome-mediated transfection. In vitro expression of a protein, fusion, polypeptide fragment, or mutant encoded by cloned DNA may also be used. Those skilled in the art of molecular biology will understand that a wide variety of expression systems and purification systems may be used to produce recombinant proteins and fragments thereof.

Methods of gene therapy using cationic liposomes are also well known in the art. Exemplary cationic liposomes for use in the methods and compositions described herein are DOTMA, DOPE, DOSPA, DOTAP, DC-Chol, Lipid GL-67™, and EDMPC. These liposomes may be used in vivo or ex vivo to encapsulate a vector for delivery into target cells (e.g., pluripotent stem cells).

The methods and compositions described herein will now be described in greater detail by reference to the following non-limiting examples.

Some embodiments of the technology described herein can be defined as any of the following numbered paragraphs.

1. A method for purifying midbrain dopaminergic neural progenitor cells comprising:
   (a) providing a neural progenitor cell population comprising midbrain dopaminergic (mDA) neural progenitor cells in cell culture medium;
   (b) isolating neural progenitor cells that express Corin and one or more additional markers selected from the group consisting of orthodenticle homeobox 2 (Otx2) and Frizzled-5 (Fzd5) from the cell population of step (a), wherein the neural progenitor cells that express Corin and the one or more additional cell markers are identified as mDA neural progenitor cells.

2. The method of paragraph 1, wherein isolating mDA neural progenitor cells comprises flow cytometry.

3. The method of any of paragraphs 1-2, wherein the neural progenitor cell population is produced by a method comprising:
   (i) providing a cell population comprising pluripotent cells in cell culture medium; and
   (ii) differentiating at least some of the pluripotent cells into neural progenitor cells.

4. The method of any of paragraphs 1-3, wherein the neural progenitor cell population is produced by a method comprising:
   (i) culturing a population of pluripotent cells in the presence of leukocyte inhibitory factor (LIF) and serum;
   (ii) culturing the cells produced in step (i) in the absence of LIF;
   (iii) culturing the cells produced in step (ii) in the absence of serum, and in the presence of insulin, transferin, selenium, and fibronectin; and
   (iv) isolating nestin-positive cells produced in step (iii) and culturing the nestin-positive cells in the presence of laminin and one or more growth factors selected from fibroblast growth factor 8 (FGF8) and basic fibroblast growth factor (bFGF), to produce a population of neural progenitor cells.

5. The method of any of paragraphs 1-4, wherein the neural progenitor cell population is produced by a method comprising:
   (i) culturing a population of pluripotent cells in the presence of one or more growth factors selected from basic fibroblast growth factor (bFGF) and fibroblast growth factor 8 (FGF8);
   (ii) culturing the cells produced in step (i) in the presence of sonic hedgehog (SHH) protein and in the absence of serum; and
   (iii) culturing the cells obtained in step (ii) in the presence of bFGF to produce a population of neural progenitor cells.

6. The method of any of paragraphs 1-5, wherein the neural progenitor cell population is produced by a method comprising:
   (i) culturing a population of pluripotent cells in the presence of one or more growth factors selected from fibroblast growth factor 8 (FGF8), epidermal growth factor (EGF), and basic fibroblast growth factor (bFGF);
   (ii) culturing the cells produced in step (i) in the absence of bFGF; and
   (iii) culturing the cells produced in step (ii) in the presence of bFGF to produce a population of neural progenitor cells.

7. The method of any of paragraphs 1-6, wherein the neural progenitor cell population is a substantially homogenous cell population of Nestin-positive cells.

8. The method of any of paragraphs 1-8, wherein the mDA neural progenitor cells are further differentiated into a cell population of neuronal differentiated (ND) cells by culturing the mDA neural progenitor cells in the absence of growth factors selected from the group consisting of fibroblast growth factor 8 (FGF8) and basic fibroblast growth factor (bFGF).

9. The method of paragraph 8, further comprising removing epidermal growth factor (EGF) from the culture medium to produce a population of ND cells.

10. The method of any of paragraphs 1-9, wherein the mDA neural progenitor cells produced in step (b) further express one or more of the markers selected from the group consisting of: forkhead box A2 (FoxA2); orthodenticle homeobox 2 (Otx2); LIM homeobox transcription factor 1, alpha (Lmx1a); LIM homeobox transcription factor 1, beta (Lmx1b); Glast; Vimentin; Nestin; glial fibrillary acidic protein (GFAP); and beta-tubulin.

11. The method of any of paragraphs 1-9, wherein the mDA neural progenitor cells produced in step (b) further express orthodenticle homeobox 2 (Otx2).

12. The method of paragraph 8, wherein the ND cells express:
(a) one or more markers selected from the group consisting of tyrosine hydroxylase, dopamine active transporter, and dopamine decarboxylase; and
(b) one or more markers selected from the group consisting of paired-like homeodomain 3 (Pitx3); LIM homeobox transcription factor 1, alpha (Lmx1a); LIM homeobox transcription factor 1, beta (Lmx1b); forkhead box A2 (FoxA2); engrailed homeobox 1 (En-1); and nuclear receptor subfamily 4, group A, member 2 (Nurr1).

13. The method of any of paragraphs 1-12, further comprising differentiating the neural progenitor cells by inducing expression of proteins LIM homeobox transcription factor 1, alpha (Lmx1a); forkhead box A2 (FoxA2); and orthodenticle homeobox 2 (Otx2).

14. The method of any of paragraphs 1-13, further comprising differentiating the neural progenitor cells by inducing expression of proteins Corin and Frizzled-5 (Fzd5).

15. A cell population comprising:
a substantially homogenous population of midbrain dopaminergic (mDA) neural progenitor cells, wherein the mDA neural progenitor cells express Corin and one or more additional markers selected from the group consisting of orthodenticle homeobox 2 (Otx2) and Frizzled-5 (Fzd5).

16. The cell population of paragraph 15, wherein the mDA neural progenitor cells further expresses one or more of the markers selected from the group consisting of: forkhead box A2 (FoxA2); orthodenticle homeobox 2 (Otx2); LIM homeobox transcription factor 1, alpha (Lmx1a); LIM homeobox transcription factor 1, beta (Lmx1b); Glast; Vimentin; Nestin; glial fibrillary acidic protein (GFAP); and beta-tubulin.

17. The cell population of paragraph 15, wherein the mDA neural progenitor cells further express orthodenticle homeobox 2 (Otx2).

18. The cell population of any of paragraphs 15-17, wherein the mDA neural progenitor cells have a radial glia-like morphology.

19. A therapeutic composition comprising a cell population of any of paragraphs 15-18.

20. The therapeutic composition of paragraph 19, wherein the cell population is suspended in a physiologically compatible solution.

21. The therapeutic composition of paragraph 20, wherein the cell population is encapsulated.

22. The cell population of any of paragraphs 15-18, wherein at least about 50% of the cells express Corin and one or more additional markers selected from the group consisting of orthodenticle homeobox 2 (Otx2) and Frizzled-5 (Fzd5).

23. The cell population of any of paragraphs 15-18, wherein at least about 90% of the cells express Corin and one or more additional markers selected from the group consisting of orthodenticle homeobox 2 (Otx2) and Frizzled-5 (Fzd5).

24. A method for treating a neurodegenerative disease in a patient, comprising administering to the brain of the patient a substantially homogenous population of cells, wherein the cells of the population are characterized as expressing the markers Corin and one or more additional markers selected from the group consisting of orthodenticle homeobox 2 (Otx2) and Frizzled-5 (Fzd5).

25. The method of paragraph 24, wherein the population of cells comprises midbrain dopaminergic (mDA) neural progenitor cells.

26. The method of any of paragraphs 24-25, wherein the cells further express one or more of the markers selected from the group consisting of: forkhead box A2 (FoxA2); orthodenticle homeobox 2 (Otx2); LIM homeobox transcription factor 1, alpha (Lmx1a); LIM homeobox transcription factor 1, beta (Lmx1b); Glast; Vimentin; Nestin; glial fibrillary acidic protein (GFAP); and beta-tubulin.

27. The method of any of paragraphs 24-25, wherein the cells further express orthodenticle homeobox 2 (Otx2).

28. The method of any of paragraphs 24-27, wherein the morphology of the cells is a radial glia-like morphology.

29. The method of any of paragraphs 24-28, wherein the cells are administered to the caudate of the patient.

30. The method of any of paragraphs 24-29, wherein the cells are administered to the substantia nigra of the patient.

31. The method of paragraph 30, wherein the cells are administered to the A9 region of the substantia nigra of the patient.

32. The method of any of paragraphs 1-14, wherein the neural progenitor cells isolated in step (b) express one or more of orthodenticle homeobox 2 (Otx2) protein and Frizzled-5 (Fzd5) protein, wherein the protein is associated with a tag that allows the detection of protein expression.

33. The method of paragraph 32, wherein the tag is detected with fluorescence.

34. The method of paragraph 32, wherein the tag is green fluorescent protein (GFP).

Example 1—Purification, Differentiation, and Expansion of mDA NPs Using Corin and OTX2

Purification of mDA NPs Using Corin and OTX2

A purification scheme for mDA NP cells has been previously devised using co-expression of Corin and Otx2. For Otx2-based purification, Otx2GFP knock-in ESCs were used, where GFP is knocked in in-frame with the Otx2 ORF. The NP cells from the resulting knock-in mice were purified using the technique of Chung et al, (2006a) as follows. Briefly, at stage 1, undifferentiated ES cells were cultured on gelatin-coated dishes in Dulbecco's modified minimal essential medium (DMEM; Life Technologies, Rockville, Md., USA) supplemented with 2 mM L-glutamine (Life Technologies), 0.001% β-mercaptoethanol (Life Technologies), 1× non-essential amino acids (Life Technologies), 10% donor horse serum (Sigma, St. Louis, Mo., USA) and 2000 U/mL human recombinant leukemia inhibitory factor (LIF; R & D Systems, Minneapolis, Minn., USA). At stage 2, ES cells were differentiated into embryoid bodies (EBs) on non-adherent bacterial dishes (Fisher Scientific, Pittsburgh, Pa., USA) for 4 days in the above medium without LIF and exchanging horse serum with 10% fetal bovine serum (Hyclone, Logan, Utah, USA). At stage 3, EBs were then plated onto an adhesive tissue culture surface (Fisher Scientific). After 24 hours in culture, selection of neural progenitor cells was initiated in serum-free insulin, transferin, selenium and fibronectin (ITSFn) media (Okabe et al. 1996). At stage 4, after 10 days of selection, cells were trypsinized and nestin$^+$ neural progenitor cells were plated onto poly L-ornithine- (PLO; 15 µg/mL; Sigma) and fibronectin (FN; 1 µg/mL; Sigma)-coated plates in NP medium [NP medium; N2 medium (Johe et al. 1996) supplemented with 1 µg/mL laminin (Sigma) and 10 ng/mL basic fibroblast growth factor (bFGF) (R & D Systems)]. After 2 days' expansion of nestin$^+$ neural progenitor cells, the cells were trypsinized and subjected to FACS. Subsequently, 1.5×10$^6$ sorted cells/cm$^2$ were plated onto PLO/FN-coated 6 wells, expanded in the presence of 500 ng/mL N-terminal fragment of sonic hedgehog (R & D Systems) and 100 ng/mL fibroblast growth factor-8 (FGF-8) (R & D Systems) for 4 days. At stage 5, cells were either harvested for transplantation or induced to differentiate by removal of bFGF in the presence of 200 µM ascorbic acid (Sigma) (Lee et al. 2000; Chung et al. 2002). The stages of culture are represented in the schematic of FIG. 1A.

After culturing and differentiating NP cells from Otx2GFP$^+$ knock-in mice the presence of Corin$^+$Otx2GFP$^+$ NP cells was observed. These Corin$^+$Otx2GFP$^+$ cells were purified from differentiated ESCs after anti-Corin staining using FACS. Immunocytochemistry analysis showed that Corin$^+$Otx2GFP$^+$ cells were efficiently purified (88.7±9.2% Otx2$^+$/Hoechst$^+$ cells and 87.5±7.2% Corin$^+$/Hoechst$^+$ cells) and they consist of immature precursors largely negative for mature markers, GFAP or β-tubulin, but positive for the NP marker Nestin and the radial glia marker GLAST (data not shown). In addition, they also express two independent mDA NP markers, FoxA2 and Lmx1b (data not shown), again confirming their identity as mDA NPs. In addition, the double marker purification strategy efficiently removed unwanted pluripotent cells which can cause teratomas following transplantation, shown by absence of SSEA1 in the purified Otx2GFP$^+$Corin$^+$ cell population (14.7±2.1% SSEA1$^+$ in unsorted vs. <0.1% (detection limit) of SSEA1$^+$ in Otx2GFP$^+$Corin$^+$ cells by FACS analysis).

Differentiation of mDA NPs Using Corin and Otx2

Corin$^+$OtxGFP$^+$ cells were further analyzed after 7 days of neuronal differentiation. TH$^+$ neurons were significantly enriched, whereas GABA$^+$ neurons were significantly decreased after sorting (data not shown; 5.6±1.9% vs 80.2±4.9% TH/β-tubulin and 36.9±4.9% vs 8.7±0.8% GABA/β-tubulin for unsorted vs sorted cells). There were 83±2.7% β-tubulin$^+$ cells in sorted cells, with 7.3±2.0% GFAP$^+$ cells and 5.3±0.6 Nestin$^+$ cells. TH$^+$ neurons derived from Corin$^+$Otx2GFP$^+$ cells were further characterized by co-staining with other mDA markers, and it was observed that these TH$^+$ cells also express Pitx3, Lmx1b and Nurr1 (data not shown; 83±6.5% Pitx3/TH cells, 88.9±1.5% Lmx1b/TH cells), confirming that two markers sorting can prospectively identify mDA NPs. They also express the functional DA markers, DAT and DDC, and there are both A9 and A10 DA neurons, as shown by calbindin and Girk2 co-labeling (data not shown).

Expansion of mDA NPs Using Corin and Otx2

The proliferative potential of sorted Corin$^+$Otx2GFP$^+$ cells was tested. These cells were expanded in the presence of bFGF, and passaged weekly. There was about a 1.000-fold increase in a 4-week period. Immunocytochemistry analysis showed that after extensive expansion, the majority of the cells were still Otx2$^+$FoxA2$^+$ as well as Nestin$^+$GLAST$^+$ (data not shown). 4 weeks-expanded cells were further differentiated by withdrawal of bFGF, and showed that they can efficiently generate mDA neurons, as shown by coexpression of TH and Pitx3 (data not shown).

Grafting of Corin$^+$Otx2GFP$^+$ cells

Figure 1B:
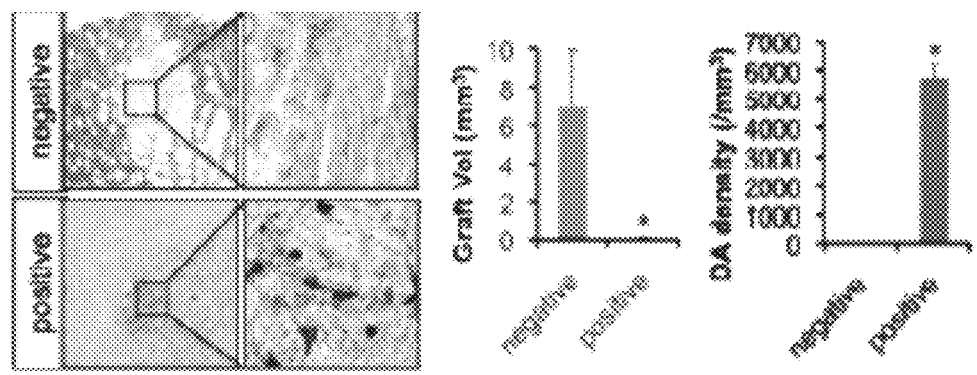
FIG. 1B shows photomicrographs of Corin$^-$Otx2GFP$^-$ cells and Corin$^+$Otx2GFP$^+$ cells transplanted in mouse striatum, as well as graphs of graft volume and density of DDC-stained cells. Cells were stained with tyrosine hydroxylase, Lmx1b, Pitx3 and DDC.

After transplantation into mice striatum, Corin$^-$Otx2GFP$^-$ cells generated disruptive graft with few DA neurons, while Corin$^+$Otx2GFP$^+$ cells generate well integrated graft with enriched DA neurons, as shown by graft pictures as well as the quantitation of graft volume and DA density (FIG. 1B). DA neurons in the graft showed functional midbrain phenotype, shown by coexpression of Lmx1b, Pitx3 and DDC (FIG. 1B).

Example 2—Corin and Fzd5 Antibody Specificity

Even though Corin antibody has been characterized in previous studies, there was no commercially available Fzd5 antibody that works for FACS. Thus, in-house anti-Fzd5 antibody was generated using extracellular domain peptides that are well-conserved between mouse and human. Among the multiple peptides tried, one of the Fzd5 antibody showed specific recognition of Fzd5 in liver-derived HepG2 cells, but no staining in ESCs (data not shown). FACS sorting using Corin and Fzd5 antibody resulted in significant enrichment of FoxA2$^+$Otx2$^+$Lmx1b$^+$ cells (74.8±4.9% Otx2$^+$ cells and 72.8±4.1% FoxA2$^+$ cells), also co-expressing Corin, GLAST and Nestin (data not shown). Upon differentiation, they generated TH$^+$Pitx3$^+$ mDA neurons.

Figure 2:
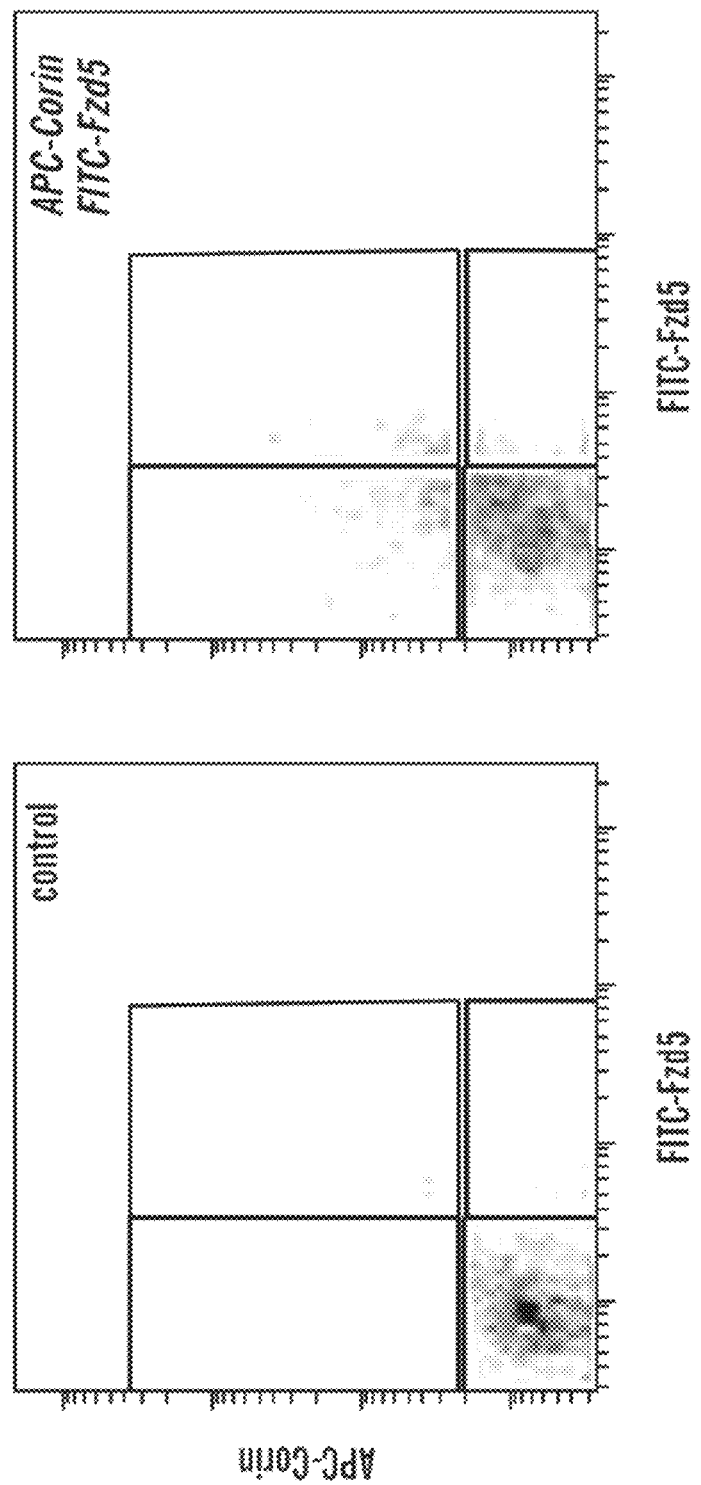
FIG. 2 shows photomicrographs of HepG2 cells and FS cells stained for Fzd5, as wells as FACS data sorting with Corin and Fzd5.

For anti-corin antibody, retrovirus that express human Corin-myc recombinant protein was generated, and cells that were infected with this retrovirus were used to test anti-Corin antibody. Anti-Corin antibody staining overlapped with myc staining, showing specificity of anti-Corin antibody in recognizing human Corin protein (FIG. 2). In addition, we could detect minor population of Corin$^+$Fzd5$^+$ cells after in vitro differentiation of hES cells (FIG. 2).

Example 3—In Vitro Differentiation of Human Embryonic Stem Cells

Several lines of human embryonic stem cells (hESCs) as well as human induced pluripotent stem cells (hiPSCs) were successfully differentiated into mDA neurons using a previously described procedure (Hong et al., 2008) with modification, in which a PA6 feeder layer homogenously induced neural progenitor cells, accompanied by DA differentiation (data not shown; 15.6±1.5% TH$^+$ neurons). When hESCs were differentiated using this protocol, cells with mDA NP characteristics were observed, such as radial glia-like NPs expressing both nestin and Glast, as well as "rostral floor plate-like cells" that express both Otx2 and FoxA2 or Corin and Fzd5 (data not shown).

Although recent studies have shown well-conserved gene expression pattern both spatially and temporally between mouse and human during mDA development (Hebsgaard et al., 2009; Nelander et al., 2009), this study tested whether the floor plate marker Corin and rostral marker Fzd5 can be efficiently used in the human system. Thus, the mDA NP phenotype was induced by coexpression of three key mDA transcription factors, Lmx1a, FoxA2 and Otx2 at the NP stage of differentiating hESCs (Chung et al., 2009; Chung et al., 2011b), and the expression of Corin and Fzd5 was analyzed. Induction of mDA NPs also induced Corin expression. This is in line with another study in which induction of human floor plate cells also induced Corin expression (Fasano et al., 2010). Most of the Corin expression overlaps FoxA2 expression, suggesting that Corin is a useful marker for floor plate cells in the human system. In addition, exogenous expression of three factors induced Fzd5 expression, with good overlap with Otx2 expression, suggesting that Fzd5 is a good marker for rostral NP in the human system as was observed in the mouse system. Furthermore, purification of $Corin^+Fzd5^+$ cells by FACS significantly enriched $Lmx1a^+Lmx1b^+FoxA2^+Gast^+Corin^+$ mDA NPs, further supporting the usefulness of this two-marker combination for purifying human mDA NPs.

Example 4—Purification of Human ESC or Human iPSC-Derived mDA Neural Progenitors Neuronal Differentiation into NP Cells Using PA6 Stromal Cells hESC lines, H7 and H9 (provided by WiCell Research Institute) and hiPSC lines, iPS (IMR90) and iPS-DF4-3 (provided by WiCell research Institute) are cultured on mitotically inactivated mouse embryonic fibroblasts (MEFs) in DMEM/F12 medium with 20% knockout serum replacement, penicillin (100 IU/mL), streptomycin (100 g/mL), 1 mmol/L L-glutamine, 1% non-essential amino acids, 0.1 mmol/L β-mercaptoethanol, and 4 ng/mL basic fibroblast growth factor (all from Invitrogen). For the maintenance of undifferentiated hESCs, cultures are passaged about once every week using a collagenase IV (Invitrogen) treatment and then small clusters are transferred onto freshly prepared MEF feeders. Neural differentiation of hESCs is induced by co-culture on PA6 stromal cells (Kawasaki et al., 2000) or PA6 cells stably over-expressing sonic hedgehog (PA6-SHH). The PA6 co-culture system is used since it efficiently induces neural progenitor cells and they can easily remove them during FACS. Undifferentiated hESC or hiPSC colonies are detached by incubation with collagenase IV followed by gentle dissociation into small clusters, plated on a layer of PA6 stromal cells in N2 media are cultured for 7 days, and then passaged on freshly prepared PA6-SHH feeders for ventralization until rosettes appear, about 14 days. Rosettes are isolated mechanically and NP cells are plated on PLO/FN-coated plates for further expansion.

For neuronal differentiation, NP cells are cultured by withdrawing bFGF for 14 days or more. For FACS sorting, hESC- or hiPSC-derived NP stage cells (day 28 of in vitro differentiation) are stained and subjected to FACS. The purity of all sorted fractions are determined by re-analysis using FACS as well as by immunocytochemistry. Purified cells are plated onto PLO/FN-coated plates in NP media for analysis, further expansion or differentiation.

Neural Differentiation into NP Cells Using MS5 Stromal Cells

Human ES (hES) cell lines, H1, H9 (provided by WiCell Research Institute) and HSF-6 (University of California, San Francisco, Calif., USA), are cultured on mitotically inactivated mouse embryonic fibroblasts (MEFs) in DMEM/F12 medium with 20% knockout serum replacement, penicillin (100 IU/mL), streptomycin (100 lg/mL), 1 mmol/L L-glutamine, 1% non-essential amino acids, 0.1 mmol/L b-mercaptoethanol, and 4 ng/mL basic fibroblast growth factor (bFGF) (all from Invitrogen, Carlsbad, Calif., USA). For the maintenance of undifferentiated hES cells, cultures are passaged about once every week by mechanical dissection and then small clusters are transferred on freshly prepared MEF feeder.

Neural differentiation of hES cells is induced by co-culture on MS5 stromal cells or MS5 cells stably over-expressing sonic hedgehog (MS5-SHH). MS5 stromal feeder cells were maintained in a-minimum essential medium containing 10% fetal bovine serum and 2 mmol/L L-glutamine (Barberi et al. 2003). Undifferentiated hES colonies are detached from MEF feeders by incubation with 200 U/mL collagenase IV (Invitrogen) for 15 min at 37° C., followed by gentle dissociation into small clusters with pipet and then cells are resuspended in serum-free N2 medium with 0.2 mmol/L ascorbic acid (AA; Sigma-Aldrich, New London, N.H., USA). The clusters on a layer of MS5 stromal cells are cultured for 7 days, and then passaged on freshly prepared feeder of MS5-SHH, and further cultured until rosettes appear, about 14 days. Rosettes are isolated mechanically or using dispase. NP cells are frozen by suspension of small clusters in FBS containing 10% dimethyl sulfoxide and placed in a Styrofoam container at 80° C. to ensure a gradual decrease in temperature. After 24 h, frozen cells are moved to a liquid nitrogen tank. Frozen NP cells are thawed in a 37° C. water bath, and then plated on PLO/FN-coated plates in N2-bFGF media.

For further differentiation into neuronal differentiated (ND) cells, the NP cells are cultured by withdrawing bFGF from the media for 14 days or more.

Neural Differentiation Using bFGF Withdrawal and Embryoid Body Formation

For hES differentiation by forming embryoid bodies (EBs), hES cell colonies are detached intact by incubation with dispase (0.2 mg/ml) at 37° C. for 30 min and transferred to ES cell medium without bFGF for four days, forming EBs. EBs are plated onto tissue culture plate in N2-bFGF media for 8-10 days until rosettes appear. Rosettes are then treated as described above.

NP Cell Differentiation Using TGF-β and Noggin

For monolayer differentiation of hES cell, confluent hES cell cultures devoid of MEF was differentiated by changing media to knockout serum replacement media with 10 nM TGF-b inhibitor SB431542 (Sigma) and 500 ng/ml of Noggin (R&D systems), until rosettes appear, at about 5 days in culture. TGF-β inhibitor is withdrawn from differentiation after 5 days and increasing volumes of N2 media were added starting day 5 of differentiation. Mechanically-isolated rosettes are plated on PLO/FN-coated wells in N2-bFGF media for further treatment and sorting in the presence of different combination of signaling molecules such as SHH (50 ng/ml; R&D systems), Wnt1 (50 ng/ml; Peperotech), Wnt5a (50 ng/ml; R&D systems) and FGF8 (50 ng/ml; R&D systems).

Example 5—FACS Sorting of Human mDA NP Cells

Cells are harvested after expansion of rosettes in the optimized growth factor condition for 7 days, using 0.05% trypsin/EDTA (Invitrogen), gently dissociated into a single-cell suspension, and resuspended in HBSS (Invitrogen) containing 20 mM D-glucose (Sigma-Aldrich), penicillin-streptomycin (Invitrogen), and 2% FBS (Invitrogen). Samples are filtered through cell strainer caps (35 μm mesh; BD Biosciences) and then subjected to surface marker staining as follows: FITC-conjugated anti-Fzd5 antibody and APC-conjugated anti-Corin antibody are added for 30 minutes, and cells are then washed and subject to FACS using a FACSAria cell sorter and FACSDiva software (BD Biosciences). Cell debris and dead cells are excluded by forward and side scatter gating. Cells without staining or with single staining are used as controls to set the gating. The purity of all sorted fractions is determined by reanalysis using FACS as well as by immunocytochemistry and cell counting. Sorted cells are plated on PLO/FN-coated wells in N2bFGF media for further treatment, expansion, differentiation and analysis.

Example 6—Immunofluorescent Analysis of Human mDA NPs

For immunofluorescent staining, FACS-sorted human mDA NP cells on coverslips and tissue sections were rinsed with PBS and incubated with blocking buffer (PBS, 10% normal donkey serum, 0.1% Triton X-100) for 15 minutes. Coverslips/sections were then incubated overnight at 4° C. with primary antibodies in blocking buffer. The following primary antibodies were used: rabbit anti-FoxA2 (1:1,000; Abcam), goat anti-Otx2 (1:2,000, Neuromics), rabbit anti-Corin (1:1,000), guinea pig anti-Lmx1b (1:10,000, a gift from Dr. Carmen Birchmeier), rabbit anti-Fzd5 (1:1,000), sheep anti-TH (1:1,000), rat anti-DAT (1:1,000; Chemicon), rabbit anti-vesicular monoamine transporter 2 (anti-VMAT2; 1:1,000; PelFreez), rabbit anti-Lmx1a (1:1,000;), sheep anti-L-aromatic amino acid decarboxylase (anti-AADC; 1:200, Chemicon), rat anti-Dopamine transporter (anti-DAT; 1:1,000), rabbit anti-Pitx3 (1:250; Invitrogen), rabbit anti-Nurr1 (E-20; 1:300; Santa Cruz Biotechnology Inc.), mouse anti-engrailed 1 (clone 4G11; 1:40), anti-HNA (1:400, Chemicon), mouse anti-NeuN (1:200; Chemicon), rabbit anti-b-tubulin (1:1,000, Covance), mouse anti-Nestin (1:100; DSHB), guinea pig anti-GLAST (1:1,000, Chemicon), mouse anti-BrdU (1:1,000; Invitrogen), anti-Oct4 (1:100, DSHB), anti-nanog, rabbit anti-Ki67 (1:2,000; Novocastra Ltd.). The coverslips/tissue sections were subsequently incubated in fluorescent-labeled Alexa Fluor secondary antibodies for 1 hour at room temperature. After rinsing in PBS, Hoechst 33342 (4 µg/ml) was used for counterstaining, and coverslips/tissues sections were mounted onto slides in Mowiol 4-88 (Calbiochem).

Example 7—Purification of Mouse ESC-Derived mDA NP Cells by FACS

J1 embryonic stem cell (ESC) lines are differentiated in vitro using the procedure described by Chung et al. (2006a), and subjected to FACS at the NP stage as described in Chung et al. (2006a). Briefly, trypsinized cells are stained using fluoroscein isothiocyanate (FITC)-conjugated anti-Fzd5 antibody and allophycocyanin (APC)-conjugated anti-Corin antibody. Affinity-purified primary antibodies are directly labeled with FITC or APC prior to use, to reduce sample preparation time for FACS as well as background staining. Unstained cells or single stained cells are used as controls. The purity of all sorted fractions is determined by re-analysis using FACS as well as by immunocytochemistry. FACS-purified cells are plated onto poly-L-ornithine (PLO) and fibronectin (FN) coated plates in NP media (N2 medium (Johe et al., 1996) supplemented with laminin and bFGF) for analysis, further expansion or differentiation.

Example 8—Analysis of Cell Phenotype of Mouse Corin$^+$Fzd5$^+$ Cells at the NP Stage To further confirm the purified cells' phenotype, mouse cells prepared as in Example 7 are fixed 1 hour or 1 day after FACS and assayed for coexpression of other mDA NPs markers such as FoxA2 (abcam), Otx2 (Neuromics), Lmx1a, Lmx1b and En1 (Clone 4G11; DSHB), using double negative cells and Corin$^+$OtxGFP$^+$ cells as controls. Also, to check the nature of mDA NPs as immature radial glia-like NPs, cells are stained using antibody against GLAST (Chemicon), Vimentin (DSHB), Nestin, β-tubulin and GFAP. Efficiency of removing pluripotent cells is monitored using ESC markers, SSEA1, Oct4 and Nanog. Confocal analysis is performed with a Zeiss LSM510/Meta Station. Cell counting is done by random sampling using StereoInvestigator image capture equipment and software (Microbright Field, Williston, Vt.) from at least 5 independent in vitro differentiation and FACS sorting experiments (n=5) using double negative cells and Corin$^+$OtxGFP$^+$ cells as controls. The proportion of mDA NPs (% Corin$^+$Otx2$^+$/Hoechst$^+$) and the proportion of immature pluripotent cells (% Nanog+/Hoechst$^+$) is counted. Corin$^+$Otx2$^+$ cells as markers of mDA NPs as shown in preliminary data represent a better combination for cell counting than the double cell surface marker combination Corin$^+$Fzd5$^+$. ANOVA is done using StatView software and if there is significant difference, posthoc analysis is done.

Example 9—Characterization of Differentiation of Purified Mouse Corin$^+$Fzd5$^+$ Cells at the ND Cell Stage Once the phenotype of purified mouse NPs is confirmed, the mouse NPs are analyzed to determine whether they can generate mDA neuronal phenotypes after differentiation (called ND cells; "neuronal differentiation stage" cells). Sorted cells are differentiated in ND-conditioned media (N2 medium supplemented with laminin and conditioned with mixed ND stage cells) for 7 days and fixed for immunocytochemical analysis. ND-conditioned medium has been shown to support the survival of differentiating mDA neurons (Chung et al., 2011a). mDA neuronal characteristics are analyzed by co-labeling with anti-TH antibody along with antibodies against other known mDA neuronal markers, such as Lmx1a, Lmx1b, FoxA2, En-1, Nurr1 (SCBT) and Pitx3. To test the functionality of mDA neurons generated from purified cells, additional immunocytochemistry is done using antibodies against functional DA genes such as DAT (Chemicon) and DDC (Chemicon). In addition, the presence and proportion of A9 vs. A10 neurons is also analyzed by co-labeling TH with A9-enriched marker Girk2 (Alomone Labs) and the A10-enriched marker Calbindin (Swant), followed by cell counting (n=5). Expression of other neural markers is also analyzed, such as β-tubulin, GFAP, 04 (Chemicon), GABA (Sigma), Glutamate (Sigma), ChAT (Chemicon) and 5HT (Sigma). Cell counting was done as described above to determine the proportion of DA neurons (% TH$^+$/β-tubulin$^+$ and % TH$^+$/Hoechst$^+$) and mDA neurons (% TH$^+$Pitx3$^+$/Hoechst$^+$) after differentiation (n=5) using Corin$^-$Fzd5$^-$ cells and Corin$^+$OtxGFP$^+$ cells as controls.

Example 10—Electrophysiological Analysis of Purified Mouse or Human mDA NDs

Materials and Methods:
Differentiated cells are examined using the whole-cell recording configuration of the conventional 'dialyzed' whole-cell patch-clamp technique. Patch electrodes are fabricated from a borosilicate glass capillary (Sutter Instrument Company) using a vertical micropipette puller (Narishige). The patch electrodes are fire-polished on a microforge (Narishige) and have resistances of 1-3 M Ohms when filled with the internal solution described below. The cell membrane capacitance and series resistance are compensated electronically (typically about 80%) using a patch-clamp amplifier (Axopatch-200A; Axon Instruments/Molecular Devices Corp). Current protocol generation and data acquisition are performed using pClamp 8.0 software on an IBM computer equipped with an analogue-to-digital converter (Digidata 1322A; Axon Instruments/Molecular Devices Corp.). Voltage traces are filtered at 2 kHz by using the four-pole bessel filter in the clamp amplifier and stored on the computer hard drive for later analysis. All experiments are performed at room temperature (21° C.-24° C.). For recording of membrane potential in current clamp mode, the patch pipette solution contains (in mM): KCl 134, $MgCl_2$ 1.2, MgATP 1, $Na_2GTP$ 0.1, EGTA 10, glucose 14, and HEPES 10.5 (pH adjusted to 7.2 with KOH). The bath solution contains (in mM): NaCl 126, KCl 5, $CaCl_2$ 2, $MgCl_2$ 1.2, glucose 14, and HEPES 10.5 (pH adjusted to 7.4 with NaOH).

The electrophysiological properties of DA neurons derived from $Corin^+Fzd5^+$ cells are investigated using the electrophysiology methods described above. To identify mDA neurons for recording, a TH promoter-EGFP reporter AAV viral vector is used to mark TH-positive DA neurons (Oh et al., 2009). $Corin^+Fzd5^+$ cells infected with AAV-TH promoter-EGFP at the NP stage are further differentiated for 7 days and then subjected to electrophysiology analysis. The active membrane properties measured includes: current required to generate action potential (in pA), action potential threshold (mV), action potential amplitude (mV), action potential duration (ms), slow AHP duration (ms) and amplitude (mV). In addition, $TH^-EGFP^+$ neurons are assayed for Ih currents, which are characteristic for DA neurons.

Example 11—Physiological Analysis of Purified Human mDA ND Cells

DA Release Assay:

HPLC analyses of dopamine are performed after 24 hours of conditioning at day 14 of neuronal differentiation stage. For the analysis of conditioned media, the proteins from 0.2 ml of media from each well of a 12-well plate are precipitated by adding perchloric acid (PCA) and EDTA at final concentrations of 0.33 M and 0.17 mM, respectively. For the depolarization-induced release, after aspiration of the residual media (0.6 ml), the cells were treated with 0.2 ml of 50 mM KCl in N2 media for 30 minutes at 37° C. Then the media are collected and the proteins are precipitated by the addition of PCA and EDTA as described above. The mixture is centrifuged at 4° C. for 10 minutes at 14,000 g, and the supernatant is used for HPLC analysis. For analysis of DA contents in the cells, cells are allowed a 1-day recovery in fresh medium after which time they are washed, scraped, collected, and vortexed in a chilled (4° C.) 0.24 ml solution of 0.33 M PCA and 0.17 mM EDTA. After centrifugation at 14,000 g for 10 minutes, the intracellular fraction (supernatant) and cell pellet are separated for intracellular DA and protein analysis, respectively. Samples are applied to reverse-phase HPLC using a Velosep RP-18 column and a CoulochemII® electrochemical detector equipped with a 5014 analytical cell (ESA Biosciences, Inc., Chelmsford, Mass.). The flow rate of the mobile phase (0.1 M sodium phosphate buffer at pH 2.65, 0.1 mM EDTA, 0.4 mM sodium octyl sulphate, and 9% methanol) is 0.8 ml/minute. The potentials of the guard cell and the first and the second electrodes in the analytical cell are set at 330, 0, and 310 mV, respectively. Dopamine is identified by retention time and quantified based on peak height using the EZChrom Chromatography Data System.

DA Reuptake Assay:

Cells are washed with PBS and incubated with 50 nM [$^3$H]DA in PBS (51 Ci/mmol, Amersham Co., Buckinghamshire, UK) without or with 10 □M nomifensine (RBI, Natick, Mass., USA), a dopamine transporter (DAT) blocker, to determine non-specific uptake. After incubation for 10 min at 37° C., the uptake reactions are terminated by aspiration of the reaction solution and washing twice with ice-cold PBS. Cells are lysed in 0.5 M NaOH and the radioactivity was measured by liquid scintillation counting (MicroBeta TriLux ver. 4.4 Wallac). Specific DA uptake is calculated by subtracting non-specific uptake (with nomifensine) from uptake value without nomifensine.

Example 12—Physiological Analysis of Purified Mouse mDA ND Cells

Purified mouse NP cells are tested for their ability to generate authentic mDA neurons by DA release and DA uptake, which are critical process in presynaptic mDA neurons. First, the ND cells ("neuronal differentiation stage" cells) derived from purified NP cells are tested to determine whether they can release DA in response to membrane depolarization, using double negative-derived ND cells as control. At day 7 of ND stage, the cells were treated with 50 mM KCl in ND media for 30 minutes. The media is then collected and deproteinized for HPLC analysis. HPLC is done as described in Example 11 and the result is normalized by total protein content (Chung et al., 2002).

Purified ND cells are also analyzed for their ability to specifically uptake DA using the dopamine transporter (DAT). At day 7 of ND stage, the ND cells are incubated with 50 nM [$^3$H]DA in PBS (Perkin Elmer) without or with 10 □M nomifensine (RBI), a dopamine transporter (DAT) blocker, to determine non-specific uptake of DA. The ND cells are washed and lysed, followed by liquid scintillation counting. Specific DA uptake is calculated by subtracting non-specific uptake (with nomifensine). Again, double negative-derived ND cells are used as control.

Example 13—Expansion and Cryopreservation of Purified Mouse mDA NPs

One of the major benefits of isolating NPs instead of terminally differentiated neurons is their expandability. Signaling molecules have been associated with mDA NP proliferation, but there have been conflicting results obtained from different systems and experiments. The use of purified populations of mDA NPs provides the opportunity to test the effect of each signaling molecule in a pure cell population without influence from other cell types. Determining the cells' responsiveness to signaling molecules is useful not only for biological characterization of mDA NPs but also to optimally maintain them in vitro. Recently, it was established that mESC and hESC-derived NP cells can be expanded, frozen, and thawed again without losing their proliferative and differentiation potential (Chung et al., 2006b; Hong et al., 2008).

Purified mDA NPs are expanded in NP media in the presence of mDA NP-specific signaling molecules such as SHH (50 ng/ml; R&D systems), Wnt1 (50 ng/ml; Peprotech), Wnt5a (50 ng/ml; R&D systems) and FGF8 (50 ng/ml; R&D systems) as well as more general NP-specific signaling molecules such as Dll4 (500 ng/ml; R&D systems)

and Jag1 (500 ng/ml; R&D systems), alone or in combination, passaging once a week for further expansion or analysis. In addition to the signaling molecules, endothelial cell conditioned media (or insert co-culture), are also tested, which has been shown to provide a niche for neural stem cells (Elkabetz et al., 2008; Shen et al., 2004). The effect of signaling molecules on proliferation of mouse mDA NPs are assayed by growth curve and Ki67$^+$ cell counting during expansion, using cells expanded in NP media without added signaling molecules as control from 5 independent FACS sorting and expansion (n=5). The developmental potential of specific signaling molecule-expanded Corin$^+$Fzd5$^+$ cells is characterized by immunocytochemistry at the NP stage and the ND stage as described above in Example 6.

Example 14—Expansion and Cryopreservation of Purified Human mDA NPs

Determining human mDA NP cell responsiveness to signaling molecules is important not only for biological characterization of human mDA NPs but also for more practical application of human mDA NPs to optimally maintain them in vitro. It has been recently established that mESC and hESC-derived NP cells can be expanded, frozen, and thawed again without losing their proliferative and differentiation potential (Chung et al., 2006b; Hong et al., 2008). Thus, using this protocol, Corin$^+$Fzd5$^+$ cells are frozen and thawed at 1 month, 3 months and 12 months after cryopreservation, and compare the stability of their proliferative/developmental potential during cryopreservation is compared by immunocytochemistry at the NP and ND stage as described above.

Example 15—Transplantation of Corin$^+$Fzd5$^+$ Cells into Aphakia Mice

Aphakia Mice as an Animal Model for Cell-Replacement Therapy for PD

Based on previous findings of selective loss of A9 DA neurons in the SNc of aphakia mice (Hwang et al., 2003), the use of the aphakia mouse as an animal model of PD has been investigated. Aphakia mice displayed nigrostriatal pathway-specific motor deficits that are reversed by L-DOPA, and provided evidence of 'DA supersensitivity' in the striatum (Hwang et al., 2005). Since aphakia mice can breed as homozygote pairs, large number of animals are readily available for systematic behavioral analyses with minimal individual fluctuations, thus are optimal for obtaining best transplantation conditions of human Corin$^+$Fzd5$^+$ cells for further analysis in rats. Thus aphakia mice represent a useful genetic model to test the efficacy of symptomatic PD therapies. Recently, the motor deficit of aphakia mice has been compared to that of control mice and the reversal of these motor symptoms by mouse ES cell-derived transplantation (Moon et al., Manuscript in preparation)

Figure 3A:
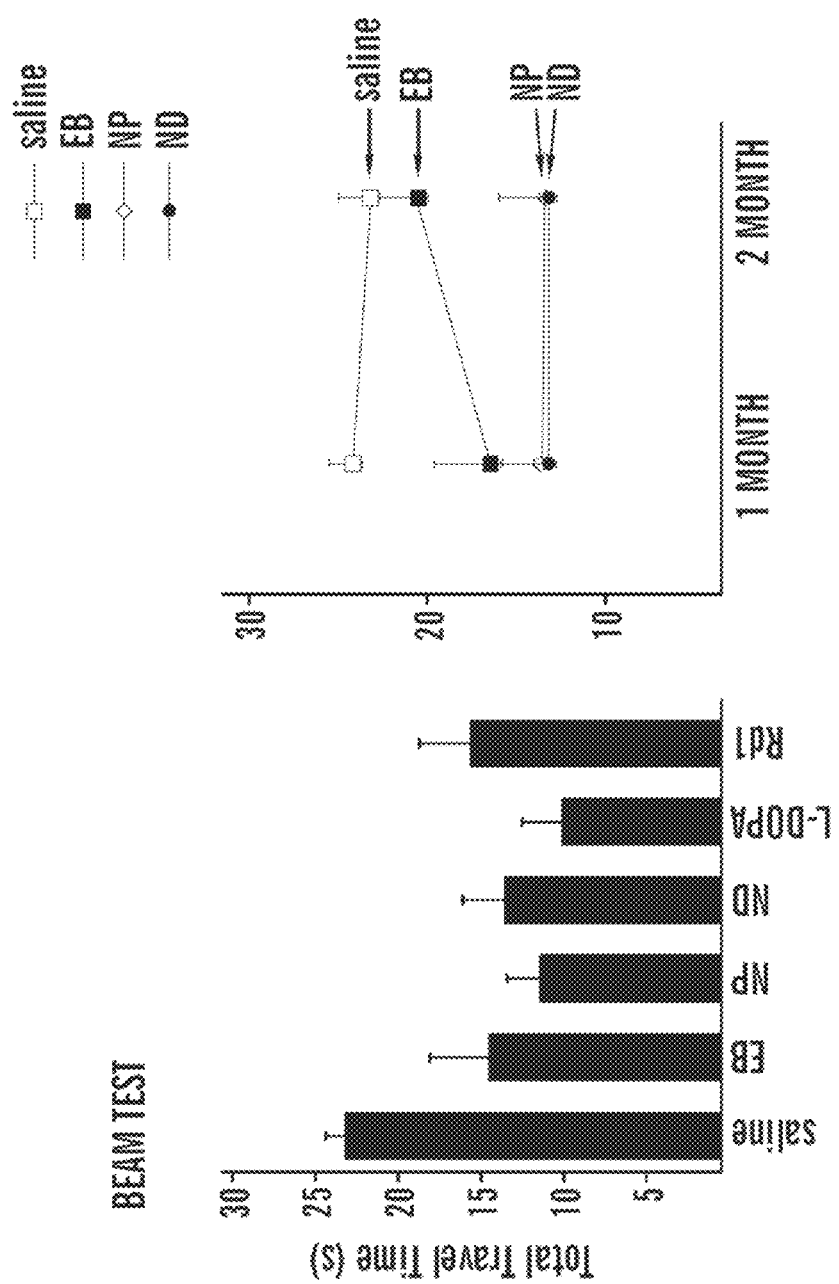
FIG. 3A shows behavioral data from mice performing the challenging beam test that have been transplanted with ESC-derived cells.
Figure 3B:
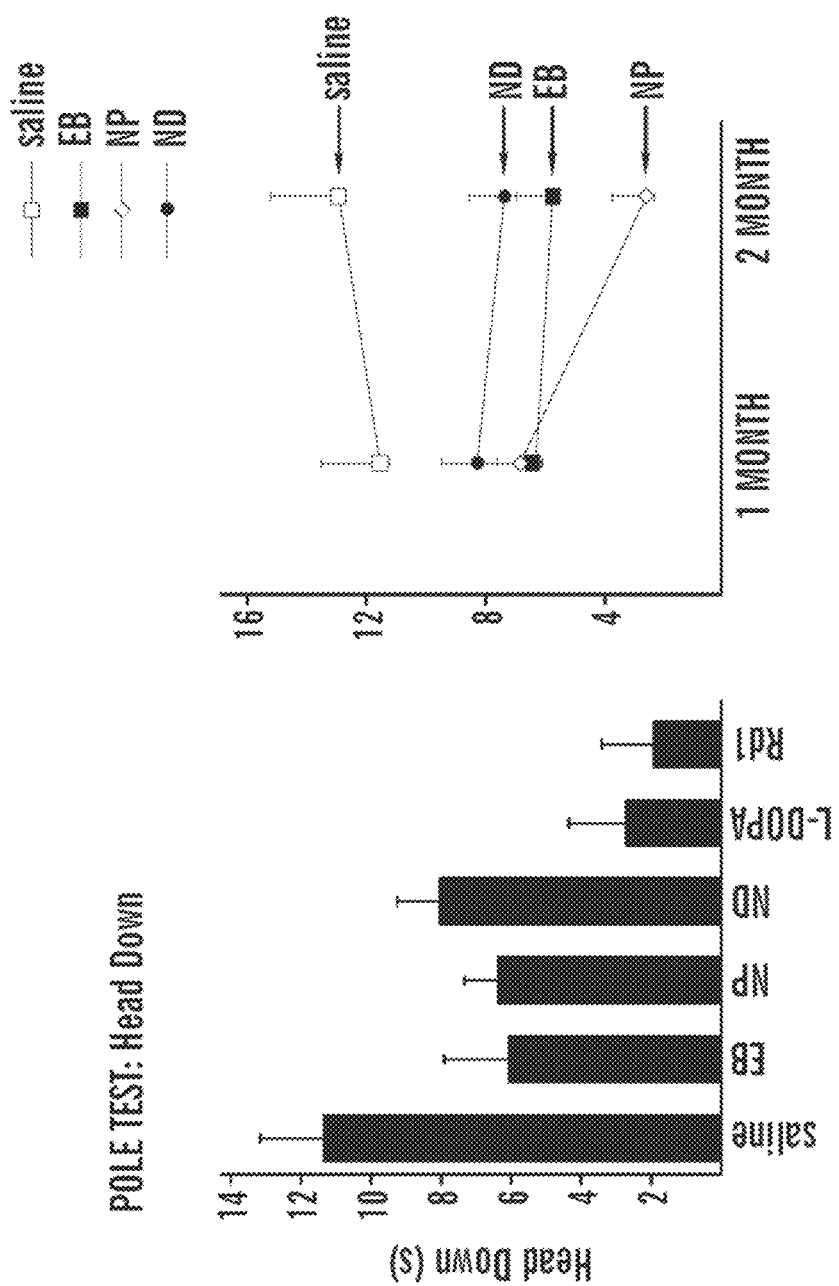
FIG. 3B shows behavioral travel time data from mice performing the pole test that have been transplanted with ESC-derived cells.
Figure 3C:
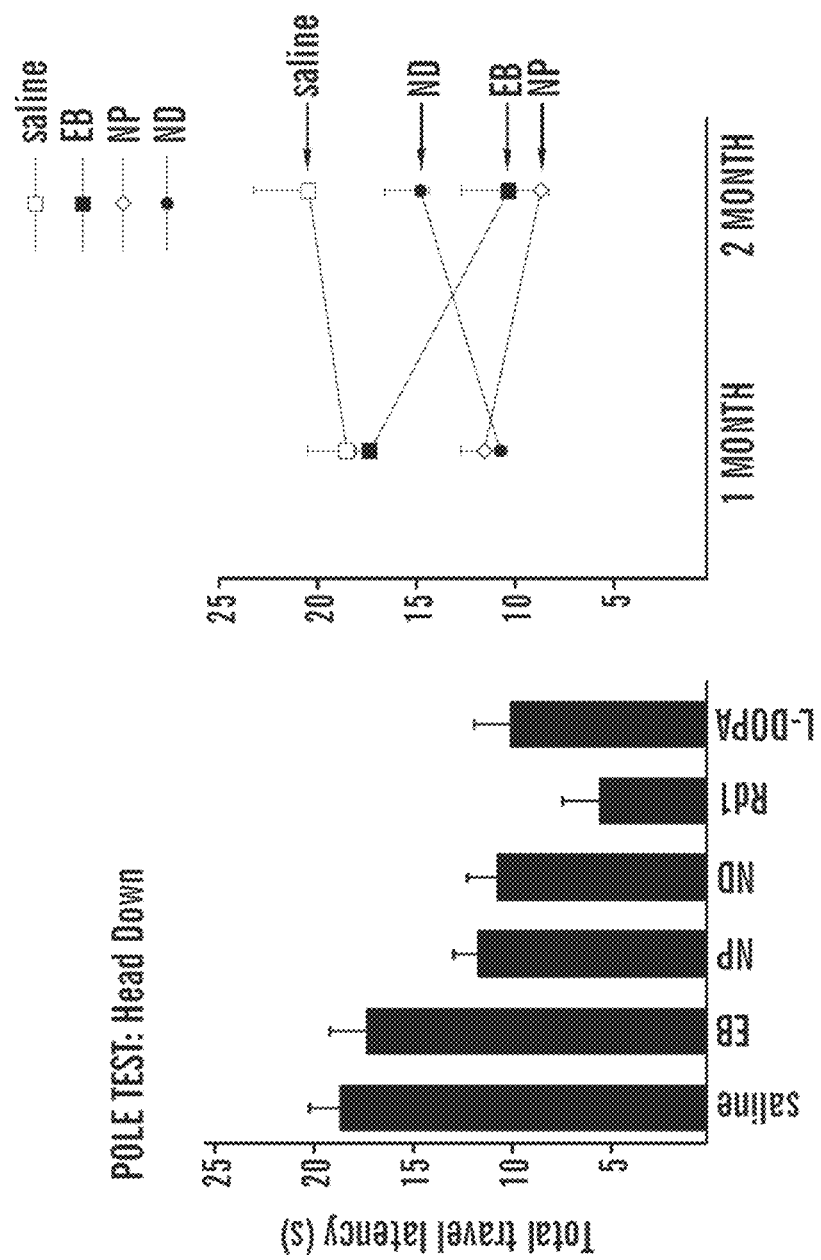
FIG. 3C shows behavioral latency data from mice performing the pole test that have been transplanted with ESC-derived cells.

Aphakia mice transplanted with ESC-derived cells at different stage of differentiation (Embryoid body (EB), NP and ND) as well as L-DOPA treated mice showed significantly faster travel time on the challenging beam compared to the saline-treated group (FIG. 3A). In addition, when placed head upward on top of a vertical pole, aphakia mice took much longer to orient themselves downwards than any other group (FIG. 3B). Total travel latency to travel downward also showed consistent results as head down measurements (FIG. 3C). Blind rd1 mice were used as a positive control.

Thus, aphakia mice perform worse than their age-matched transplanted and L-DOPA controls on a battery of behavioral tests that are sensitive to defects of the nigrostriatal DA system and their function can be significantly restored to the level of L-DOPA-treated mice by cell transplantation. Interestingly, in all these tests, mice treated with NP cells showed the best behavioral recovery, further supporting the long-term goal of identifying and purifying mDA NPs. Similar behavioral recovery of aphakia mice has also been observed after transplantation with Corin$^+$Otx2$^+$ cells (Example 23 and Chung et al., 2011a).

Example 16—Transplantation of Human Corin$^+$Fzd5$^+$ Cells into Aphakia Mice

Optimal transplantation conditions for human Corin$^+$Fzd5$^+$ cells in aphakia mice can be determined both at the NP stage and early ND stage (day 3 of ND stage). To observe the time course of graft maturation, aphakia mice transplanted with human Corin$^+$Fzd5$^+$ cells are sacrificed 1 month, 2 months and 4 months after transplantation. For transplantation, Corin$^+$Fzd5$^+$ cells are expanded for 3 days in NP media to recover from FACS stress and are transplanted either with or without 3 days differentiation in ND conditioned media. Prior to transplantation, cells are infected with Lenti-EF1a-GFP (Hong et al., 2007), which is an efficient system for tracking transplanted cells without silencing during DA differentiation of NPs. Cells are trypsinized, suspended in solution at 150,000 cells/µl and 2 µl of cell suspension is injected bilaterally into the striatum of aphakia mice (from the bregma: AP+0.05, L+0.18, V −0.30, IB 9) using a 22-gauge, 5 µl Hamilton syringe and a Kopf stereotaxic frame (Kopf Instruments). Corin$^-$Fzd5$^-$ cells are also transplanted as control. Prior to surgery, mice receive an i.p. injection of acepromazine (3.3 mg/kg) and atropine sulfate (0.2 mg/kg) followed by anesthesia with an i.p. injection of ketamine (60 mg/kg) and xylazine (3 mg/kg). To prevent rejection of grafted cells, mice are immunosuppressed by s.c. injection of cyclosporine A (15 mg/kg) diluted in extra virgin olive oil each day starting with a double-dose injection 1 day before surgery.

Example 17—Histological Analysis of Human Corin$^+$Fzd5$^+$ Cells in Aphakia Mice Immunocytochemical Analysis of Corin$^+$Fzd5$^+$ Cell Grafts The in vivo developmental potential of Corin$^+$Fzd5$^+$ cells is analyzed by immunohistochemistry. Transplanted aphakia mice are terminally anesthetized with an i.p. overdose of pentobarbital (150 mg/kg) and perfused intracardially with 0.1% heparin saline followed by 4% paraformaldehyde after 1 month, 2 months or 4 months post-grafting. Two hours before sacrifice, animals are injected with BrdU (100 mg/kg) to trace proliferating cells in the graft, which is an important factor for safety of the graft. Brains are removed, postfixed in 4% paraformaldehyde, equilibrated in 20% sucrose, and sectioned on a freezing microtome in 40-µm coronal slices. The phenotypic expression, morphological and differentiation properties of the grafts are analyzed by immunofluorescence. mDA neuronal marker expression is assessed by co-labeling with TH antibody along with antibodies against mDA-specific transcription factors (FoxA2, Lmx1a, Lmx1b, Nurr1), functional DA genes (DDC, DAT, VMAT2) and A9- or A10-specific genes (AHD2, Girk2 or Calbindin). Co-labeling is also done using antibodies against TH and various synaptic markers (Synapsin, Synaptophysin, Synaptobrevin) to analyze synaptic integration of grafted mDA neurons into host neural networks. To check for safety of the graft, proliferating cell markers such as PCNA, Ki67 and BrdU are analyzed as well as pluripotency markers, SSEA1, Oct4 and Nanog. Confocal analysis is performed using a Zeiss LSM510/Meta Station (Carl Zeiss, Thornwood, N.Y.). For identification of signal co-localization within a cell, optical thickness is kept to a minimum, and orthogonal reconstructions are obtained.

Stereological Analysis of Corin$^+$Fzd5$^+$ Cell Grafts

Stereological analysis is used to study the overall structure of Corin$^+$Fzd5$^+$ cell grafts. All cell counting and estimation of total cell number in the graft is done using the StereoInvestigator image-capture equipment and software (MicroBrightField) and a Zeiss Axioplan I fluorescent microscope using the Optical fractionator probe from every 6th section. Total DA neurons (TH$^+$), total mDA neurons (TH$^+$Pitx3$^+$), total proliferating cells (Ki67$^+$) are counted and estimated from control vs. Corin$^+$Fzd5$^+$ grafts. Since Corin$^+$Otx2$^+$ mDA NPs, unlike mDA neurons, have exhibited significant migratory function in the host striatum, reaching up to >3.3 mm length in the entire striatum (Chung et al., 2011a), the migration of transplanted Corin$^+$Fzd5$^+$ cells along AP axis is also measured by counting total GFP$^+$TH$^+$ cell numbers in each of the every 6th coronal sections. Such migratory function could be an important property in achieving maximum host integration for cell replacement therapy. Total graft volume is also measured as an independent measure of graft survival and graft safety using StereoInvestigator equipment and software with Cavalieri estimator probe from every 6th section.

Example 18—Behavioral Effects of Corin$^+$Fzd5$^+$ Cells Transplanted into Aphakia Mice To test whether Corin$^+$Fzd5$^+$ grafts can reverse functional deficits shown in aphakia mice, separate sets of aphakia mice are transplanted with hESC-derived or hiPSC-derived Corin$^+$Fzd5$^+$ cells or Corin$^-$Fzd5$^-$ cells, using optimized transplantation conditions. An hESC line and a hiPSC line are used. Behavioral tests are performed before transplantation and at 1, 2, and 4 months post transplantation, using double negative cell-transplanted mice as controls. Locomotor activity is measured as a gross motor function test. Then, more nigrostriatal pathway-sensitive motor behavioral tests are performed, such as cylinder, challenging beam, and pole tests.

Locomotor Activity:

Mice are placed in a polycarbonate cage surrounded by photobeam detectors. Horizontal and vertical photobeam breaks are recorded as a measure of locomotor activity. Locomotor (ambulatory) activity, defined as a consecutive breaking of photobeams, is recorded for 24 hours.

Cylinder Test:

Spontaneous movement is measured by placing animals in a small transparent cylinder for 3 minutes. A rear is counted when an animal makes a vertical movement with both forelimbs removed from the ground.

Challenging Beam Traversal Test:

The beam (length, 1 m) starts at a width of 3.5 cm and gradually narrows to 0.5 cm in 1 cm increments. Animals are trained for 2 days to traverse the length of the beam for a total of three trials. Both the number of steps taken by each animal and time to traverse across three trials are analyzed.

Pole Test:

Animals are placed head upwards on top of a vertical wooden pole 50 cm in length. Once placed on the pole, animals orient themselves downward and descend the length of the pole. All animals receive 2 days of training consisting of three trials for each session. On the test day, animals receive three trials, and the time to orient downward and total travel time is measured. After final behavioral analysis, the mice are sacrificed and analyzed for histology as described above. Total DA neuronal numbers or total mDA neuronal numbers are correlated with the results from behavioral analyses.

Example 19—Electrophysiological Analysis of Corin$^+$Fzd5$^+$ Cells Transplanted into Aphakia Mice Human Corin$^+$Fzd5$^+$ cells are also tested to determine whether they can mature in vivo to fully show electrophysiological property of authentic mDA neurons. To identify mDA neurons for recording, the cells are infected with AAV-TH promoter-EGFP prior to transplantation to efficiently mark TH-positive DA neurons (Oh et al., 2009). An independent group of transplanted aphakia mice is tested for behavior at 1, 2, and 4 months after transplantation, prior to being anesthetized with isoflurane and decapitated 4 months after transplantation. The striatum is dissected and placed in ice-cold artifact CerebroSpinal Fluid (ACSF). Parasagittal slices (350 μm thick) are cut on a vibratome and incubated in 32-34° C. ACSF for at least 1 h before recordings. Slices are transferred to a recording chamber on the stage of an upright microscope (Nikon E600FN). GFP$^+$ DA neuron-like cells are identified using a fluorescence camera (CoolSNAP EZ, Photometrics), and subsequently visualized using infrared differential interference contrast optics. The active membrane properties measured include: current required to generate an action potential (in pA), action potential threshold (mV), action potential amplitude (mV), action potential duration (ms), slow AHP duration (ms) and amplitude (mV). In addition, the TH$^-$EGFP$^+$ neurons are assayed for Ih currents, which are characteristic for DA neurons.

Example 20—Transplantation of Mouse or Human Corin$^+$Fzd5$^+$ Cells into 6-OHDA Lesioned Rats Materials and Methods Lesion and Transplantation:

Sprague-Dawley rats (250-300 g; Taconic) are unilaterally lesioned by injecting 6-OHDA into the medial forebrain bundle. The lesioned animals are evaluated for their rotational behavior following treatment with amphetamine (4 mg/kg) and those with more than 500 ipsilateral turns to the lesioned side in a 90 min trial (considered having >97% striatal DA lesion) are used for transplantation. Corin$^+$Fzd5$^+$ cells after 3 days of recovery post FACS are used for transplantation along with Corin$^-$Fzd5$^-$ cells as a negative control. Prior to transplantation, cells are infected with Lenti-EF1a-GFP for tracking transplanted cells. Each animal receives an injection of 2 μl (150,000 cells/μl) into one tract with 2 deposits (1 μl each) into the right striatum (from Bregma: A +0.10, L −0.30, V −0.50 and −0.45, IB 0). To prevent rejection of grafted mouse NP cells, rats are immunosuppressed by s.c. injection of cyclosporine A (15 mg/kg) diluted in extra virgin olive oil each day starting with a double-dose injection 1 day before surgery.

Using another method, control or double positive cells, analyzed for viability, are resuspended in N2AA medium containing 20 ng/ml BDNF, 10 ng/ml GDNF, and 20 uM Boc-Asp(OMe) fluoromethyl ketone (BAF; Sigma-Aldrich) at a density of 100,000 cells per microliter. Sprague-Dawley rats with unilateral 6-hydroxydopamine lesions are obtained from Charles River Laboratories (n=16 per time point×4 time point=64 rats+16 extra rats; total 70 rats). The severity of the lesions is measured prior to transplantation by rotational behavior in response to amphetamine (4 mg/kg i.p.) and apomorphine (0.05 mg/kg). Rats receive grafts into the lesioned striatum with 3 μl of cell suspension into one tract with two deposits (coordinates from bregma: anterior-posterior 0.0, lateral −0.3, ventral −0.55 and −0.45). To prevent rejection of grafted mouse ES cells, rat hosts (and control animals) receive immunosuppression by s.c. injections of cyclosporine A (15 mg/kg) diluted in extra virgin oil each day starting with a double-dose injection 1 day before surgery. Amphetamine-induced rotational behavior was measured again at 1, 2, 4 and 6 months post-transplantation. The animals are sacrificed 1, 2, 4 and 6 months post-transplantation. Anesthesia is performed by administration of an i.p. overdose of pentobarbital (150 mg/kg), and animals were perfused intracardially with 0.1% heparinized saline followed by 4% paraformaldehyde. Brains are removed, postfixed in 4% paraformaldehyde, equilibrated in 20% sucrose, and sectioned on a freezing microtome in 40-μm coronal slices.

Immunohistochemistry and Graft Analysis:

To analyze the integration of DA graft into the host neural networks, DA fiber innervation to the host striatum is measured. This is an important criterion, considering transplantation of pluripotent cell-derived cells sometimes resulted in suboptimally-functioning grafts without proper connectivity with the host striatum, although a large number of $TH^+$ cells can be found inside the grafts (Wernig et al., 2008). 6OHDA rats have lower endogenous DA fiber background in the striatum compared to aphakia mice, and are thus a better system for this analysis.

6-OHDA-Lesioned Rats as an Animal Model for PD

Transplantation of low density ESCs into 6OHDA-lesioned rats has been shown to generate DA grafts with functional recovery, illustrating the usefulness of ESC-derived progenies for cell replacement therapy of PD (Bjorklund et al., 2002). Furthermore, purified ESC-derived $Corin^+Otx2^+$ mDA NPs have been shown to efficiently generate DA graft accompanied by functional recovery in 6-OHDA-lesioned rats (Chung et al., 2011a).

The transplantation of hiPSC-derived NPs into the rodent striatum was optimized. Following transplant 300,000 hIPSC-NPs generated optimal graft size (4.74±1.94 mm³) with robust survival of mDA neurons (26,882±9089 $TH^+$ neurons per graft) was observed. Mature mDA neuronal characteristics were shown by coexpression of TH with VMAT2, Nurr1 and En1 (data not shown).

Example 21—Behavioral Analysis of Rats Transplanted with $Corin^+/Fzd5^+$ Cells

Amphetamine-Induced Rotation Behavior:

ES-derived DA neurons have been shown to be capable of significantly reducing drug-induced rotations in 6 OHDA-lesioned rats, and rotational behavior test are done as described (Bjorklund et al., 2002). Each rat receives amphetamine treatment (2.5 mg/kg, i.p., dissolved in 0.9% sterile saline) and is then placed in the automated rotometer bowl. The rotation of the rat is recorded by a computer over a 90-minute period. The number of complete) (360° turns is used.

Cylinder Test:

The cylinder test is used as a motor test of the rat's spontaneous forelimb use asymmetry (Kim et al., 2002). A rat is placed in a transparent plastic cylinder and videotaped until it performs 20 vertical paw placements against the cylinder wall. The percentage of the impaired paw use to the total contacts is calculated.

Skilled Paw Reaching:

The motor asymmetry created by the unilateral 6-OHDA lesion will result in a side bias in the animal performance using fine motor skills. Animals are brought to 80% of their free feeding weight by food deprivation, after which they are tested over 10 consecutive days. The animals are placed into the test boxes for 20 minutes. For the first 5 days, a double staircase is baited with 40 chow pellets on each side. On day 10, the left and right staircase is baited with 40 pellets separately ("forced choice" test), allowing the animals 5 minutes for food retrieval on each side. After each test the number of pellets taken and the number eaten is counted separately.

Adjusting Step Test:

Forelimb akinesia is assessed by the adjusting stepping test. The hind limbs and one forepaw are held so that another forepaw was placed on a table; the rat is then passively moved sideways along the table for 0.9 m within 5 seconds, first in the forehand direction and then in backhand direction. Stepping numbers over five cycles are then averaged for each forepaw. The results are expressed as a percentage of steps in lesioned side compared with the nonlesioned side.

Example 22—Striatal Dopamine Analysis in Rats Transplanted with $Corin^+/Fzd5^+$ Cells Another important criteria of authenticity of mDA NPs is whether they can generate mDA neurons that can release DA in the host striatum. This is also critical for proper graft function. An independent group of 6OHDA-lesioned rats is transplanted with $Corin^+Fzd5^+$ cells for DA release analysis in the host striatum. They are analyzed for behavior at 1, 2, and 4 months after transplantation, and then sacrificed and DA release performed by HPLC analysis. Lesioned or nonlesioned sides of the ungrafted striata are used as positive and negative controls. After sacrifice at 4 months after transplantation, brains are quickly removed on an iced plate, the striatum is extracted and homogenized with PCA and EDTA and centrifuged at 14,000 g for 10 minutes. The supernatant is used for HPLC and the cell pellet is used for protein analysis to normalize HPLC data. Samples are analyzed as described (Chung et al., 2002).

Figures 8A, 8B, 8C, 8D, 8E:
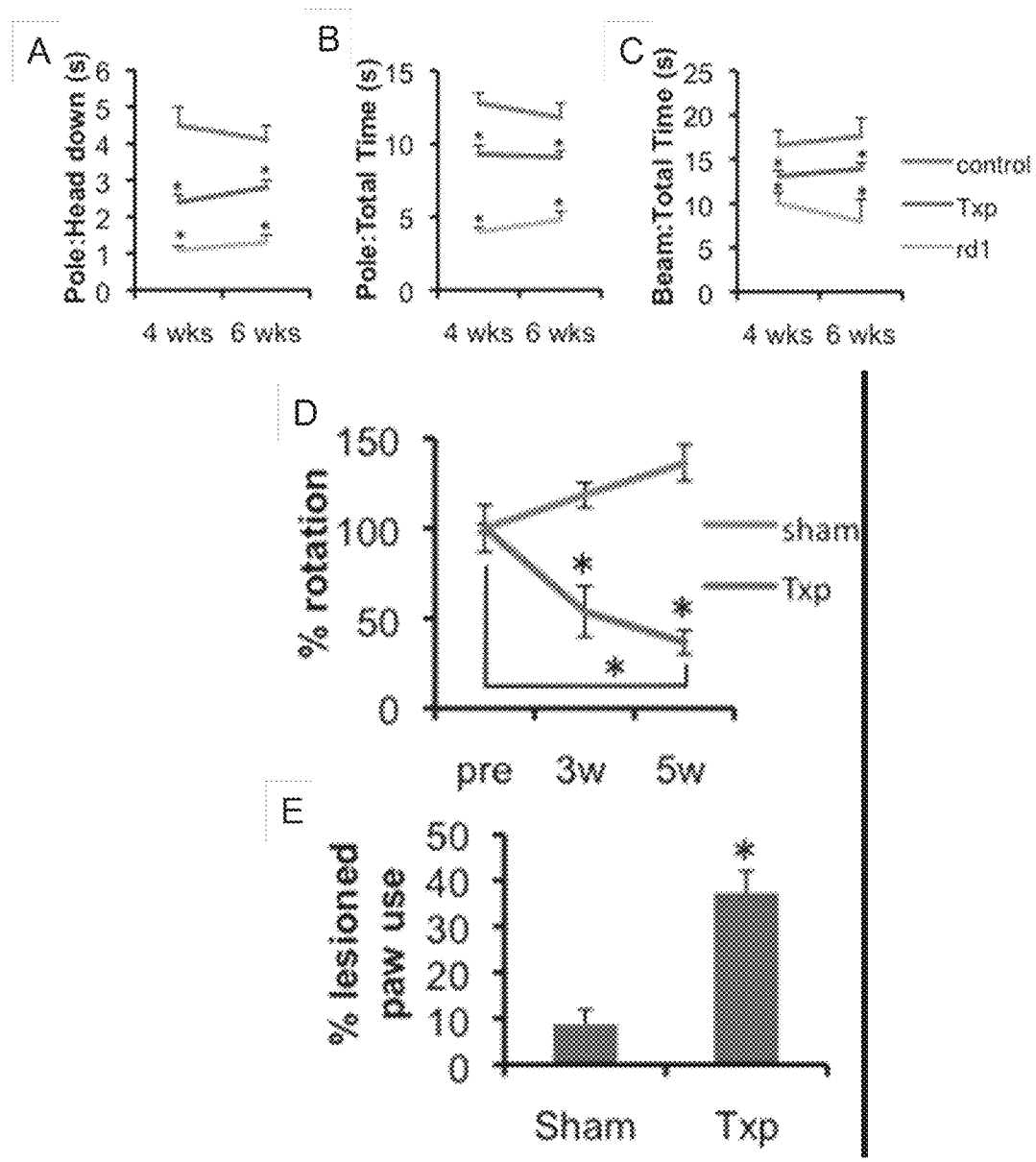
FIG. 8A-8C show graphs of behavioral data from aphakia mice transplanted with Corin$^+$Otx2GFP$^+$ cells.
FIGS. 8D and 8E show graphs of behavioral data from 6OHDA-lesioned rats transplanted with Corin$^+$ Otx2GFP$^+$ cells.

Example 23—Behavioral Analysis of Rats and Mice Transplanted with $Corin^+Otx2GFP^+$ Cells Aphakia mice were transplanted with $Corin^+Otx2GFP^+$ cells, as described in Example 15. Nigrostriatal pathway-sensitive motor behavioral tests were performed on transplanted mice 4 weeks and 6 weeks post transplantation, using mock-transplanted aphakia mice and blind rd1 mice as controls, as described by Hwang et al. (2005) and in Examples 16 and 18. The behavioral tests included cylinder, challenging beam, and pole tests. When placed head upward on top of a vertical pole, aphakia mice transplanted with $Corin^+Otx2GFP^+$ cells took much less time to orient themselves downwards than control aphakia mice (FIG. 8A). Total latency to travel downward also showed consistent results as head down measurements (FIG. 8B). In addition, aphakia mice transplanted with $Corin^+Otx2GFP^+$ cells required significantly less travel time on the challenging beam compared to the mock-transplanted group (FIG. 8C). These results show that transplanted aphakia mice perform significantly better than their age-matched control aphakia mice on a battery of behavioral tests that are sensitive to defects of the nigrostriatal DA system. Asterisks in FIG. 8A-8C indicate a statistically significant difference from control.

6OHDA-lesioned rats were also transplanted with Corin$^+$Otx2GFP$^+$ cells, as described in Example 20. The in vivo function of Corin$^+$Otx2GFP$^+$ cells after transplantation into the striatum of 6OHDA-lesioned rats was tested using behavioral tests as described in Example 21. Compared to control rats undergoing sham surgery, transplanted rats showed significant motor improvement in both amphetamine-induced rotation (FIG. 8D) and use of lesioned paw by cylinder test (FIG. 8E). Asterisks in FIGS. 8D and 8E indicate a statistically significant difference from control.

Example 24—Optimizing Corin Expression in Mouse ES Cells

Figure 9:
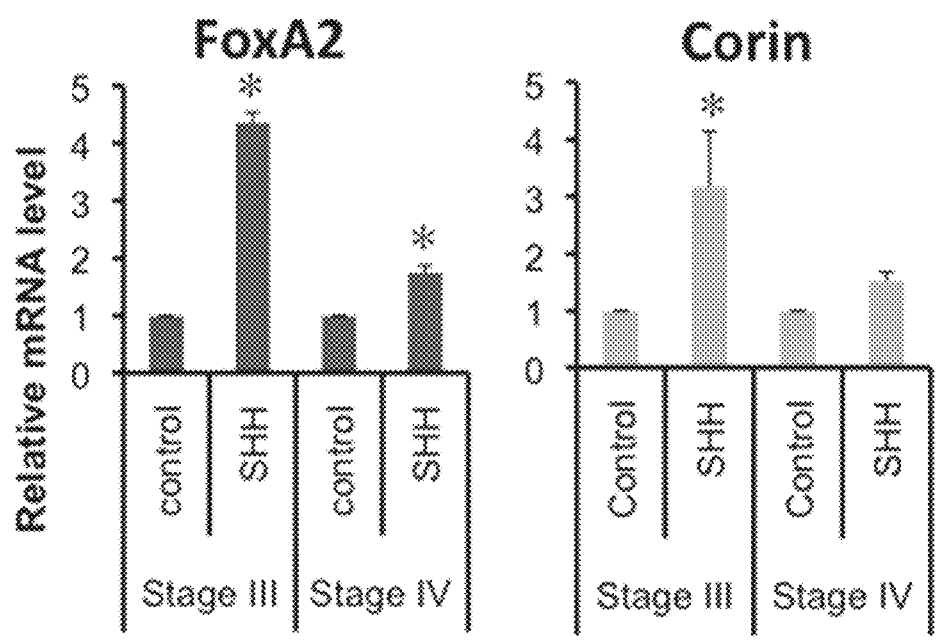
FIG. 9 shows graphs of FoxA2 and Corin mRNA levels in NP cells following exposure to sonic hedgehog protein (SHH) at different timepoints of differentiation.

In order to optimize expression of Corin during differentiation of mouse ES cells (ventralization), differentiating mouse ES cells (prepared as described in Example 1) were treated with SHH-conditioned media either when NP cells start to emerge from EBs (stage 3) or when NP cells are well established following emergence from EBs (stage 4; stages described in Example 1 and FIG. 1A). Relative mRNA levels of FoxA2 and Corin were analyzed using real time PCR as described in Chung et al. 2009. mRNA expression of both FoxA2 and Corin was significantly increased only when the cells were treated with conditioned medium at stage 3 (FIG. 9), showing that there is a time window when differentiating ES cells are responsive to SHH-mediated ventralization.

Example 25—bFGF and FGF8 Support Proliferation of mDA Neural Progenitor Cells

Figure 10:
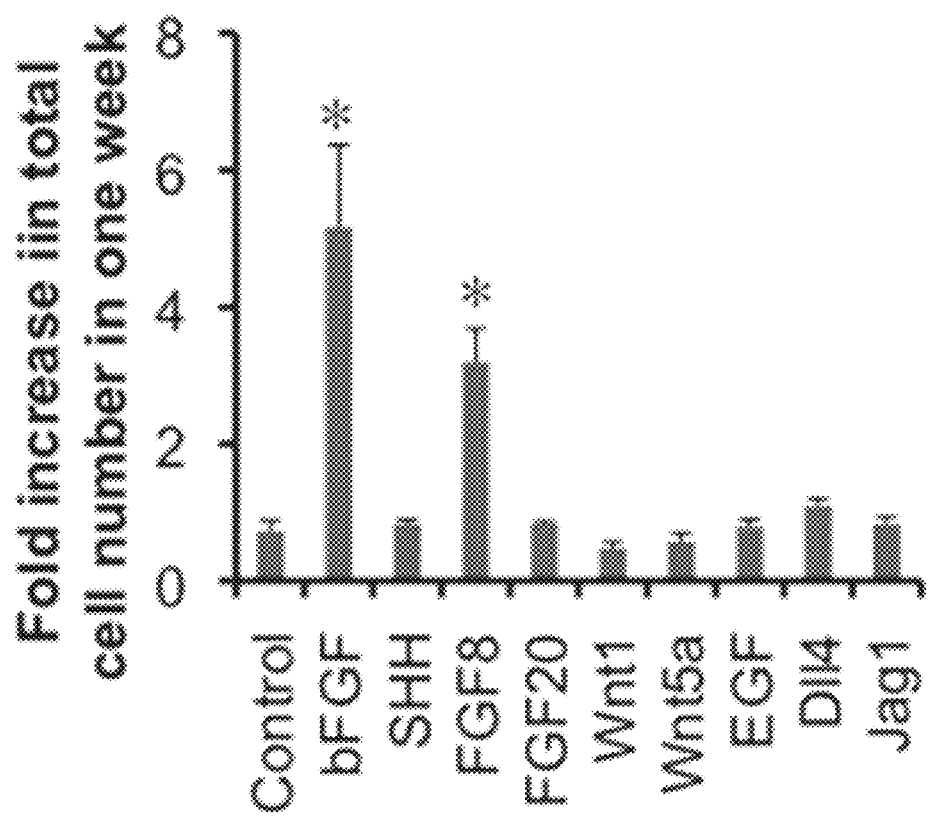
FIG. 10 shows a graph of fold increase in cell number following exposure of NP cells to a variety of protein growth factors as described in Example 24.

The self-renewability (or expandability) of Corin$^+$Otx2GFP$^+$ cells was tested in response to various signaling molecules. Molecules tested included those implicated in the regulation of either mDA NPs (e.g., SHH, FGF8, Wnt1 and Wnt5a) or the proliferation of general NPs (e.g., bFGF, EGF, Dll4 and Jag1) as well as FGF20 that has been implicated in mDA survival. Each candidate molecule was added for a week to mitogen-free media (ND media) surrounding NP cells, which by itself does not support the proliferation of purified cells. At a concentration of 50 ng/ml, only bFGF (FGF2) and FGF8 supported proliferation of Otx2$^+$Corin$^+$ cells, but not SHH, FGF20, Wnt1, Wnt5a, EGF, Dll4 and Jag1 (FIG. 10). Only bFGF and FGF8 generated large proportion of Ki67$^+$ proliferating cells (data not shown). In contrast, differentiated TH$^+$ cells were greatly increased in the presence of other factors (data not shown). These results show that bFGF and FGF8 support the self-renewal of mDA NP, while preventing them from differentiating. In addition, after 1 week, bFGF- or FGF8-treated cells showed the presence of an enriched Nestin$^+$ cell population, whereas cells treated with the other factors showed enriched β-tubulin$^+$ neurons compared to Nestin$^+$ cells (data not shown).

REFERENCES CITED

1. Agid, Y. (1991). Parkinson's disease: pathophysiology. Lancet 337, 1321-1324.
2. Andersson, E. R., Prakash, N., Cajanek, L., Minina, E., Bryja, V., Bryjova, L., Yamaguchi, T. P., Hall, A. C., Wurst, W., and Arenas, E. (2008). Wnt5a regulates ventral midbrain morphogenesis and the development of A9-A10 dopaminergic cells in vivo. PLoS One 3, e3517.
3. Björklund, L., Sánchez-Pernaute, R., Chung, S., Andersson, T., Chen, I., McNaught, K., Brownell, A., Jenkins, B., Wahlestedt, C., Kim, K.-S., et al. (2002). Embryonic stem cells develop into functional dopaminergic neurons after transplantation in a Parkinson rat model. Proc Natl Acad Sci USA 99, 2344-2349.
4. Carlsson, A., Lindqvist, M., and Magnusson, T. (1957). 3,4-Dihydroxyphenylalanine and 5-hydroxytryptophan as reserpine antagonists. Nature 180, 1200.
5. Castelo-Branco, G., Sousa, K. M., Bryja, V., Pinto, L., Wagner, J., and Arenas, E. (2006). Ventral midbrain glia express region-specific transcription factors and regulate dopaminergic neurogenesis through Wnt-5a secretion. Mol Cell Neurosci 31, 251-262.
6. Castelo-Branco, G., Wagner, J., Rodriguez, F. J., Kele, J., Sousa, K., Rawal, N., Pasolli, H. A., Fuchs, E., Kitajewski, J., and Arenas, E. (2003). Differential regulation of midbrain dopaminergic neuron development by Wnt-1, Wnt-3a, and Wnt-5a. Proc Natl Acad Sci USA 100, 12747-12752.
7. Chung, S., Sonntag, K. C., Andersson, T., Bjorklund, L. M., Park, J. J., Kim, D. W., Kang, U. J., Isacson, O., and Kim, K. S. (2002). Genetic engineering of mouse embryonic stem cells by Nurr1 enhances differentiation and maturation into dopaminergic neurons. Eur J Neurosci 16, 1829-1838.
8. Chung, S., Hedlund, E., Hwang, M., Kim, D. W., Shin, B. S., Hwang, D. Y., Jung Kang, U., Isacson, O., and Kim, K. S. (2005). The homeodomain transcription factor Pitx3 facilitates differentiation of mouse embryonic stem cells into AHD2-expressing dopaminergic neurons. Mol Cell Neurosci 28, 241-252.
9. Chung, S., Shin, B. S., Hedlund, E., Pruszak, J., Ferree, A., Kang, U. J., Isacson, O., and Kim, K. S. (2006a). Genetic selection of sox1GFP-expressing neural precursors removes residual tumorigenic pluripotent stem cells and attenuates tumor formation after transplantation. J Neurochem 97, 1467-1480.
10. Chung, S., Shin, B. S., Hwang, M., Lardaro, T., Kang, U. J., Isacson, O., and Kim, K. S. (2006b). Neural precursors derived from embryonic stem cells, but not those from fetal ventral mesencephalon, maintain the potential to differentiate into dopaminergic neurons after expansion in vitro. Stem Cells 24, 1583-1593.
11. Chung, S., Leung, A., Han, B. S., Chang, M. Y., Moon, J. I., Kim, C. H., Hong, S., Pruszak, J., Isacson, O., and Kim, K. S. (2009). Wnt1-lmx1a forms a novel autoregulatory loop and controls midbrain dopaminergic differentiation synergistically with the SHH-FoxA2 pathway. Cell Stem Cell 5, 646-658.
12. Chung, S., Moon, J., Leung, A., Aldrich, D., Li, Y., Bolshakove, V., Lamonerie, T., and Kim, K. S. (2011a). Embryonic stem cell-derived renewable and functional midbrain dopaminergic progenitors. (Under revision at PNAS).
13. Chung, S., Moon, J., Lukianov, S., and Kim, K.-S. (2011b). Co-activation of SHH pathway and Wnt1 pathway by Lmx1a, Otx2 and FoxA2 expression synergistically induces phenotype specification of midbrain dopaminergic neuronal precursors from differentiating human embryonic stem cells. Manuscript in Preparation.
14. Elkabetz, Y., Panagiotakos, G., Al Shamy, G., Socci, N. D., Tabar, V., and Studer, L. (2008). Human ES cell-derived neural rosettes reveal a functionally distinct early neural stem cell stage. Genes Dev 22, 152-165.
15. Eriksen, J., Rasmussen, S. G., Rasmussen, T. N., Vaegter, C. B., Cha, J. H., Zou, M. F., Newman, A. H., and Gether, U. (2009). Visualization of dopamine transporter trafficking in live neurons by use of fluorescent cocaine analogs. J Neurosci 29, 6794-6808.
16. Fasano, C. A., Chambers, S. M., Lee, G., Tomishima, M. J., and Studer, L. (2010). Efficient derivation of functional floor plate tissue from human embryonic stem cells. Cell Stem Cell 6, 336-347.
17. Hebsgaard, J. B., Nelander, J., Sabelstrom, H., Jonsson, M. E., Stott, S., and Parmar, M. (2009). Dopamine neuron precursors within the developing human mesencephalon show radial glial characteristics. Glia 57, 1648-1658.
18. Hedlund, E., Pruszak, J., Lardaro, T., Ludwig, W., Vinuela, A., Kim, K. S., and Isacson, O. (2008). Embryonic stem cell-derived Pitx3-enhanced green fluorescent protein midbrain dopamine neurons survive enrichment by fluorescence-activated cell sorting and function in an animal model of Parkinson's disease. Stem Cells 26, 1526-1536.
19. Hemre, K. M., Keller-Peck, C. R., Campbell, R. M., Peterson, A. C., Mullen, R. J., and Goldowitz, D. (1996). Annexin IV is a marker of roof and floor plate development in the murine CNS. J Comp Neurol 368, 527-537.
20. Hockemeyer D, Soldner F, Beard C, Gao Q, Mitalipova M, DeKelver R C, Katibah G E, Amora R, Boydston E A, Zeitler B, Meng X, Miller J C, Zhang L, Rebar E J, Gregory P D, Urnov F D, Jaenisch R. (2009) Efficient targeting of expressed and silent genes in human ESCs and iPSCs using zinc-finger nucleases. Nat Biotechnol 27(9):851-857.
21. Hong, S., Hwang, D. Y., Yoon, S., Isacson, O., Ramezani, A., Hawley, R. G., and Kim, K. S. (2007). Functional analysis of various promoters in lentiviral vectors at different stages of in vitro differentiation of mouse embryonic stem cells. Mol Ther 15, 1630-1639.
22. Hong, S., Kang, U. J., Isacson, O., and Kim, K. S. (2008). Neural precursors derived from human embryonic stem cells maintain long-term proliferation without losing the potential to differentiate into all three neural lineages, including dopaminergic neurons. J Neurochem 104, 316-324.
23. Hwang, D. Y., Ardayfio, P., Kang, U. J., Semina, E. V., and Kim, K. S. (2003). Selective loss of dopaminergic neurons in the substantia nigra of Pitx3-deficient aphakia mice. Brain Res Mol Brain Res 114, 123-131.
24. Hwang, D. Y., Fleming, S. M., Ardayfio, P., Moran-Gates, T., Kim, H., Tarazi, F. I., Chesselet, M. F., and Kim, K. S. (2005). 3,4-dihydroxyphenylalanine reverses the motor deficits in Pitx3-deficient aphakia mice: behavioral characterization of a novel genetic model of Parkinson's disease. J Neurosci 25, 2132-2137.
25. Johe, K. K., Hazel, T. G., Muller, T., Dugich-Djordjevic, M. M., and McKay, R. D. (1996). Single factors direct the differentiation of stem cells from the fetal and adult central nervous system. Genes Dev 10, 3129-3140.
26. Kawasaki, H., Mizuseki, K., Nishikawa, S., Kaneko, S., Kuwana, Y., Nakanishi, S., Nishikawa, S. I., and Sasai, Y. (2000). Induction of midbrain dopaminergic neurons from ES cells by stromal cell-derived inducing activity. Neuron 28, 31-40.
27. Kim, J. H., Auerbach, J. M., Rodriguez-Gomez, J. A., Velasco, I., Gavin, D., Lumelsky, N., Lee, S. H., Nguyen, J., Sanchez-Pernaute, R., Bankiewicz, K., et al. (2002). Dopamine neurons derived from embryonic stem cells function in an animal model of Parkinson's disease. Nature 418, 50-56.
28. Kitajima, K., Koshimizu, U., and Nakamura, T. (1999). Expression of a novel type of classic cadherin, PB-cadherin in developing brain and limb buds. Dev Dyn 215, 206-214.
29. Kittappa, R., Chang, W. W., Awatramani, R. B., and McKay, R. D. (2007). The foxa2 gene controls the birth and spontaneous degeneration of dopamine neurons in old age. PLoS Biol 5, e325.
30. Kordower, J. H., and Brundin, P. (2009). Lewy body pathology in long-term fetal nigral transplants: is Parkinson's disease transmitted from one neural system to another? Neuropsychopharmacology 34, 254.
31. Kordower, J. H., Chu, Y., Hauser, R. A., Freeman, T. B., and Olanow, C. W. (2008). Lewy body-like pathology in longterm embryonic nigral transplants in Parkinson's disease. Nat Med 14, 504-506.
32. Lee, S. H., Lumelsky, N., Studer, L., Auerbach, J. M., and McKay, R. D. (2000). Efficient generation of midbrain and hindbrain neurons from mouse embryonic stem cells. Nat Biotech 18, 675-679.
33. Li, J. Y., Christophersen, N. S., Hall, V., Soulet, D., and Brundin, P. (2008a). Critical issues of clinical human embryonic stem cell therapy for brain repair. Trends Neurosci 31, 146-153.
34. Li, J. Y., Englund, E., Holton, J. L., Soulet, D., Hagell, P., Lees, A. J., Lashley, T., Quinn, N. P., Rehncrona, S., Bjorklund, A., et al. (2008b). Lewy bodies in grafted neurons in subjects with Parkinson's disease suggest host-to-graft disease propagation. Nat Med 14, 501-503.
35. Lindvall, O., and Bjorklund, A. (2004). Cell therapy in Parkinson's disease. NeuroRx 1, 382-393.
36. Lindvall, O., and Kokaia, Z. (2009). Prospects of stem cell therapy for replacing dopamine neurons in Parkinson's disease. Trends Pharmacol Sci 30, 260-267.
37. Mendez, I., Vinuela, A., Astradsson, A., Mukhida, K., Hallett, P., Robertson, H., Tierney, T., Holness, R., Dagher, A., Trojanowski, J. Q., et al. (2008). Dopamine neurons implanted into people with Parkinson's disease survive without pathology for 14 years. Nat Med 14, 507-509.
38. Nelander, J., Hebsgaard, J. B., and Parmar, M. (2009). Organization of the human embryonic ventral mesencephalon. Gene Expr Patterns 9, 555-561.
39. Oh, M. S., Hong, S. J., Huh, Y., and Kim, K. S. (2009). Expression of transgenes in midbrain dopamine neurons using the tyrosine hydroxylase promoter. Gene Ther 16, 437-440.
40. Ono, Y., Nakatani, T., Sakamoto, Y., Mizuhara, E., Minaki, Y., Kumai, M., Hamaguchi, A., Nishimura, M., Inoue, Y., Hayashi, H., et al. (2007). Differences in neurogenic potential in floor plate cells along an anteroposterior location: midbrain dopaminergic neurons originate from mesencephalic floor plate cells. Development 134, 3213-3225.
41. Panchision, D. M., Chen, H. L., Pistollato, F., Papini, D., Ni, H. T., and Hawley, T. S. (2007). Optimized flow cytometric analysis of central nervous system tissue reveals novel functional relationships among cells expressing CD133, CD15, and CD24. Stem Cells 25, 1560-1570.
42. Parish, C. L., Castelo-Branco, G., Rawal, N., Tonnesen, J., Sorensen, A. T., Salto, C., Kokaia, M., Lindvall, O., and Arenas, E. (2008). Wnt5a-treated midbrain neural stem cells improve dopamine cell replacement therapy in parkinsonian mice. J Clin Invest 118, 149-160.
43. Park C H, Minn Y K, Lee J Y, Choi D H, Chang M Y, Shim J W, Ko J Y, Koh H C, Kang M J, Kang J S, Rhie D J, Lee Y S, Son H, Moon S Y, Kim K S, Lee S H. (2005). In vitro and in vivo analyses of human embryonic stem cell-derived dopamine neurons. J. Neurochem. 2005 March; 92(5):1265-76.
44. Perrier, A. L., Tabar, V., Barberi, T., Rubio, M. E., Bruses, J., Topf, N., Harrison, N. L., and Studer, L. (2004). Derivation of midbrain dopamine neurons from human embryonic stem cells. Proc Natl Acad Sci USA 101, 12543-12548.
45. Politis, M., Wu, K., Loane, C., Quinn, N. P., Brooks, D. J., Rehncrona, S., Bjorklund, A., Lindvall, O., and Piccini, P. (2010). Serotonergic neurons mediate dyskinesia side effects in Parkinson's patients with neural transplants. Sci Transl Med 2, 38ra46.
46. Rezgaoui, M., Hermey, G., Riedel, I. B., Hampe, W., Schaller, H. C., and Hermans-Borgmeyer, I. (2001). Identification of S or CS2, a novel member of the VPS10 domain containing receptor family, prominently expressed in the developing mouse brain. Mech Dev 100, 335-338.
47. Roy, N. S., Cleren, C., Singh, S. K., Yang, L., Beal, M. F., and Goldman, S. A. (2006). Functional engraftment of human ES cell-derived dopaminergic neurons enriched by coculture with telomerase-immortalized midbrain astrocytes. Nat Med 12, 1259-1268.
48. Sanchez-Pernaute, R., Lee, H., Patterson, M., Reske-Nielsen, C., Yoshizaki, T., Sonntag, K. C., Studer, L., and Isacson, O. (2008). Parthenogenetic dopamine neurons from primate embryonic stem cells restore function in experimental Parkinson's disease. Brain 131, 2127-2139.
49. Schulte, G., Bryja, V., Rawal, N., Castelo-Branco, G., Sousa, K. M., and Arenas, E. (2005). Purified Wnt-5a increases differentiation of midbrain dopaminergic cells and dishevelled phosphorylation. J Neurochem 92, 1550-1553.
50. Schulz, T. C., Noggle, S. A., Palmarini, G. M., Weiler, D. A., Lyons, I. G., Pensa, K. A., Meedeniya, A. C., Davidson, B. P., Lambert, N. A., and Condie, B. G. (2004). Differentiation of human embryonic stem cells to dopaminergic neurons in serum-free suspension culture. Stem Cells 22, 1218-1238.
51. Shen, Q., Goderie, S. K., Jin, L., Karanth, N., Sun, Y., Abramova, N., Vincent, P., Pumiglia, K., and Temple, S. (2004). Endothelial cells stimulate self-renewal and expand neurogenesis of neural stem cells. Science 304, 1338-1340.
52. Summerhurst, K., Stark, M., Sharpe, J., Davidson, D., and Murphy, P. (2008). 3D representation of Wnt and Frizzled gene expression patterns in the mouse embryo at embryonic day 11.5 (Ts19). Gene Expr Patterns 8, 331-348.
53. Svendsen, C. (2008). Stem cells and Parkinson's disease: toward a treatment, not a cure. Cell Stem Cell 2, 412-413.
54. Takahashi, K., and Yamanaka, S. (2006). Induction of pluripotent stem cells from mouse embryonic and adult fibroblast cultures by defined factors. Cell 126, 663-676.
55. Wernig, M., Zhao, J. P., Pruszak, J., Hedlund, E., Fu, D., Soldner, F., Broccoli, V., Constantine-Paton, M., Isacson, O., and Jaenisch, R. (2008). Neurons derived from reprogrammed fibroblasts functionally integrate into the fetal brain and improve symptoms of rats with Parkinson's disease. Proc Natl Acad Sci USA 105, 5856-5861.
56. Ye, W., Shimamura, K., Rubenstein, J. L., Hynes, M. A., and Rosenthal, A. (1998). FGF and Shh signals control dopaminergic and serotonergic cell fate in the anterior neural plate. Cell 93, 755-766.
57. Zeng, X., Cai, J., Chen, J., Luo, Y., You, Z. B., Fotter, E., Wang, Y., Harvey, B., Miura, T., Backman, C., et al. (2004). Dopaminergic differentiation of human embryonic stem cells. Stem Cells 22, 925-940.
58. Zhu, Q., Runko, E., Imondi, R., Milligan, T., Kapitula, D., and Kaprielian, Z. (1998). New cell surface marker of the rat floor plate and notochord. Dev Dyn 211, 314-326.
59. Zisman, S., Marom, K., Avraham, O., Rinsky-Halivni, L., Gai, U., Kligun, G., Tzarfaty-Majar, V., Suzuki, T., and Klar, A. (2007). Proteolysis and membrane capture of F-spondin generates combinatorial guidance cues from a single molecule. J Cell Biol 178, 1237-1249.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method for purifying human midbrain dopaminergic neural progenitor cells comprising:
    (a) providing a human neural progenitor cell population comprising midbrain dopaminergic (mDA) neural progenitor cells in cell culture medium;
    (b) isolating human neural progenitor cells that express Corin and Frizzled-5 (Fzd5) from the cell population of step (a),
    wherein the isolating excludes cells that express Corin but which do not express Fzd5; and
    wherein isolating comprises contacting the mDA neural progenitor cells with i) an antibody specific for Corin and ii) an antibody specific for Fzd5; and selecting human neural progenitor cells which are bound by the antibodies of i) and ii),
    thereby purifying human mDA neural progenitor cells.

2. The method of claim 1, wherein the neural progenitor cell population is produced by a method comprising:
    (i) providing a cell population comprising pluripotent cells in cell culture medium; and
    (ii) differentiating at least some of the pluripotent cells into neural progenitor cells.

3. The method of claim 1, wherein the neural progenitor cell population is produced by a method comprising:
    (i) culturing a population of pluripotent cells in the presence of leukocyte inhibitory factor (LIF) and serum;
    (ii) culturing the cells produced in step (i) in the absence of LIF;
    (iii) culturing the cells produced in step (ii) in the absence of serum, and in the presence of insulin, transferin, selenium, and fibronectin; and
    (iv) isolating nestin-positive cells produced in step (iii) and culturing the nestin-positive cells in the presence of laminin and one or more growth factors selected from fibroblast growth factor 8 (FGF8) and basic fibroblast growth factor (bFGF), to produce a population of neural progenitor cells.

4. The method of claim 1, wherein the neural progenitor cell population is produced by a method comprising:
    (i) culturing a population of pluripotent cells in the presence of one or more growth factors selected from basic fibroblast growth factor (bFGF) and fibroblast growth factor 8 (FGF8);
    (ii) culturing the cells produced in step (i) in the presence of sonic hedgehog (SHH) protein and in the absence of serum; and
    (iii) culturing the cells obtained in step (ii) in the presence of bFGF to produce a population of neural progenitor cells.

5. The method of claim 1, wherein the neural progenitor cell population is produced by a method comprising:
    (i) culturing a population of pluripotent cells in the presence of one or more growth factors selected from fibroblast growth factor 8 (FGF8), epidermal growth factor (EGF), and basic fibroblast growth factor (bFGF);
    (ii) culturing the cells produced in step (i) in the absence of bFGF; and
    (iii) culturing the cells produced in step (ii) in the presence of bFGF to produce a population of neural progenitor cells.

6. The method of claim 1, wherein the neural progenitor cell population is a substantially homogenous cell population of Nestin-positive cells.

7. The method of claim 1, wherein the mDA neural progenitor cells produced in step (b) further express one or more of the markers selected from the group consisting of: forkhead box A2 (FoxA2); orthodenticle homeobox 2

(Otx2); LIM homeobox transcription factor 1, alpha (Lmx1a); LIM homeobox transcription factor 1, beta (Lmx1b); Glast; Vimentin; Nestin; glial fibrillary acidic protein (GFAP); and beta-tubulin.

8. The method of claim 1, wherein the mDA neural progenitor cells are further differentiated into a cell population of neuronal differentiated (ND) cells by culturing the mDA neural progenitor cells in the absence of growth factors selected from the group consisting of fibroblast growth factor 8 (FGF8) and basic fibroblast growth factor (bFGF).

9. The method of claim 8, further comprising removing epidermal growth factor (EGF) from the culture medium to produce a population of ND cells.

10. The method of claim 8, wherein the ND cells express:
(a) one or more markers selected from the group consisting of tyrosine hydroxylase, dopamine active transporter, and dopamine decarboxylase; and
(b) one or more markers selected from the group consisting of orthodenticle homeobox 2 (Otx2); paired-like homeodomain 3 (Pitx3); LIM homeobox transcription factor 1, alpha (Lmx1a); LIM homeobox transcription factor 1, beta (Lmx1b); forkhead box A2 (FoxA2); engrailed homeobox 1 (En-1); and nuclear receptor subfamily 4, group A, member 2 (Nurr1).

* * * * *